(12) United States Patent
Chen et al.

(10) Patent No.: US 11,827,625 B2
(45) Date of Patent: *Nov. 28, 2023

(54) PYRIMIDINE DERIVATIVE, METHOD FOR PREPARING SAME AND USE THEREOF IN MEDICINE

(71) Applicant: Zhejiang Hisun Pharmaceutical Co., Ltd., Taizhou (CN)

(72) Inventors: Lei Chen, Taizhou (CN); Dongliang Guan, Taizhou (CN); Hua Bai, Taizhou (CN); Jun Gou, Taizhou (CN); Weifeng Zhao, Taizhou (CN); Zhongli Wang, Taizhou (CN); Long Ling, Taizhou (CN); Yutao Ma, Taizhou (CN)

(73) Assignee: Zhejiang Hisun Pharmaceutical Co., Ltd.

( * ) Notice: Subject to any disclaimer, the term of this patent is extended or adjusted under 35 U.S.C. 154(b) by 266 days.

This patent is subject to a terminal disclaimer.

(21) Appl. No.: 17/218,380

(22) Filed: Mar. 31, 2021

(65) Prior Publication Data
US 2021/0221797 A1    Jul. 22, 2021

Related U.S. Application Data

(62) Division of application No. 16/800,057, filed on Feb. 25, 2020, now Pat. No. 11,001,572, which is a division of application No. 16/302,310, filed as application No. PCT/CN2017/085135 on May 19, 2017, now Pat. No. 10,654,836.

(30) Foreign Application Priority Data

May 20, 2016    (CN) .......................... 201610341444.0

(51) Int. Cl.
| | | |
|---|---|---|
| *A61K 31/506* | (2006.01) | |
| *C07D 403/14* | (2006.01) | |
| *C07D 403/12* | (2006.01) | |
| *C07D 471/10* | (2006.01) | |
| *C07D 487/10* | (2006.01) | |
| *A61P 35/00* | (2006.01) | |
| *C07D 403/04* | (2006.01) | |

(52) U.S. Cl.
CPC .......... *C07D 403/14* (2013.01); *A61K 31/506* (2013.01); *A61P 35/00* (2018.01); *C07D 403/04* (2013.01); *C07D 403/12* (2013.01); *C07D 471/10* (2013.01); *C07D 487/10* (2013.01); *Y02P 20/55* (2015.11)

(58) Field of Classification Search
CPC .................................................. A61K 31/506
See application file for complete search history.

(56) References Cited

FOREIGN PATENT DOCUMENTS

| | | |
|---|---|---|
| WO | 2015057938 A1 | 4/2015 |
| WO | 2015057963 A1 | 4/2015 |
| WO | 2015059668 A1 | 4/2015 |

OTHER PUBLICATIONS

Brown et al., "Cartilage Dysplasia and Tissue Mineralization in the Rat Following Administration of a FGF Receptor Tyrosine Kinase Inhibitor"; Toxicologic Pathology, vol. 33:4; p. 449-455, Jun. 1, 2005.
Extended European Search Report with Written Opinion for Application No. 17798784.9 dated Dec. 13, 2019, 8 pages.
French et al., "Targeting FGFR4 Inhibits Hepatocellular Carcinoma in Preclinical Mouse Models", Plos One vol. 7:5, May 2012, p. 1-12.
International Search Report for Application No. PCT/CN2017/085135, dated May 19, 2017.
Sia et al., "Integrative Molecular Analysis of Intrahepatic Cholangiocarcinoma Reveals 2 Classes That Have Different Outcomes," Gastroenterology Apr. 2013; 144:.4, p. 829-840.

*Primary Examiner* — Brian E McDowell
(74) *Attorney, Agent, or Firm* — Lerner David LLP

(57) ABSTRACT

The present invention relates to a pyrimidine derivative, a method for preparing same and use thereof in medicine. In particular, the present invention relates to a pyrimidine derivative represented by general formula (I), a method for preparing same and a pharmaceutically acceptable salt thereof as well as use thereof as a therapeutic agent, in particular as a FGFR4 kinase inhibitor, definitions of each substituent in the general formula (I) being the same as those defined in the description.

(I)

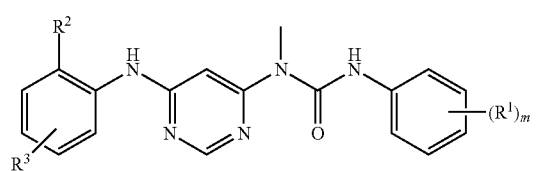

8 Claims, 3 Drawing Sheets

PYRIMIDINE DERIVATIVE, METHOD FOR PREPARING SAME AND USE THEREOF IN MEDICINE

CROSS REFERENCE TO RELATED APPLICATIONS

The present application is a divisional application of U.S. patent application Ser. No. 16/800,057 filed Feb. 25, 2020, which is a divisional application of U.S. patent application Ser. No. 16/302,310 filed Nov. 16, 2018 and issued as U.S. Pat. No. 10,654,836 on May 19, 2020, which is a national phase entry under 35 U.S.C. § 371 of International Application No. PCT/CN2017/085135 filed May 19, 2017, which claims priority from Chinese Patent Application No. 201610341444.0 filed May 20, 2016, all of which are hereby incorporated herein by reference.

TECHNICAL FIELD

The present invention relates to a novel pyrimidine derivative, preparation method thereof and a pharmaceutical composition containing the derivative, and relates to the use thereof as a therapeutic agent, in particular as a FGFR4 inhibitor.

BACKGROUND ART

The fibroblast growth factor receptor (FGFR) family is composed of four members (FGFR1, FGFR2, FGFR3, and FGFR4), which is a kinase belonging to the receptor tyrosine kinase family, and the binding of FGF leads to FGFR dimerization, followed by autologous phosphorylation of receptors and activation of downstream signaling pathways. Activation of receptors is sufficient to regenerate and activate specific downstream signaling partners involved in the regulation of diverse processes such as cell growth, cell metabolism, and cell survival. Therefore, the FGF/FGFR signaling pathway has multiple effects in many critical cellular biological processes such as tumor cell proliferation, migration, infiltration, and angiogenesis. The four members of the FGFR family differ from each other in terms of their ligand affinity and tissue distribution. The genomic structure of the FGFR-4 gene contains 18 exons.

Human FGF19 gene is located at 11q13.1, the specific binding of FGFR4 to its ligand FGF19 inhibits cell apoptosis and NF-kB signaling, and up-regulates expression of genes involved in cell proliferation; activation of FGFR4 may lead to a decrease in Ikkβ activity in TNF-α-treated cells, along with the reduction of NF-kB distribution in cells, and attenuates the cell apoptotic effect. Four FGFR genes are expressed in human liver, but mature hepatocyte only expresses FGFR4 in large amounts. The binding of FGFR4 to its ligand can also regulate the metabolism of bile acid. The balance of the conversion of cholesterol to bile acid in the body is closely related to various normal physiological functions of the body. Damage of this balance can cause various diseases, for example fatty liver and cardiovascular and cerebrovascular diseases such as arteriosclerosis. Therefore, the interaction between FGFR4 and FGF19 has become a new target for cholesterol-lowering drugs in the treatment of diseases such as hyperlipidemia.

In recent years, more and more evidence indicates that there are gene amplification mutations of FGFR1, FGFR2, FGFR3 and FGFR4 in various types of cancer. A large amount of evidence indicates that FGFR1 has gene mutations in breast cancer, non-small cell lung cancer and glioblastoma, has fusion protein formation caused by gene transposition in acute myeloid leukemia, and has over-expression in pancreatic cancer, bladder cancer, prostate cancer, and esophageal cancer; FGFR2 has gene mutations and amplification in gastric cancer, breast cancer and uterine cancer, and has over-expression in prostate cancer, esophageal cancer, ovarian cancer, pancreatic cancer, brain tumor, and colorectal cancer; FGFR3 has gene mutations in multiple myeloma and bladder cancer, and has over-expression in ovarian cancer, non-small cell lung cancer, and hepatocellular carcinoma; FGFR4 has gene mutations and over-expression in lung cancer, ovarian cancer, prostate cancer, hepatocellular carcinoma and cholangiocarcinoma etc., and also has over-expression in thyroid cancer, ovarian cancer, etc. (French et al. 2012 PLos ONE 7(5):e367313; Sia et al. 2013 Gastroejterology 144:829-840).

A series of patents about FGFR inhibitor have been published, however, there are fewer patent disclosures on selective inhibition of FGFR4, and inhibitors selective for FGFR4 have less toxicity than FGFR inhibitors (Brown, A P et al (2005), Toxocol. Pathol., 449-455). FGFR4 inhibitors currently in clinical include FGF-401 (Novartis, clinical phase II), BLU-554 (Blueprint, clinical phase I) and H3B6527 (Eisai, clinical phase I). Patents for selective inhibition of FGFR4 include WO2015059668, WO2015057938, and WO2015057963, etc. Currently, research on FGFR4 inhibitors against tumors such as hepatocellular carcinoma is insufficient, and it is still necessary to study and develop new FGFR4 inhibitors.

SUMMARY OF THE INVENTION

One of the objects of the present invention is to disclose a new class of pyrimidine derivatives and pharmaceutically acceptable salts thereof.

The present invention provides a compound represented by formula (I) or a stereoisomer, tautomer thereof or a pharmaceutically acceptable salt thereof:

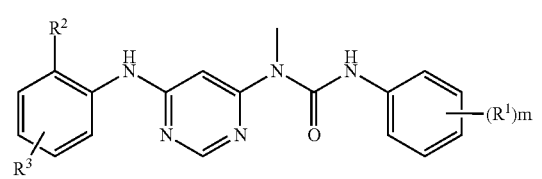

wherein:
each of $R^1$ is independently selected from alkyl, halogen, alkoxy, cycloalkyl, heterocyclyl, aryl, heteroaryl, —$NR^7R^8$, —$C(O)NR^7R^8$, —$C(O)R^9$, —$C(O)OR^9$ or —$NR^7C(O)R^8$, wherein the alkyl, alkoxy, cycloalkyl, heterocyclyl, aryl or heteroaryl is optionally further substituted by one or more substituents selected from the group consisting of hydroxyl, halogen, nitro, cyano, alkyl, alkoxy, cycloalkyl, heterocyclyl, aryl, heteroaryl, —$NR^7R^8$, —$C(O)NR^7R^8$, —$C(O)R^9$, —$C(O)OR^9$ and —$NR^7C(O)R^8$;

$R^2$ is selected from the group:
—$NR^4C(O)CR^5$=$CHR^6$ or —$NR^4C(O)C$≡$CR^5$;

$R^3$ is a spiroheterocyclyl, wherein the spiroheterocyclyl is optionally further substituted by one or more substituents selected from the group consisting of hydroxyl, halogen, nitro, cyano, alkyl, alkoxy, cycloalkyl, heterocyclyl, aryl, heteroaryl, haloalkoxy, —NR⁷R⁸, —C(O)NR⁷R⁸, —C(O)R⁹, —C(O)OR⁹ and —NR⁷C(O)R⁸; or R³ is a monocyclic heterocyclyl, wherein the monocyclic heterocyclyl is further substituted by one or more substituents selected from the group consisting of cycloalkyl and —NR⁷R⁸;

each of R⁴ is independently selected from hydrogen or alkyl, wherein the alkyl is optionally further substituted by one or more substituents selected from the group consisting of hydroxy, halogen, nitro, cyano, alkyl, alkoxy, cycloalkyl, heterocyclyl, aryl, heteroaryl, haloalkoxy, —NR⁷R⁸, —C(O)NR⁷R⁸, —C(O)R⁹, —C(O)OR⁹ and —NR⁷C(O)R⁸;

R⁵ and R⁶ are each independently selected from hydrogen, alkyl or halogen, wherein the alkyl is optionally further substituted by one or more substituents selected from the group consisting of hydroxy, halogen, nitro, cyano, alkyl, alkoxy, cycloalkyl, heterocyclyl, aryl, heteroaryl, haloalkoxy, —NR⁷R⁸, —C(O)NR⁷R⁸, —C(O)R⁹, —C(O)OR⁹ and —NR⁷C(O)R⁸;

R⁷, R⁸ and R⁹ are each independently selected from hydrogen, alkyl, cycloalkyl, heterocyclyl, aryl or heteroaryl, wherein the alkyl, cycloalkyl, heterocyclyl, aryl or heteroaryl are optionally further substituted by one or more substituents selected from the group consisting of hydroxy, halogen, nitro, cyano, alkyl, alkoxy, cycloalkyl, heterocyclyl, aryl, heteroaryl, —NR¹⁰R¹¹, —C(O)NR¹⁰R¹¹, —C(O)R¹², —C(O)OR¹² and —NR¹⁰C(O)R¹¹;

alternatively, R⁷ and R⁸ together with the N atom to which they are attached form a 4 to 8 membered heterocyclyl, wherein the 4 to 8 membered heterocyclic ring contains one or more N, O, S(O)ₙ atoms, and the 4 to 8 membered heterocyclic ring is further substituted by one or more substituents selected from the group consisting of hydroxy, halogen, nitro, cyano, alkyl, alkoxy, cycloalkyl, heterocyclyl, aryl, heteroaryl, =O, —NR¹⁰R¹¹, —C(O)NR¹⁰R¹¹, —C(O)R¹², —C(O)OR¹² and —NR¹⁰C(O)R¹¹;

R¹⁰, R¹¹ and R¹² are each independently selected from hydrogen, alkyl, cycloalkyl, heterocyclyl, aryl or heteroaryl, wherein the alkyl, cycloalkyl, heterocyclyl, aryl or heteroaryl is optionally further substituted by one or more substituents selected from the group consisting of hydroxy, halogen, nitro, cyano, alkyl, alkoxy, cycloalkyl, heterocyclyl, aryl, heteroaryl, carboxylic acid and carboxylate;

m is 1, 2, 3 or 4; and n is 0, 1, or 2.

A preferred embodiment of the present invention provides a compound of formula (I) or a stereoisomer, tautomer thereof or a pharmaceutically acceptable salt thereof, wherein R³ is a spiroheterocyclyl, wherein the spiroheterocyclyl is optionally further substituted by one or more substituents selected from the group consisting of hydroxy, halogen, nitro, cyano, alkyl, alkoxy, cycloalkyl, heterocyclyl, aryl, heteroaryl, haloalkoxy, —NR⁷R⁸, —C(O)NR⁷R⁸, —C(O)R⁹, —C(O)OR⁹ and —NR⁷C(O)R⁸, and R⁷, R⁸ and R⁹ are as defined in formula (I).

A preferred embodiment of the present invention provides a compound of formula (I) or a stereoisomer, tautomer thereof or a pharmaceutically acceptable salt thereof, which is a compound of formula (II) or a stereoisomer, tautomer thereof or a pharmaceutically acceptable salt thereof:

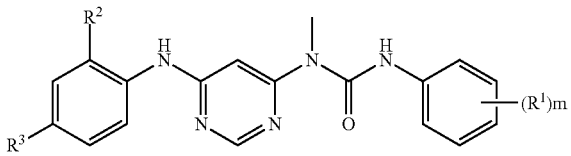

wherein R¹ to R³ and m are as defined in formula (I).

A preferred embodiment of the present invention provides a compound of formula (I) or a stereoisomer, tautomer thereof or a pharmaceutically acceptable salt thereof, wherein R¹ is selected from halogen or alkoxy, preferably chlorine or methoxyl.

A preferred embodiment of the present invention provides a compound of formula (I) or a stereoisomer, tautomer thereof or a pharmaceutically acceptable salt thereof, wherein R² is —NHC(O)CH=CH₂.

A preferred embodiment of the present invention provides a compound of formula (I) or a stereoisomer, tautomer thereof or a pharmaceutically acceptable salt thereof, wherein R³ is a monospiroheterocyclyl, preferably a 3-membered/6-membered, 4-membered/4-membered, 4-membered/5-membered, 4-membered/6-membered, 5-membered/5-membered or 5-membered/6-membered monospiroheterocyclyl, wherein the monospiroheterocyclyl is optionally further substituted by one or more substituents selected from the group consisting of alkyl, alkoxy, cycloalkyl, heterocyclyl, aryl and heteroaryl.

A preferred embodiment of the present invention provides a compound of formula (I) or a stereoisomer, tautomer thereof or a pharmaceutically acceptable salt thereof, wherein R² is —NHC(O)CH=CH₂, R³ is selected from 3-membered/6-membered, 4-membered/4-membered, 4-membered/5-membered, 4-membered/6-membered, 5-membered-/5-membered or 5-membered/6-membered monospiroheterocyclyl, wherein the monospiroheterocyclyl is optionally further substituted by alkyl, the alkyl is preferably methyl or ethyl.

A preferred embodiment of the present invention provides a compound of formula (I) or a stereoisomer, tautomer thereof or a pharmaceutically acceptable salt thereof, wherein R² is —NHC(O)CH=CH₂, R³ is selected from:

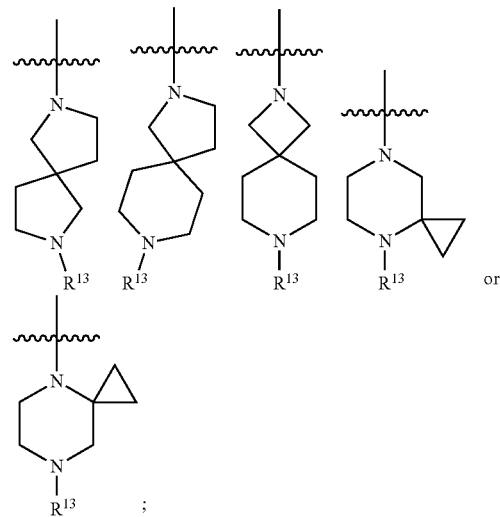

each $R^{13}$ is independently selected from hydrogen, alkyl, alkoxy, cycloalkyl, heterocyclyl, aryl or heteroaryl, preferably hydrogen or alkyl, the alkyl is preferably ethyl.

A preferred embodiment of the present invention provides a compound of formula (I) or a stereoisomer, tautomer thereof or a pharmaceutically acceptable salt thereof, wherein $R^2$ is —NHC(O)CH=CH$_2$; $R^3$ is selected from 4-membered to 6-membered monocyclic heterocyclyl; preferably piperidinyl or piperazinyl, wherein the piperidinyl or piperazinyl is further substituted by one or more substituents selected from the group consisting of cycloalkyl and —NR$^7$R$^8$, wherein $R^7$ and $R^8$ are as defined in formula (I).

Further, a preferred embodiment of the present invention provides a compound of formula (I) or a stereoisomer, tautomer thereof or a pharmaceutically acceptable salt thereof, wherein $R^2$ is —NHC(O)CH=CH$_2$; $R^3$ is selected from 4-membered to 6-membered monocyclic heterocyclyl; preferably piperidinyl or piperazinyl, wherein the piperidinyl or piperazinyl is further substituted by one or more substituents selected from the group consisting of $C_3$-8 cycloalkyl and —NR$^7$R$^8$, wherein the $C_{3-8}$ cycloalkyl is preferably cyclopropyl, and each of $R^7$ and $R^8$ is independently preferably hydrogen or alkyl, and the alkyl is preferably methyl.

Typical compounds of the present invention include, but are not limited to:

| Example No. | Structure | Name |
|---|---|---|
| 1 | 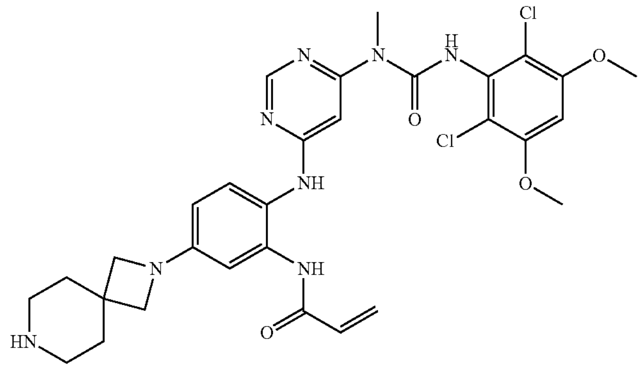 [SMILES: C=CC(=O)Nc1cc(N2CC3(CCNCC3)C2)ccc1Nc1cc(N(C)C(=O)Nc2c(Cl)c(OC)cc(OC)c2Cl)ncn1] | N-(2-((6-(3-(2,6-dichloro-3,5-dimethoxyphenyl)-1-methylureido)pyrimidin-4-yl)amino)-5-(2,7-diazaspiro[3.5]nonan-2-yl)phenyl)acrylamide |
| 2 | 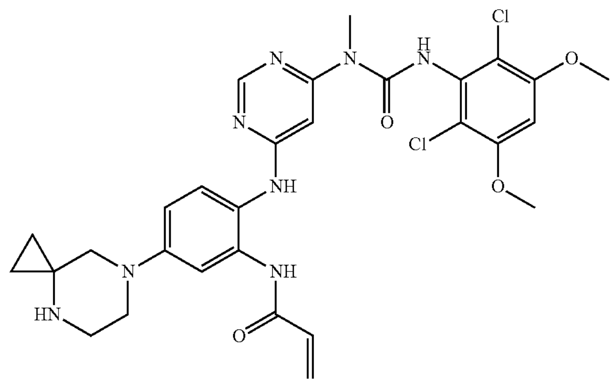 [SMILES: C=CC(=O)Nc1cc(N2CCNC3(CC3)C2)ccc1Nc1cc(N(C)C(=O)Nc2c(Cl)c(OC)cc(OC)c2Cl)ncn1] | N-(2-((6-(3-(2,6-dichloro-3,5-dimethoxyphenyl)-1-methylureido)pyrimidin-4-yl)amino)-5-(4,7-diazaspiro[2.5]octan-7-yl)phenyl)acrylamide |
| 3 | 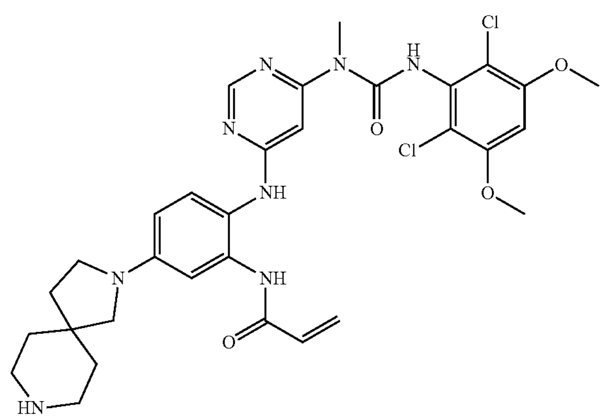 [SMILES: C=CC(=O)Nc1cc(N2CCC3(CCNCC3)C2)ccc1Nc1cc(N(C)C(=O)Nc2c(Cl)c(OC)cc(OC)c2Cl)ncn1] | N-(2-((6-(3-(2,6-dichloro-3,5-dimethoxyphenyl)-1-methylureido)pyrimidin-4-yl)amino)-5-(2,8-diazaspiro[4.5]decan-2-yl)phenyl)acrylamide |

-continued

| Example No. | Structure | Name |
|---|---|---|
| 4 | 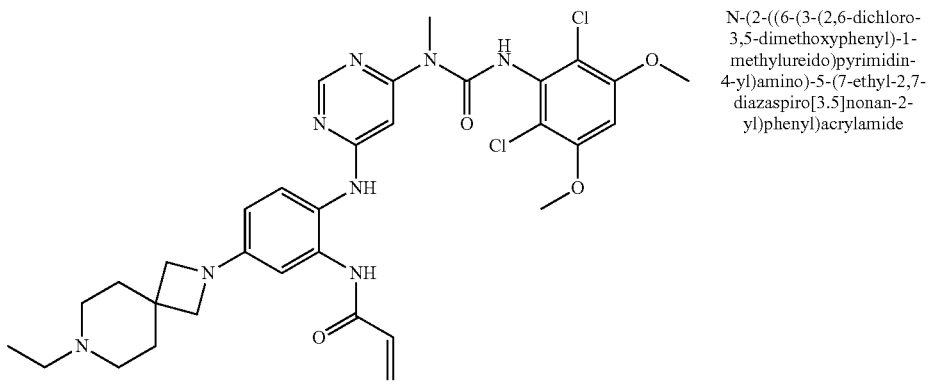 | N-(2-((6-(3-(2,6-dichloro-3,5-dimethoxyphenyl)-1-methylureido)pyrimidin-4-yl)amino)-5-(7-ethyl-2,7-diazaspiro[3.5]nonan-2-yl)phenyl)acrylamide |
| 5 | 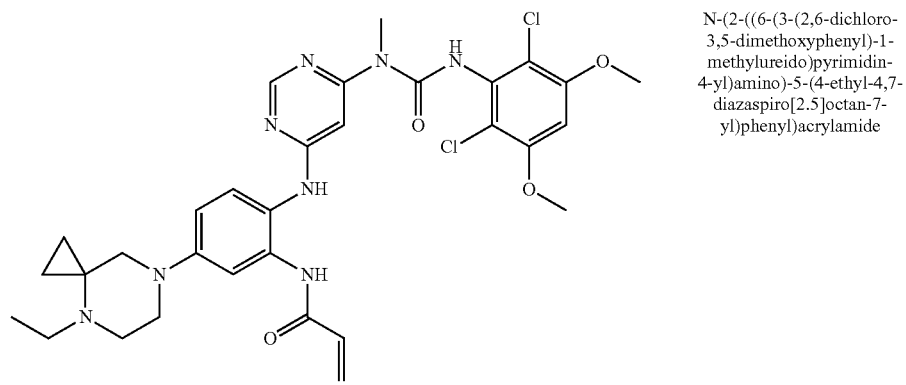 | N-(2-((6-(3-(2,6-dichloro-3,5-dimethoxyphenyl)-1-methylureido)pyrimidin-4-yl)amino)-5-(4-ethyl-4,7-diazaspiro[2.5]octan-7-yl)phenyl)acrylamide |
| 6 | 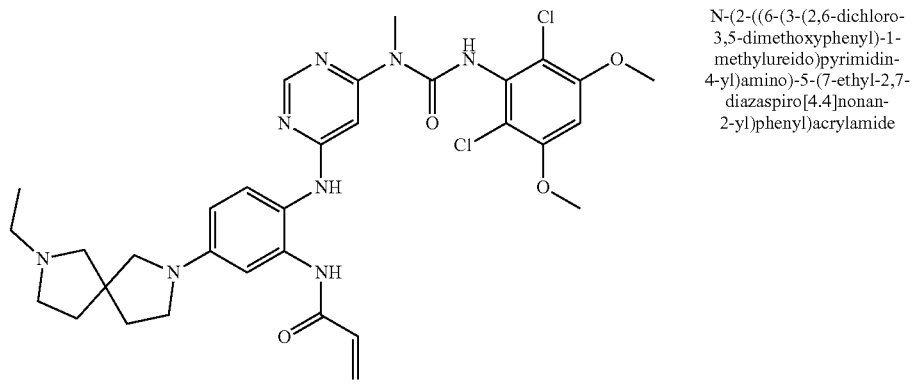 | N-(2-((6-(3-(2,6-dichloro-3,5-dimethoxyphenyl)-1-methylureido)pyrimidin-4-yl)amino)-5-(7-ethyl-2,7-diazaspiro[4.4]nonan-2-yl)phenyl)acrylamide |

| Example No. | Structure | Name |
|---|---|---|
| 7 | 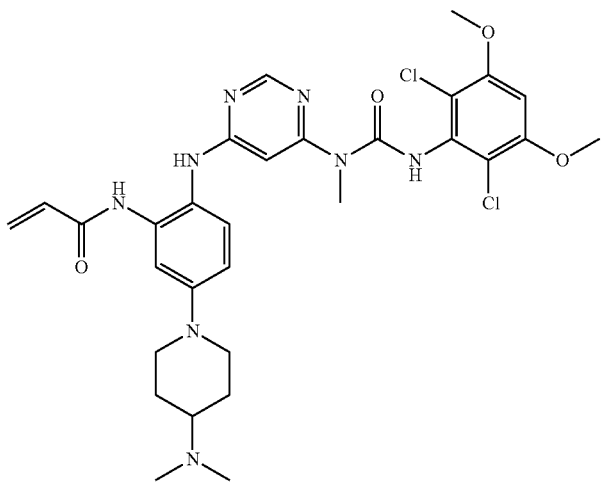 [SMILES: C=CC(=O)Nc1cc(N2CCC(N(C)C)CC2)ccc1Nc1cc(N(C)C(=O)Nc2c(Cl)c(OC)cc(OC)c2Cl)ncn1] | N-(2-((6-(3-(2,6-dichloro-3,5-dimethoxyphenyl)-1-methylureido)pyrimidin-4-yl)amino)-5-(4-(dimethylamino)piperidin-1-yl)phenyl)acrylamide |
| 8 | 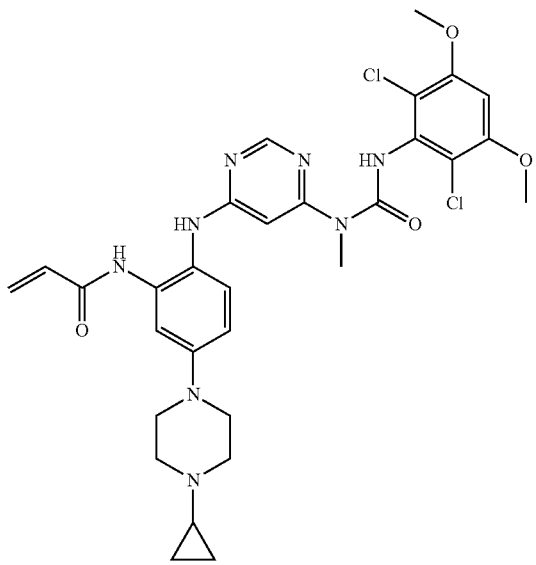 [SMILES: C=CC(=O)Nc1cc(N2CCN(C3CC3)CC2)ccc1Nc1cc(N(C)C(=O)Nc2c(Cl)c(OC)cc(OC)c2Cl)ncn1] | N-(5-(4-cyclopropylpiperazin-1-yl)-2-((6-(3-(2,6-dichloro-3,5-dimethoxyphenyl)-1-)methylureido)pyrimidin-4-yl)amino)phenyl)acrylamide |

| Example No. | Structure | Name |
|---|---|---|
| 9 | | N-(5-(4-(cyclopropyl(methyl)amino)piperidin-1-yl)-2-((6-(3-(2,6-dichloro-3,5-dimethoxy)phenyl)-1-methylureido)-4-yl)amino)phenyl)acrylamide | or stereoisomers, tautomers thereof or pharmaceutically acceptable salts thereof.

Further, the present invention provides a preparation method for the compound of formula (I), the method comprises:

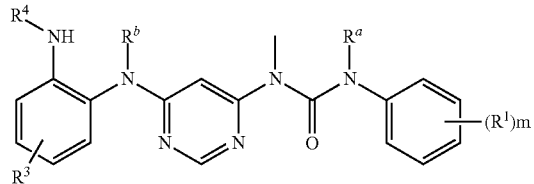
(Ie)

reacting a compound of formula (Ie) with an acyl halide compound, preferably X—C(O)CR⁵=CHR⁶ or X—C(O)C≡CR⁵, and further removing the amino protecting group IV to obtain a compound of formula (If);

when R³ contains —NH₂ or —NH—, —NH₂ or —NH— may optionally be protected by an N protecting group; the N protecting group is preferably —C(O)R⁹, more preferably tert-butoxycarbonyl;

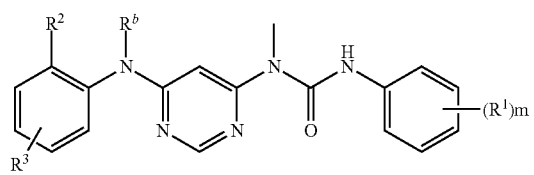
(If)

further removing the amino protecting group $R^b$ of the compound of formula (If) to obtain the compound of formula (I);

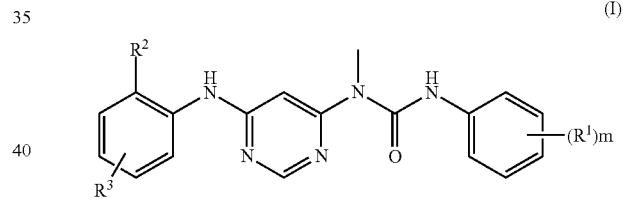
(I)

wherein:
$R^a$ and $R^b$ are each independently selected from N protecting groups, preferably phenylsulfonyl, benzyloxycarbonyl, formyl, trifluoroacetyl or tert-butoxycarbonyl; more preferably phenylsulfonyl or tert-butoxycarbonyl;
X is halogen;
$R^1$ to $R^6$, $R^9$ and m are as defined in formula (I).

Furthermore, the present invention provides a pharmaceutical composition comprising an effective amount of the compound of formula (I) or (II) or the stereoisomer, tautomer thereof or the pharmaceutically acceptable salt thereof, and a pharmaceutically acceptable carrier, excipient or a combination thereof.

The present invention provides a method for inhibiting FGFR4, which comprises contacting the receptor with the compound of any one of formula (I) and (II) or the stereoisomer, tautomer thereof or the pharmaceutically acceptable salt thereof, or the pharmaceutical composition thereof.

The present invention provides use of the compound of formula (I) or (II) or the stereoisomer, tautomer thereof or the pharmaceutically acceptable salt thereof, or the pharmaceutical composition thereof in preparation of drugs of FGFR4 inhibitors.

The present invention provides use of the compound of formula (I) or (II) or the stereoisomer, tautomer thereof or the pharmaceutically acceptable salt thereof, or the pharmaceutical composition thereof in preparation of drugs for treating diseases of FGFR4 over-expression.

The present invention provides use of the compound of formula (I) or (II) or the stereoisomer, tautomer thereof or the pharmaceutically acceptable salt thereof, or the pharmaceutical composition thereof in preparation of drugs for treating diseases of FGF19 amplification.

The present invention provides use of the compound of formula (I) or (II) or the stereoisomer, tautomer thereof or a pharmaceutically acceptable salt thereof, or the pharmaceutical composition thereof in preparation of drugs for treating cancer, wherein the cancer is selected from the group consisting of non-small cell lung cancer, gastric cancer, multiple myeloma, hepatocellular carcinoma, cholangiocarcinoma, preferably hepatocellular carcinoma and cholangiocarcinoma.

The present invention provides a method for treating cancer, which comprises administering to a patient in need of treatment an effective amount of the compound of formula (I) or (II) or the stereoisomer, tautomer thereof or the pharmaceutically acceptable salt thereof, or the pharmaceutical composition thereof, wherein the cancer is selected from the group consisting of non-small cell lung cancer, gastric cancer, multiple myeloma, hepatocellular carcinoma, cholangiocarcinoma, preferably hepatocellular carcinoma and cholangiocarcinoma.

The present invention provides a method for treating diseases of FGFR4 over-expression, which comprises administering to a patient in need of treatment an effective amount of the compound of formula (I) or (II) or the stereoisomer, tautomer thereof or the pharmaceutically acceptable salt thereof, or the pharmaceutical composition thereof.

The present invention provides a method for treating diseases of FGF19 amplification, which comprises administering to a patient in need of treatment an effective amount of the compound of formula (I) or (II) or the stereoisomer, tautomer thereof or the pharmaceutically acceptable salt thereof, or the pharmaceutical composition thereof.

DETAILED DESCRIPTION OF THE INVENTION

Unless otherwise stated, some of the terms used in the specification and claims of the present invention are defined as follows:

"Alkyl" refers to an aliphatic hydrocarbon group comprising a $C_1$-$C_{20}$ straight-chain or branched-chain when used as a group or part of a group, preferably a $C_1$-$C_{10}$ alkyl, more preferably a $C_1$-$C_6$ alkyl. Examples of alkyl groups include, but are not limited to, methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl and so on. The alkyl may be substituted or unsubstituted.

"Cycloalkyl" refers to a saturated or partially saturated monocyclic, fused, bridged, or spiro carbon ring, preferably a $C_3$-$C_{12}$ cycloalkyl, more preferably a $C_3$-$C_8$ cycloalkyl, and most preferably a $C_3$-$C_6$ cycloalkyl. Examples of monocyclic cycloalkyl include, but are not limited to, cyclopropyl, cyclobutyl, cyclopentyl, cyclopentenyl, cyclohexyl, cyclohexenyl, cyclohexadienyl, cycloheptyl, cycloheptatrienyl, cyclooctyl and so on, preferably cyclopropyl or cyclohexenyl.

"Spirocycloalkyl" refers to a 5 to 18 membered polycyclic group comprising two or more cyclic structures with single ring sharing one common carbon atom (named as spiro atom), which may contain one or more double bonds, but none of the rings have a completely conjugated π-electron aromatic system. Preferably 6 to 14 membered, more preferably 7 to 10 membered. The spirocycloalkyl is classified into monospiro, dispiro, or multispiro cycloalkyl depending on the number of the spiro atoms shared between the rings, preferably monospiro or dispiro cycloalkyl, preferably 4-membered/5-membered, 4-membered/6-membered, 5-membered/5-membered, or 5-membered/6-membered. Non-limiting examples of "spirocycloalkyl" include, but are not limited to spiro[4.5]decyl, spiro[4.4]nonyl, spiro[3.5]nonyl, spiro[2.4]heptyl.

"Fused cycloalkyl" refers to a 5 to 18 membered all-carbon polycyclic group, comprising two or more cyclic structures sharing an adjacent pair of carbon atoms with other rings, wherein one or more rings may contain one or more double bonds, but none of the rings have a completely conjugated π-electron aromatic system. Preferably 6 to 12 membered, more preferably 7 to 10 membered. According to the number of rings constituted, it may be classified into a bicyclic, tricyclic, tetracyclic or polycyclic fused cycloalkyl, preferably a bicyclic or tricyclic ring, more preferably a 5-membered/5-membered or 5-membered/6-membered bicycloalkyl. Non-limiting examples of "fused cycloalkyl" include, but are not limited to, bicyclo[3.1.0]hexyl, bicyclo[3.2.0]hept-1-enyl, bicyclo[3.2.0]heptyl, decalinyl or tetradecahydrophenanthrenyl.

"Bridged cycloalkyl" refers to a 5 to 18 membered all-carbon polycyclic group, comprising two or more cyclic structures sharing two disconnected carbon atoms with each other, and one or more rings may contain one or more double bonds, however, none of the rings have a completely conjugated π-electron aromatic system. Preferably 6 to 12 membered, more preferably 7 to 10 membered. It is preferably 6 to 14 membered, more preferably 7 to 10 membered. According to the number of rings constituted, it may be classified into a bicyclic, tricyclic, tetracyclic or polycyclic bridged cycloalkyl, preferably a bicyclic, a tricyclic or a tetracyclic ring, and more preferably a bicyclic or a tricyclic ring. Non-limiting examples of "bridged cycloalkyl" include, but are not limited to: (1s,4s)-bicyclo[2.2.1]heptyl, bicyclo[3.2.1]octyl, (1s,5s)-dicyclo[3.3.1]nonyl, bicyclo[2.2.2]octyl, (1r,5r)-bicyclo[3.3.2]decyl.

Said cycloalkyl may be fused to an aryl, heteroaryl or heterocyclyl, wherein the ring attached to the parent structure is cycloalkyl, non-limiting examples include indanyl, tetrahydronaphthalenyl, benzocycloheptyl and the like. The cycloalkyl can be optionally substituted or unsubstituted.

"Heterocyclyl", "heterocycle" or "heterocyclic" are used interchangeably herein to refer to a non-aromatic heterocyclic group wherein one or more of the ring-forming atoms are heteroatoms, such as oxygen, nitrogen, sulfur atoms, etc., including monocyclic, fused, bridged, and spiro rings. It preferably has a 5- to 7-membered monocyclic ring or a 7- to 10-membered bicyclic- or tricyclic ring which may contain 1, 2 or 3 atoms selected from nitrogen, oxygen and/or sulfur. Examples of "heterocyclyl" include, but are not limited to morpholinyl, thiomorpholinyl, tetrahydropyranyl, 1,1-dioxo-thiomorpholinyl, piperidinyl, 2-oxo-piperidinyl, pyrrolidinyl, 2-oxo-pyrrolidinyl, piperazin-2-one, 8-oxa-3-aza-bicyclo[3.2.1]octyl and piperazinyl. The heterocyclyl may be substituted or unsubstituted.

"Spiroheterocyclyl" refers to a 5 to 18 membered polycyclic group with two or more cyclic structures and single rings share one common atom with each other, wherein the said ring may contains one or more double bonds, but none of the rings have a completely conjugated π-electron aromatic system, wherein one or more ring atoms are selected from the heteroatoms of nitrogen, oxygen or $S(O)_n$ (wherein n is 0, 1 or 2) and the remaining ring atoms are carbon. It is preferably 6- to 14-membered, more preferably 7- to 10-membered. The spiroheterocyclyl is classified into a monospiroheterocyclyl, a dispiroheterocyclyl or a polyspiroheterocyclyl according to the number of shared spiro atoms between the rings, and is preferably a monospiroheterocyclyl or a dispiroheterocyclyl. More preferably, it is 3-membered/6-membered, 4-membered/4-membered, 4-membered/5-membered, 4-membered/6-membered, 5-membered/5-membered or 5-membered/6-membered monospiroheterocyclyl. Wherein "a-membered/b-membered monospiroheterocyclyl" refers to a spiroheterocyclyl in which a-membered monocyclic ring and b-membered monocyclic ring share one atom with each other. Non-limiting examples of "spiroheterocyclyl" include, but are not limited to 1,7-dioxaspiro[4.5]decyl, 2-oxa-7-azaspiro[4.4] decyl, 7-oxaspiro[3.5]nonyl and 5-oxaspiro[2.4]heptyl.

"Fused heterocyclyl" refers to an all-carbon polycyclic group comprising two or more cyclic structures that share an adjacent pair of atoms with each other, and one or more rings may contain one or more double bonds, but none of the rings have completely conjugated π-electron aromatic system in which one or more ring atoms are selected from the heteroatoms of nitrogen, oxygen or $S(O)_n$ (wherein n is 0, 1 or 2), and the remaining ring atoms are carbon. Preferably 6- to 14-membered, more preferably 7- to 10-membered. Depending on the number of rings constituted, it may be classified into bicyclic, tricyclic, tetracyclic or polycyclic fused heterocyclyl, preferably a bicyclic or tricyclic ring, more preferably a 5-membered/5-membered or 5-membered/6-membered bicyclic fused heterocyclyl. Non-limiting examples of "fused heterocyclyl" include, but are not limited to octahydropyrrolo[3,4-c]pyrrolyl, octahydro-1H-isoindolyl, 3-azabicyclo[3.1.0]hexyl, octahydrobenzo[b][1,4]dioxine.

"Bridged heterocyclyl" refers to a 5 to 18 membered polycyclic group comprising two or more cyclic structures sharing two disconnected atoms with each other, and one or more rings may contain one or more double bonds, however, none of the rings have a completely conjugated π-electron aromatic system, in which one or more ring atoms are selected from the heteroatoms of nitrogen, oxygen or $S(O)_n$ (wherein n is 0, 1 or 2), and the remaining ring atoms are carbon. It is preferably 6 to 14 membered, more preferably 7 to 10 membered. Depending on the number of rings constituted, it may be classified into a bicyclic, tricyclic, tetracyclic or polycyclic bridged heterocyclyl, preferably a bicyclic, a tricyclic or a tetracyclic ring, and more preferably a bicyclic or a tricyclic ring. Non-limiting examples of "fused heterocyclic groups" include, but are not limited to 2-azabicyclo[2.2.1]heptyl, 2-azabicyclo[2.2.2]octyl and 2-azabicyclo[3.3.2]decyl. The heterocyclyl ring may be fused to an aryl, heteroaryl or cycloalkyl ring, wherein the ring attached to the parent structure is heterocyclyl. The heterocyclyl may be optionally substituted or unsubstituted.

"Aryl" refers to a carbocyclic aromatic system containing one or two rings wherein the rings may be fused to each other. The term "aryl" includes aromatic groups such as phenyl, naphthyl, tetrahydronaphthyl. Preferably, the aryl is a $C_6$-$C_{10}$ aryl, more preferably the aryl is a phenyl and a naphthyl, and most preferably a phenyl. The aryl may be substituted or unsubstituted. The "aryl" may be fused to heteroaryl, heterocyclyl or cycloalkyl, wherein the ring attached to the parent structure is the aryl ring, non-limiting examples include, but are not limited to:

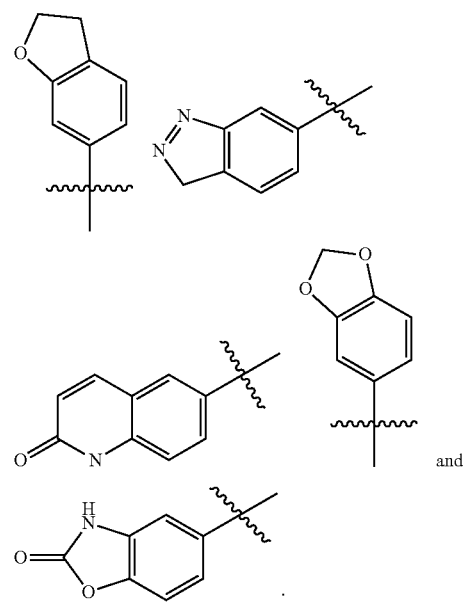

and

"Heteroaryl" refers to an aromatic 5- to 6-membered monocyclic ring or 9- to 10-membered bicyclic ring which may contain 1 to 4 atoms selected from nitrogen, oxygen and/or sulfur. Examples of "heteroaryl" include, but are not limited to furyl, pyridyl, 2-oxo-1,2-dihydropyridyl, pyridazinyl, pyrimidinyl, pyrazinyl, thienyl, isoxazolyl, oxazolyl, oxadiazolyl, imidazolyl, pyrrolyl, pyrazolyl, triazolyl, tetrazolyl, thiazolyl, isothiazolyl, 1,2,3-thiadiazolyl, benzodioxolyl, benzimidazolyl, indolyl, isoindolyl, 1,3-dioxoisoindolyl, quinolyl, indazolyl, benzoisothiazolyl, benzoxazolyl, and benzoisoxazolyl. Heteroaryl may be substituted or unsubstituted. The heteroaryl ring may be fused to an aryl, heterocyclyl or cycloalkyl ring, wherein the ring attached to the parent structure is the heteroaryl ring, non-limiting examples include, but are not limited to:

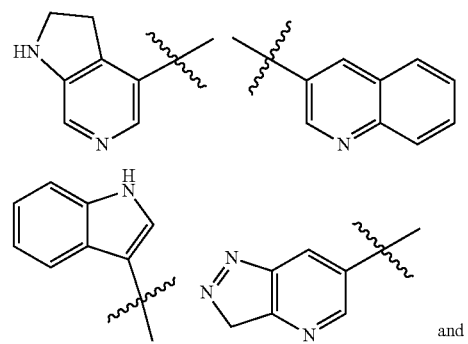

and

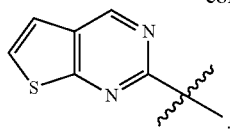

"Alkoxy" refers to a group of alkyl-O—. Wherein the alkyl group is as defined herein. The alkoxy of $C_1$-$C_6$ is preferred. Examples thereof include, but are not limited to methoxy, ethoxy, n-propoxy, isopropoxy, n-butoxy, isobutoxy, tert-butoxy and the like.

"Hydroxy" refers to an —OH group.

"Halogen" refers to fluorine, chlorine, bromine and iodine, preferably chlorine, bromine and iodine.

"Amino" refers to —$NH_2$.

"Cyano" refers to —CN.

"Nitro" refers to —$NO_2$.

"Benzyl" refers to —$CH_2$-phenyl.

"Carboxy" refers to —C(O)OH.

"carboxylatyl" refers to —C(O)O(alkyl) or (cycloalkyl), wherein alkyl, cycloalkyl are as defined above.

"Boc" refers to tert-butoxycarbonyl.

"N protecting group" refers to a molecule containing two or more functional groups. In order to protect —$NH_2$ or —NH— from reaction in organic synthesis, a certain reagent is usually used, and the protecting group is removed after the reaction is completed. N protecting groups include, but are not limited to tert-butoxycarbonyl, benzyloxycarbonyl, formyl or trifluoroacetyl.

"Substituted" refers to one or more hydrogen in the group, preferably up to 5, more preferably 1 to 3 hydrogen, independently of each other, substituted by a corresponding number of substituents. It goes without saying that the substituents are only in their possible chemical positions, and those skilled in the art will be able to determine (by experiment or theory) substitution that may or may not be possible without undue effort. For example, the combination of an amino or hydroxyl group having free hydrogen(s) with a carbon atom having an unsaturated (e.g., olefinic) bond may be unstable.

As used herein, "substitute" or "substituted", unless otherwise indicated, refers to that the group may be substituted by one or more groups selected from the group consisting of alkyl, alkenyl, alkynyl, alkoxy, alkylthio, alkylamino, halogen, sulfhydryl, hydroxy, nitro, cyano, cycloalkyl, heterocyclyl, aryl, heteroaryl, cycloalkoxy, heterocycloalkoxy, cycloalkylthio, heterocycloalkylthio, amino, haloalkyl, hydroxyalkyl, carboxyl, carboxylic ester group, =O, —$NR^7R^8$, —$C(O)NR^7R^8$, —$C(O)R^9$, —$C(O)OR^9$ or —$NR^7C(O)R^8$.

$R^7$, $R^8$ and $R^9$ are each independently selected from hydrogen, alkyl, cycloalkyl, heterocyclyl, aryl or heteroaryl, wherein the alkyl, cycloalkyl, heterocyclyl, aryl or heteroaryl is optionally further substituted by one or more substituents selected from the group consisting of hydroxyl, halogen, nitro, cyano, alkyl, alkoxy, cycloalkyl, heterocyclyl, aryl, heteroaryl, —$NR^{10}R^{11}$, —$C(O)NR^{10}R^{11}$, —$C(O)R^{12}$, —$C(O)OR^{12}$ or —$NR^{10}C(O)R^{11}$;

Alternatively, $R^7$ and $R^8$ together with the N atom to which they are attached form a 4 to 8 membered heterocyclyl, wherein the 4 to 8 membered heterocyclic ring contains one or more N, O, $S(O)_n$ atoms, and the 4 to 8 membered heterocyclic ring is further substituted by one or more substituents selected from the group consisting of hydroxy, halogen, nitro, cyano, alkyl, alkoxy, cycloalkyl, heterocyclyl, aryl, heteroaryl, =O, —$NR^{10}R^{11}$, —$C(O)NR^{10}R^{11}$, —$C(O)R^{12}$, —$C(O)OR^{12}$ and —$NR^{10}C(O)R^{11}$;

$R^{10}$, $R^{11}$ and $R^{12}$ are each independently selected from hydrogen, alkyl, cycloalkyl, heterocyclyl, aryl or heteroaryl, wherein the alkyl, cycloalkyl, heterocyclyl, aryl or heteroaryl are optionally further substituted by one or more substituents selected from the group consisting of hydroxy, halogen, nitro, cyano, alkyl, alkoxy, cycloalkyl, heterocyclyl, aryl, heteroaryl, carboxylic acid or carboxylate.

"Pharmaceutically acceptable salt" refers to certain salts of the above compounds which retain their original biological activity and are suitable for pharmaceutical use. The pharmaceutically acceptable salt of the compound represented by formula (I) may be a metal salt, an amine salt formed with a suitable acid, the metal salt is preferably an alkali metal or an alkaline earth metal salt, and a suitable acid including an inorganic acid and an organic acid, such as acetic acid, benzenesulfonic acid, benzoic acid, camphorsulfonic acid, citric acid, ethanesulfonic acid, fumaric acid, gluconic acid, glutamic acid, hydrobromic acid, hydrochloric acid, isethionic acid, lactic acid, malic acid, maleic acid, mandelic acid, methanesulfonic acid, nitric acid, phosphoric acid, succinic acid, sulfuric acid, tartaric acid, p-toluenesulfonic acid, and the like. Particularly preferred are hydrochloric acid, hydrobromic acid, phosphoric acid and sulfuric acid, and most preferred is the hydrochloride salt.

"Pharmaceutical composition" refers to a mixture comprising one or more of the compounds described herein or a physiologically pharmaceutically acceptable salt or a prodrug thereof and other chemical components, as well as other components such as physiologically pharmaceutically acceptable carriers and excipients. The purpose of the pharmaceutical composition is to promote the administration to the organism, which facilitates the absorption of the active ingredient and thereby exerts biological activity.

Method for Synthesizing the Compound of the Present Invention

In order to accomplish the object of the present invention, the following technical solutions are adopted:

The preparation method of the compound of formula (I) or a salt thereof of the present invention comprises the following steps:

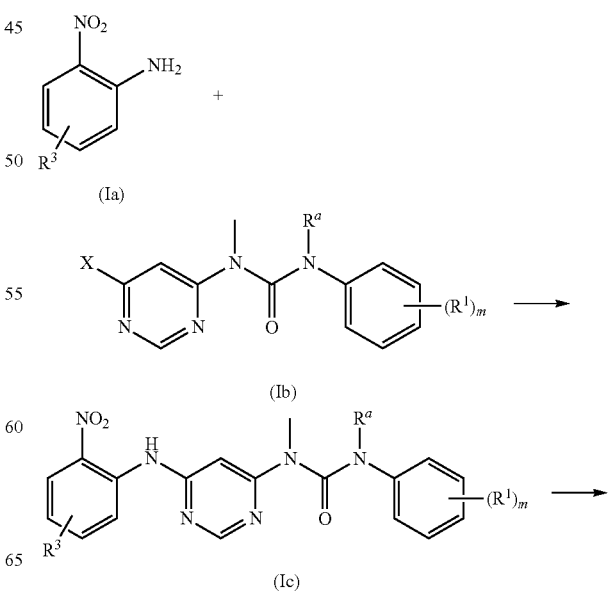

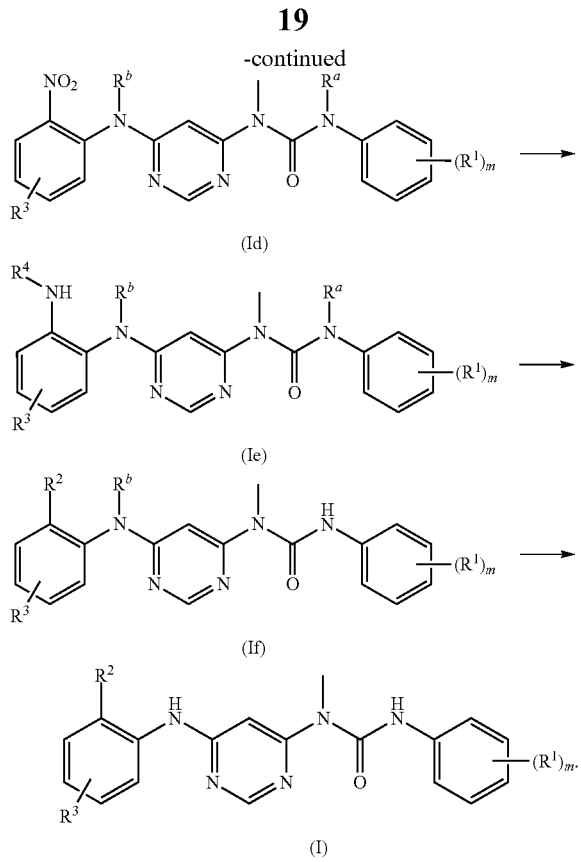

The compound of formula (Ia) and the compound of formula (Ib) are subjected to a Buchwald reaction, preferably in the presence of 4,5-bisdiphenylphosphino-9,9-dimethylxanthene, palladium catalyzed tris(dibenzalacetone)dipalladium and cesium carbonate, to obtain a compound of formula (Ic); the amino of the compound of formula (Ic) is protected, preferably with di-tert-butyl dicarbonate, to obtain an $R^b$-protected compound of formula (Id); the nitro of the compound of formula (Id) is reduced under hydrogen, optionally further alkylated to obtain a compound of formula (Ie); reacting the compound of formula (Ie) with an acyl halide compound, preferably X—C(O)CR$^5$=CHR$^6$ or X—C(O)C≡CR$^5$, and the amino protecting group IV is further removed to obtain a compound of formula (If); and the amino protecting group $R^b$ of the compound of formula (If) is further removed to obtain a compound of formula (I); wherein:

$R^a$ and $R^b$ are each independently selected from N protecting groups, preferably phenylsulfonyl, benzyloxycarbonyl, formyl, trifluoroacetyl and tert-butoxycarbonyl; more preferably phenylsulfonyl and tert-butoxycarbonyl;

X is halogen;

in the reaction scheme, when $R^3$ contains —NH$_2$ or —NH—, —NH$_2$ or —NH— may optionally be protected by an N protecting group; the N protecting group is preferably —C(O)R$^9$, more preferably a tert-butoxycarbonyl group;

$R^1$ to $R^6$, $R^9$ and m are as defined in formula (I).

EMBODIMENT

Figure 1:
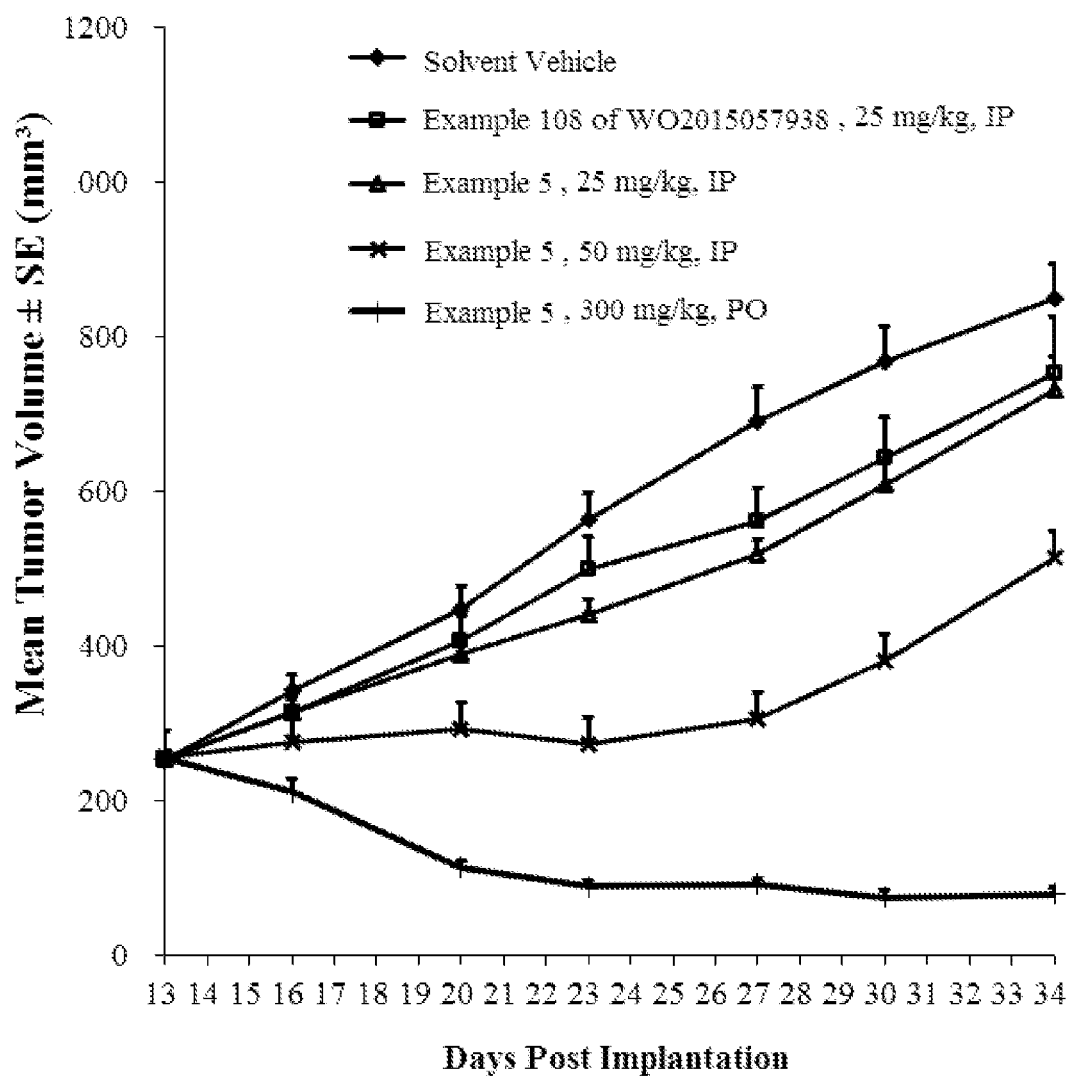
FIG. 1 is a graph showing changes in mean tumor volume of xenografts of hepatocellular carcinoma tumor cell Huh7 tumor-bearing BALB/c nude mice by the compound of Example 108 of WO2015057938 and the compound of Example 5 of the present invention in Test Example 3.

The present invention is further described in the following examples, but these examples are not intended to limit the scope of the present invention.

EXAMPLE

The preparation of representative compounds of formula (I) and related data about structural identification are provided by the examples. It is to be understood that the following examples are intended to illustrate and not to limit the present invention. The $^1$H NMR spectrum was determined using a Bruker instrument (400 MHz) and the chemical shift is expressed in ppm. The internal standard of tetramethylsilane (0.00 ppm) was used. $^1$H NMR representation: s=singlet, d=doublet, t=triplet, m=multiplet, br=broadened, dd=doublet of doublet, dt=doublet of triplet. If a coupling constant is provided, its unit is Hz.

Mass spectrometry was measured by LC/MS tester, and the ionization method was ESI or APCI.

Yantai Huanghai HSGF254 or Qingdao GF254 silica gel plate is used as the silica gel plate of thin layer chromatography. The dimension of the silica gel plate used in thin layer chromatography (TLC) are 0.15 mm to 0.2 mm, and the dimension of the silica gel plate used for the separation and purification of products by thin layer chromatography are 0.4 mm to 0.5 mm.

Column chromatography generally uses Yantai Huanghai silica gel of 200300 mesh as carrier.

In the following examples, all temperatures are in degrees Celsius unless otherwise indicated, and the various starting materials and reagents are either commercially available or synthesized according to known methods unless otherwise indicated, and the commercially available materials and reagents are used directly without further purification. Unless otherwise indicated, commercially available manufacturers, including but not limited to Aldrich Chemical Company, ABCR GmbH & Co. KG, Acros Organics, Guangzan Chemical Technology Co., Ltd. and Jingyan Chemical Technology Co., Ltd., etc.

CD$_3$OD: deuterated methanol.

CDCl$_3$: deuterated chloroform.

DMSO-d$_6$: deuterated dimethyl sulfoxide.

The argon atmosphere refers to that the reaction flask is equipped with an argon balloon having a volume of about 1 L.

Unless otherwise stated, the solution in the reaction used in examples refers to an aqueous solution.

The compounds are purified using a silica gel column chromatography eluent system and thin layer chromatography, wherein the eluent system is selected from: A: petroleum ether and ethyl acetate system; B: dichloromethane and methanol system; The volume ratio of solvents varies depending on the polarity of the compounds, and a small amount of an acidic or alkaline reagents such as acetic acid or triethylamine may also be added.

Example 1
N-(2-((6-(3-(2,6-Dichloro-3,5-dimethoxyphenyl)-1-methylureido)pyrimidin-4-yl)amino)-5-(2,7-diazaspiro[3.5]nonan-2-yl)phenyl)acrylamide
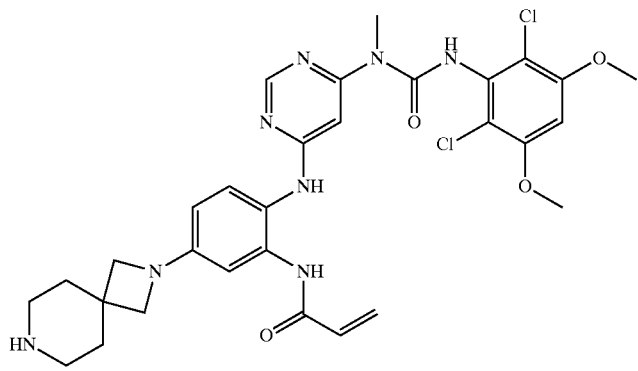
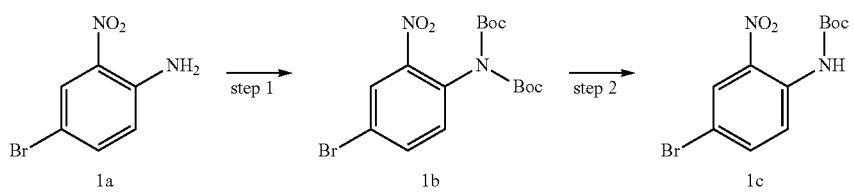
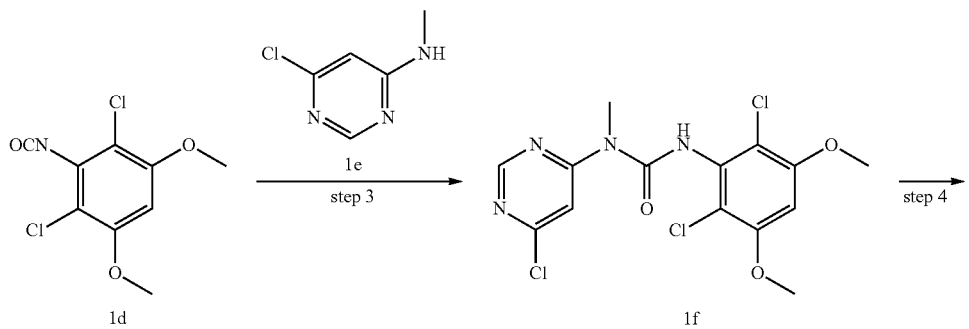
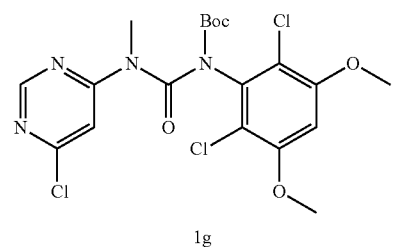

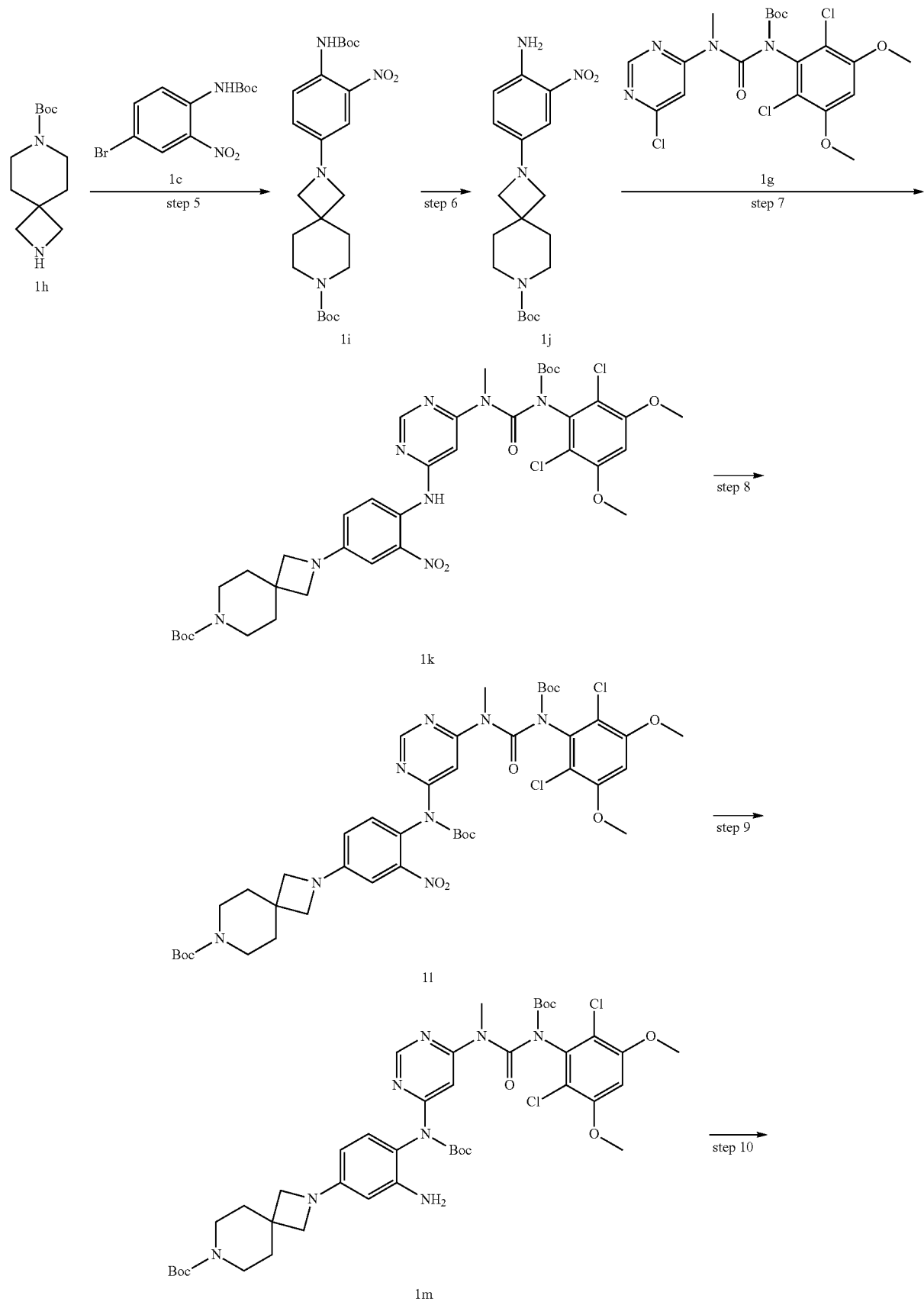

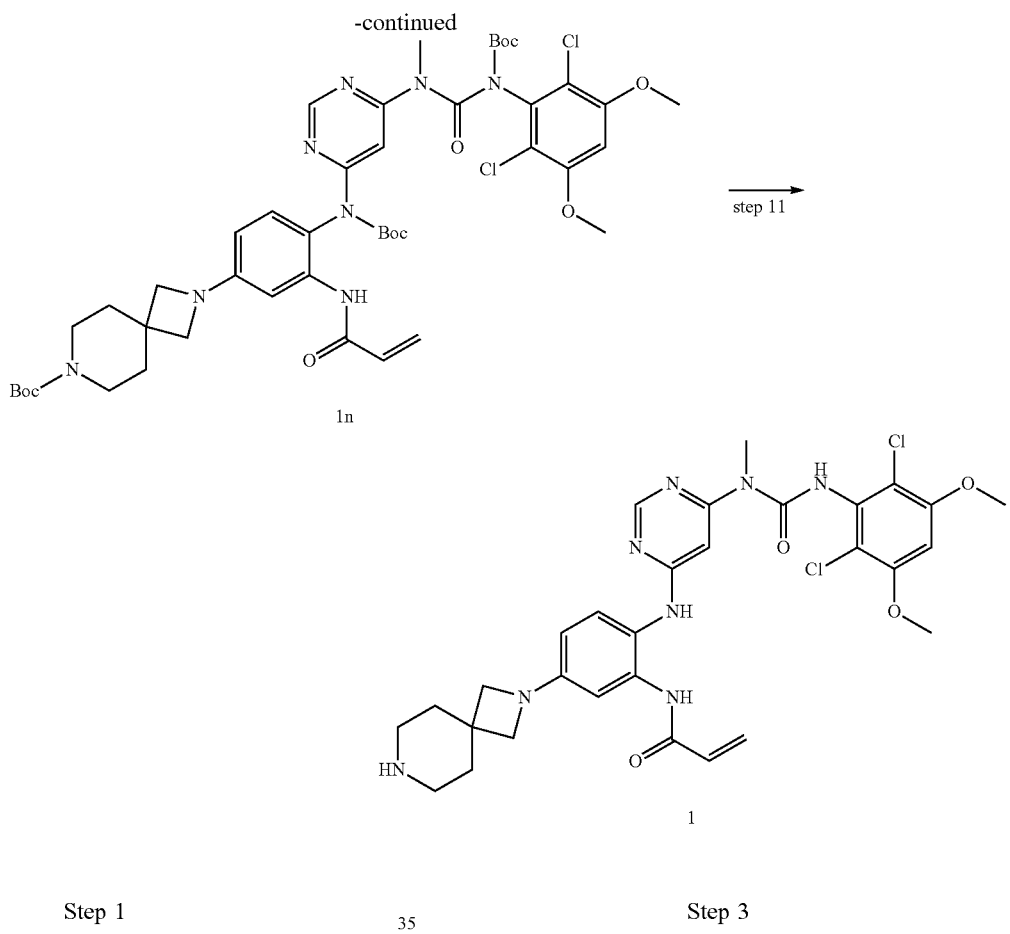

Step 1

Tert-butyl N-(4-bromo-2-nitro-phenyl)-N-tert-butoxycarbonyl-carbamate

4-Bromo-2-nitroaniline 1a (7.50 g, 34.56 mmol) was dissolved in 90 mL of tetrahydrofuran, the solution was added with di-tert-butyl dicarbonate (15.08 g, 69.12 mmol) and 4-dimethylaminopyridine (200 mg, 1.64 mmol), heated to 80° C. and reacted for 2 hours. The reaction solution was concentrated under reduced pressure, the resulting residue was purified by silica gel column chromatography (eluent: A system) to obtain tert-butyl N-(4-bromo-2-nitro-phenyl)-N-tert-butoxycarbonyl-carbamate 1b (12.6 g, yellow solid), yield: 87.4%.

MS m/z (ESI): 361.0 [M+1-56]

Step 2

Tert-butyl (4-bromo-2-nitrophenyl)carbamate

Tert-butyl N-(4-bromo-2-nitro-phenyl)-N-tert-butoxycarbonyl-carbamate 1b (7.12 g, 17.1 mmol) and potassium carbonate (7.08 g, 51.2 mmol) were dissolved in 140 mL of acetonitrile, the solution was heated to 35° C. and reacted for 1.5 hours. The reaction solution was filtered, the filtrate was concentrated under reduced pressure, the resulting residue was purified by silica gel column chromatography (eluent: A system) to obtain tert-butyl (4-bromo-2-nitrophenyl)carbamate 1c (4.49 g, bright yellow solid), yield: 82.8%.

MS m/z (ESI): 216.8 [M+1-100]

Step 3

3-(2,6-Dichloro-3,5-dimethoxyphenyl)-1-(6-chloropyrimidin-4-yl)-1-methylurea

6-Chloro-N-methylpyrimidin-4-amine 1e (300 mg, 2.09 mmol) was dissolved in 10 mL of N,N-dimethylformamide, the solution was cooled to 0° C., added with 60% sodium hydride (167 mg, 4.18 mmol), and stirred at room temperature for 30 minutes. 2,4-dichloro-3-isocyanato-1,5-dimethoxy-4-methyl benzene 1d (674 mg, 2.72 mmol) was dissolved in 5 mL of N,N-dimethylformamide and added dropwise to the reaction solution, and reacted at room temperature for 0.5 hour. The reaction solution was added with 50 mL of water, and a white solid was precipitated. After filtration, the filter cake was recrystallized with ethyl acetate to obtain 3-(2,6-dichloro-3,5-dimethoxyphenyl)-1-(6-chloropyrimidin-4-yl)-1-methylurea 1f (710 mg, white solid), yield: 86.8%.

MS m/z (ESI): 392.8 [M+1]

Step 4

Tert-butyl (6-chloropyrimidin-4-yl)(methyl)carbamoyl-(2,6-dichloro-3,5-dimethoxyphenyl)carbamate 3-(2,6-Dichloro-3,5-dimethoxyphenyl)-1-(6-chloropyrimidin-4-yl)-1-methylurea 1f (1.20 g, 3.06 mmol) was dissolved in 20 mL of tetrahydrofuran, the solution was cooled to 0° C., added with di-tert-butyl dicarbonate (1.34 g, 6.13 mmol) and 4-dimethylaminopyridine (187 mg, 1.53 mmol), heated to 75° C. and refluxed for 1 hour. The reaction solution was concentrated under reduced pressure, and added with 30 mL of dichloromethane, washed with water (20 mL×2) and saturated sodium chloride solution (20 mL) successively, dried over anhydrous sodium sulfate, filtered, and concentrated under reduced pressure, the resulting residue was purified by silica gel column chromatography (eluent: A system) to obtain tert-butyl (6-chloropyrimidin-4-yl)(methyl)carbamoyl-(2,6-dichloro-3,5-dimethoxyphenyl)carbamate 1g (1.34 g, white solid), yield: 88.9%.

MS m/z (ESI): 492.8 [M+1]

Step 5

Tert-butyl 2-(4-((tert-butoxycarbonyl)amino)-3-nitrophenyl)-2,7-diazaspiro[3.5]nonane-7-carboxylate Tert-butyl 2,7-diazaspiro[3.5]nonane-7-carboxylate 1h (440 mg, 1.94 mmol), tert-butyl (4-bromo-2-nitrophenyl)carbamate 1c (616 mg, 1.94 mmol), 4,5-bis(diphenylphosphino)-9,9-dimethylxanthene (229 mg, 0.388 mmol), tris(dibenzylideneacetone)dipalladium (352 mg, 0.388 mmol) and cesium carbonate (1.90 g, 5.83 mmol) were dissolved in 15 mL of methylbenzene, the reaction mixture was reacted at 115° C. for 4 hours under argon atmosphere. The reaction solution was cooled to room temperature, filtered, and concentrated under reduced pressure, the resulting residue was purified by silica gel column chromatography (eluent: A system) to obtain tert-butyl 2-(4-((tert-butoxycarbonyl)amino)-3-nitrophenyl)-2,7-diazaspiro[3.5]nonane-7-carboxylate 1i (600 mg, red solid), yield: 66.7%.

MS m/z (ESI): 485.0 [M+23]

Step 6

Tert-butyl 2-(4-amino-3-nitrophenyl)-2,7-diazaspiro[3.5]nonane-7-carboxylate

Tert-butyl 2-(4-((tert-butoxycarbonyl)amino)-3-nitrophenyl)-2,7-diazaspiro[3.5]nonane-7-carboxylate 1i (600 mg, 1.30 mmol) and potassium hydroxide (218 mg, 3.89 mmol) were dissolved in 10 mL of a mixed solution of water and ethanol (V/V=1/4), the solution was heated to reflux for 3 hours. The reaction solution was concentrated under reduced pressure, 20 mL of ethyl acetate was added, layered, the aqueous phase was extracted with ethyl acetate (20 mL×2), the organic phases were combined and washed with water (20 mL×2), dried over anhydrous sodium sulfate, filtered, and concentrated under reduced pressure, the resulting residue was purified by silica gel column chromatography (eluent: A system) to obtain tert-butyl 2-(4-amino-3-nitrophenyl)-2,7-diazaspiro[3.5]nonane-7-carboxylate 1j (400 mg, red solid), yield: 85.1%.

MS m/z (ESI): 362.1 [M+1]

Step 7

Tert-butyl 2-(4-((6-(3-(tert-butoxycarbonyl)-3-(2,6-dichloro-3,5-dimethoxyphenyl)-1-methylureido)pyrimidin-4-yl)amino)-3-nitrophenyl)-2,7-diazaspiro[3.5]nonane-7-carboxylate Tert-butyl (6-chloropyrimidin-4-yl)(methyl)carbamoyl-(2,6-dichloro-3,5-dimethoxyphenyl)carbamate 1g (450 mg, 0.909 mmol), 2-(4-amino-3-nitrophenyl)-2,7-diazaspiro[3.5]nonane-7-carboxylate 1j (300 mg, 0.828 mmol), 4,5-bis(diphenylphosphino)-9,9-dimethylxanthene (96 mg, 0.165 mmol), tris(dibenzylideneacetone)dipalladium (75 mg, 0.082 mmol) and cesium carbonate (810 mg, 2.40 mmol) were dissolved in 15 mL of toluene, the reaction mixture was reacted at 110° C. for 4 hours. The reaction solution was cooled to room temperature, filtered, and concentrated under reduced pressure, the resulting residue was purified by silica gel column chromatography (eluent: A system) to obtain tert-butyl 2-(4-((6-(3-(tert-butoxycarbonyl)-3-(2,6-dichloro-3,5-dimethoxyphenyl)-1-methylureido)pyrimidin-4-yl)amino)-3-nitrophenyl)-2,7-diazaspiro[3.5]nonane-7-carboxylate 1k (427 mg, red solid), yield: 63.3%.

$^1$H NMR (400 MHz, CDCl$_3$) δ 9.15 (s, 1H), 8.59 (s, 1H), 8.18 (d, J=8.4 Hz, 1H), 7.42 (s, 1H), 7.11 (d, J=6.4 Hz, 1H), 6.75-6.71 (m, 1H), 6.59 (s, 1H), 3.93 (s, 6H), 3.70 (s, 4H), 3.63 (s, 2H), 3.46-3.36 (m, 4H), 1.82-1.76 (m, 4H), 1.49 (s, 9H), 1.41 (s, 9H).

Step 8

Tert-butyl 2-(4-((tert-butoxycarbonyl)(6-(3-(tert-butoxycarbonyl)-3-(2,6-dichloro-3,5-dimethoxyphenyl)-1-)methylurea)pyrimidin-4-yl)amino)-3-nitrophenyl)-2,7-diazaspiro[3.5]nonane-7-carboxylate Tert-butyl 2-(4-((6-(3-(tert-butoxycarbonyl)-3-(2,6-dichloro-3,5-dimethoxyphenyl)-1-methylureido)pyrimidin-4-yl)amino)-3-nitrophenyl)-2,7-diazaspiro[3.5]nonane-7-carboxylate 1k (500 mg, 0.611 mmol) was dissolved in 10 mL of tetrahydrofuran, the solution was cooled to 0° C., added with di-tert-butyl dicarbonate (200 mg, 0.917 mmol) and 4-dimethylaminopyridine (37.3 mg, 0.306 mmol), and heated to reflux for 3 hours. The reaction solution was concentrated under reduced pressure and the resulting residue was purified by silica gel column chromatography (eluent: A system) to obtain tert-butyl 2-(4-((tert-butoxycarbonyl)(6-(3-(tert-butoxycarbonyl)-3-(2,6-dichloro-3,5-dimethoxyphenyl)-1-)methylurea)pyrimidin-4-yl)amino)-3-nitrophenyl)-2,7-diazaspiro[3.5]nonane-7-carboxylate 1l (500 mg, yellow solid), yield: 89.1%.

Step 9

Tert-butyl 2-(3-amino-4-((tert-butoxycarbonyl)(6-(3-(tert-butoxycarbonyl)-3-(2,6-dichloro-3,5-dimethoxyphenyl)-1-methylureido)pyrimidin-4-yl)amino)phenyl)-2,7-diazaspiro[3.5]nonane-7-carboxylate Tert-butyl 2-(4-((tert-butoxycarbonyl)(6-(3-(tert-butoxycarbonyl)-3-(2,6-dichloro-3,5-dimethoxyphenyl)-1-)methylurea)pyrimidin-4-yl)amino)-3-nitrophenyl)-2,7-diazaspiro[3.5]nonane-7-carboxylate 1l (500 mg, 0.545 mmol) was dissolved in 10 mL of methanol, the solution was added with Raney nickel (200 mg) was added and reacted under the protection of hydrogen for 12 hours at room temperature. The reaction solution was concentrated under reduced pressure and the resulting residue was purified by silica gel column chromatography (eluent: A system) to obtain tert-butyl 2-(3-amino-4-((tert-butoxycarbonyl)(6-(3-(tert-butoxycarbonyl)-3-(2,6-dichloro-3,5-dimethoxyphenyl)-1-methylureido)pyrimidin-4-yl)amino)phenyl)-2,7-diazaspiro[3.5]nonane-7-carboxylate 1m (300 mg, red solid), yield: 62.0%.

$^1$H NMR (400 MHz, CDCl$_3$) δ 8.66 (s, 1H), 8.21 (s, 1H), 6.81 (d, J=8.4 Hz, 1H), 6.59 (s, 1H), 5.9-5.85 (m, 1H), 5.84-5.79 (m, 1H), 3.94 (s, 6H), 3.63 (s, 3H), 3.6 (s, 4H), 3.43-3.32 (m, 4H), 1.82-1.72 (m, 4H), 1.46 (s, 9H), 1.42 (s, 9H), 1.41 (s, 9H).

Step 10

Tert-butyl 2-(3-acrylamido-4-((tert-butoxycarbonyl) (6-(3-(tert-butoxycarbonyl)-3-(2,6-dichloro-3,5-dimethoxyphenyl)-1-methylureido)pyrimidin-4-yl) amino)phenyl)-2,7-diazaspiro[3.5]nonane-7-carboxylate Tert-butyl 2-(3-amino-4-((tert-butoxycarbonyl)(6-(3-(tert-butoxycarbonyl)-3-(2,6-dichloro-3,5-dimethoxyphenyl)-1-methylureido)pyrimidin-4-yl)amino)phenyl)-2,7-diazaspiro[3.5]nonane-7-carboxylate 1m (200 mg, 0.225 mmol) was dissolved in 10 mL of dichloromethane, the solution was added with N,N-diisopropylethylamine (87 mg, 0.676 mmol) and acryloyl chloride (22 mg, 0.248 mmol) under an ice bath, and reacted at room temperature for 0.5 hours. The reaction solution was concentrated under reduced pressure and the resulting residue was purified by silica gel column chromatography (eluent: A system) to obtain tert-butyl 2-(3-acrylamido-4-((tert-butoxycarbonyl) (6-(3-(tert-butoxycarbonyl)-3-(2,6-dichloro-3,5-dimethoxyphenyl)-1-methylureido)pyrimidin-4-yl)amino)phenyl)-2,7-diazaspiro[3.5]nonane-7-carboxylate in (200 mg, pale yellow solid), yield: 94.3%.

Step 11

N-(2-((6-(3-(2,6-Dichloro-3,5-dimethoxyphenyl)-1-methylureido)pyrimidin-4-yl)amino)-5-(2,7-diazaspiro[3.5]nonan-2-yl)phenyl)acrylamide Tert-butyl 2-(3-acrylamido-4-((tert-butoxycarbonyl)(6-(3-(tert-butoxycarbonyl)-3-(2,6-dichloro-3,5-dimethoxyphenyl)-1-methylureido)pyrimidin-4-yl)amino)phenyl)-2,7-diazaspiro[3.5]nonane-7-carboxylate in (200 mg, 0.84 mmol) was dissolved in 10 mL of dichloromethane, the solution was added with 5 mL of trifluoroacetic acid under an ice bath, reacted at room temperature for 12 hours under the protection of nitrogen. The reaction solution was concentrated under reduced pressure, 20 mL of mixed solution of dichloromethane and methanol (V/V=10/1) was added, washed with saturated sodium bicarbonate solution (10 mL), and the organic phase was dried over anhydrous sodium sulfate, filtered, concentrated under reduced pressure, and the resulting residue was purified by silica gel thin layer chromatography (eluent: B system) to obtain N-(2-((6-(3-(2,6-dichloro-3,5-dimethoxyphenyl)-1-methylureido)pyrimidin-4-yl)amino)-5-(2,7-diazaspiro[3.5]nonan-2-yl)phenyl)acrylamide 1 (80 mg, pale yellow solid), yield: 58.8%.

MS m/z (ESI): 640.8 [M+1]

$^1$H NMR (400 MHz, DMSO-$d_6$) δ 12.1 (s, 1H), 9.64 (s, 1H), 8.82 (s, 1H), 8.3 (s, 1H), 7.22 (d, J=8.4 Hz, 1H), 6.95-6.86 (m, 2H), 6.58-6.48 (m, 1H), 6.28 (d, J=8.0 Hz, 1H), 6.22 (d, J=8.8 Hz, 1H), 5.76 (s, 1H), 5.71 (d, J=10.4 Hz, 1H), 3.93 (s, 6H), 3.63 (s, 4H), 3.21 (s, 3H), 3.12-3.01 (m, 4H), 2.0-1.91 (m, 4H).

Example 2

N-(2-((6-(3-(2,6-Dichloro-3,5-dimethoxyphenyl)-1-methylureido)pyrimidin-4-yl)amino)-5-(4,7-diazaspiro[2.5]octan-7-yl)phenyl)acrylamide

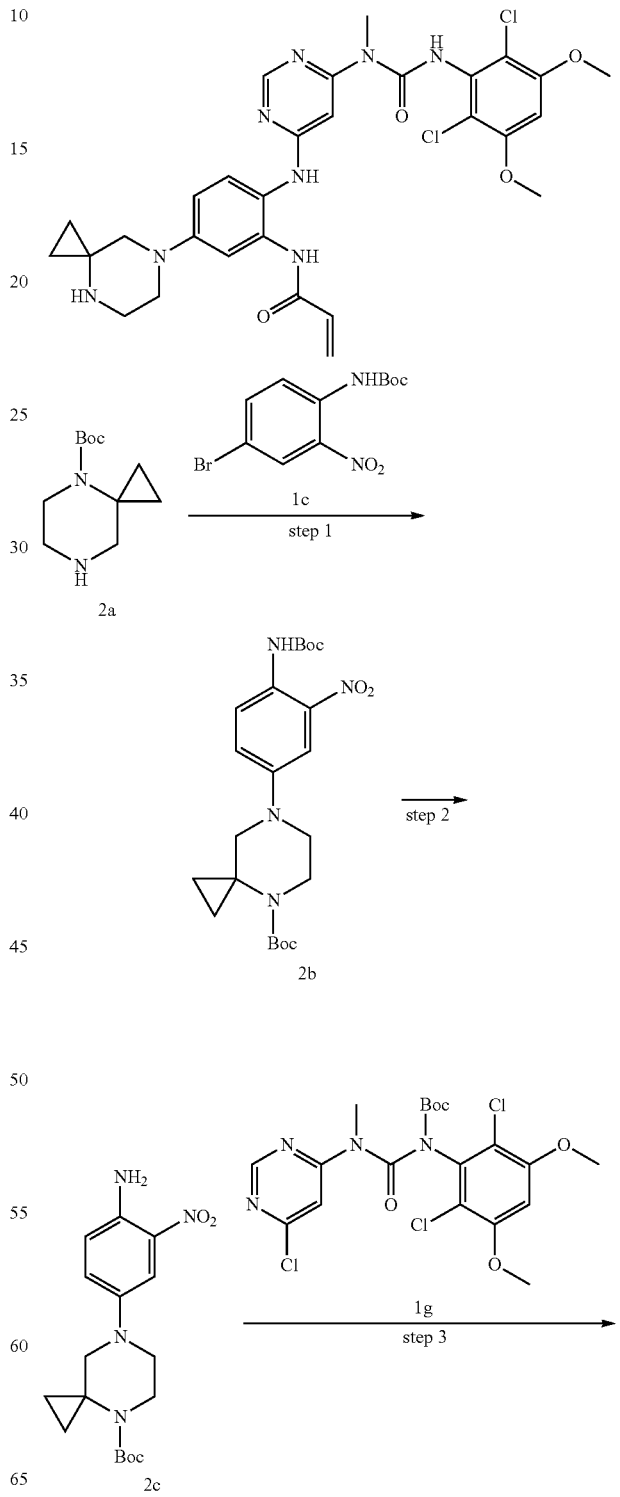

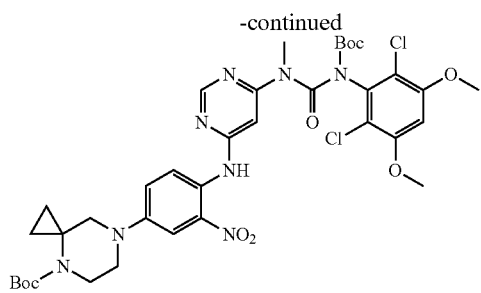

2d

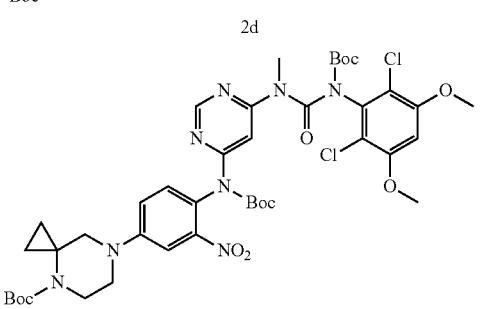

2e

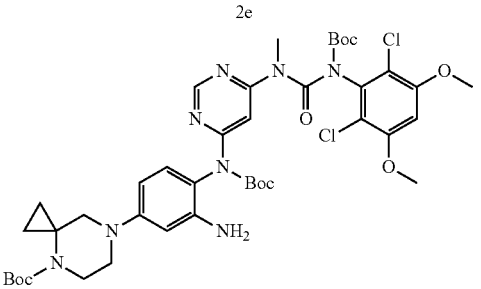

2f

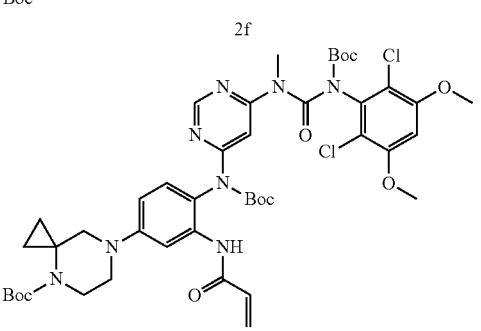

2g

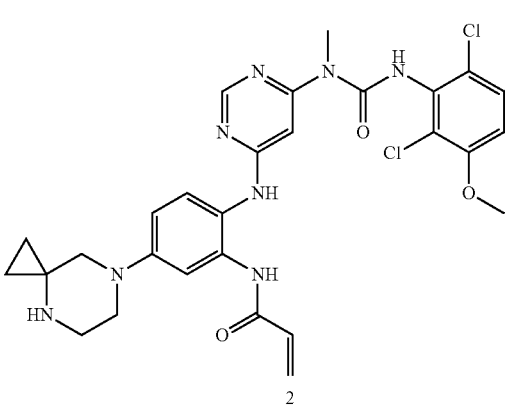

2

Step 1

Tert-butyl 7-(4-((tert-butoxycarbonyl)amino)-3-nitrophenyl)-4,7-diazaspiro[2.5]octane-4-carboxylate Tert-butyl 4,7-diazaspiro[2.5]octane-4-carboxylate 2a (803 mg, 3.78 mmol), tert-butyl (4-bromo-2-nitrophenyl)carbamate 1c (1.02 g, 3.15 mmol), 4,5-bis(diphenylphosphino)-9,9-dimethylxanthene (35 mg, 0.063 mmol), tris(dibenzylideneacetone)dipalladium (115 mg, 0.126 mmol) and cesium carbonate (3.08 g, 9.46 mmol) were dissolved in 30 mL of toluene and reacted at 110° C. for 6 hours under the protection of argon. The reaction solution was cooled to room temperature, filtered, and concentrated under reduced pressure and the resulting residue was purified by silica gel column chromatography (eluent: A system) to obtain tert-butyl 7-(4-((tert-butoxycarbonyl)amino)-3-nitrophenyl)-4,7-diazaspiro[2.5]octane-4-carboxylate 2b (240 mg, red solid), yield: 17.0%.

MS m/z (ESI): 348 [M−100]

Step 2

Tert-butyl 7-(4-amino-3-nitrophenyl)-4,7-diazaspiro[2.5]octane-4-carboxylate

Tert-butyl 7-(4-((tert-butoxycarbonyl)amino)-3-nitrophenyl)-4,7-diazaspiro[2.5]octane-4-carboxylate 2b (240 mg, 0.53 mmol) and potassium hydroxide (90 mg, 1.61 mmol) were dissolved in 8 mL of a mixed solution of water and ethanol (V/V=1/3), and heated to reflux for 6 hours. The reaction solution was concentrated under reduced pressure, 20 mL of ethyl acetate and 10 mL of water were added, seperated, the aqueous phase was extracted with ethyl acetate (10 mL×2), the organic phases were combined and washed with water (20 mL×2), dried over anhydrous sodium sulfate, filtered, and concentrated under reduced pressure to obtain crude product of tert-butyl 7-(4-amino-3-nitrophenyl)-4,7-diazaspiro[2.5]octane-4-carboxylate 2c (160 mg, red solid), yield: 86.6%.

$^1$H NMR (400 MHz, CDCl$_3$) δ 7.5 (s, 1H), 7.19-7.15 (m, 1H), 6.76 (d, J=8.4 Hz, 1H), 5.95-5.75 (m, 2H), 3.75-3.65 (m, 2H), 3.10-3.02 (m, 2H), 2.95-2.80 (m, 2H), 1.47 (s, 9H), 1.10-1.04 (m, 2H), 0.89-0.84 (m, 2H).

Step 3

Tert-butyl 7-(4-((6-(3-(tert-butoxycarbonyl)-3-(2,6-dichloro-3,5-dimethoxyphenyl)-1-methylureido)pyrimidin-4-yl)amino)-3-nitrophenyl)-4,7-diazaspiro[2.5]octane-4-carboxylate Tert-butyl (6-chloropyrimidin-4-yl)(methyl)carbamoyl-(2,6-dichloro-3,5-dimethoxyphenyl)carbamate 1g (248 mg, 0.51 mmol), tert-butyl 7-(4-amino-3-nitrophenyl)-4,7-diazaspiro[2.5]octane-4-carboxylate 2c (160 mg, 0.46 mmol), 4,5-bis(diphenylphosphino)-9,9-dimethylxanthene (53 mg, 0.092 mmol), tris(dibenzylideneacetone)dipalladium (42 mg, 0.046 mmol) and cesium carbonate (449 mg, 1.38 mmol) were dissolved in 10 mL of toluene and reacted at 110° C. for 4 hours. The reaction solution was cooled to room temperature, filtered, and concentrated under reduced pressure, the resulting residue was purified by silica gel column chromatography (eluent: A system) to obtain tert-butyl 7-(4-((6-(3-(tert-butoxycarbonyl)-3-(2,6-dichloro-3,5-dimethoxyphenyl)-1-methylureido)pyrimidin-4-yl)amino)-

3-nitrophenyl)-4,7-diazaspiro[2.5]octane-4-carboxylate 2d (262 mg, red solid), yield: 71.0%.

MS m/z (ESI): 803.8 [M+1]

Step 4

Tert-butyl 7-(4-((tert-butoxycarbonyl)(6-(3-(tert-butoxycarbonyl)-3-(2,6-dichloro-3,5-dimethoxyphenyl)-1-methylureido)pyrimidin-4-yl)amino)-3-nitrophenyl)-2,7-diazaspiro[2.5]octane-4-carboxylate Tert-butyl 7-(4-((6-(3-(tert-butoxycarbonyl)-3-(2,6-dichloro-3,5-dimethoxyphenyl)-1-methylureido)pyrimidin-4-yl)amino)-3-nitrophenyl)-4,7-diazaspiro[2.5]octane-4-carboxylate 2d (262 mg, 0.326 mmol) was dissolved in 10 mL of tetrahydrofuran, the solution was cooled to 0° C., added with di-tert-butyl dicarbonate (107 mg, 0.489 mmol) and 4-dimethylaminopyridine (20 mg, 0.163 mmol) were added, and t heated to reflux for 1 hour. The reaction solution was concentrated under reduced pressure and the resulting residue was purified by silica gel column chromatography (eluent: A system) to obtain tert-butyl 7-(4-((tert-butoxycarbonyl)(6-(3-(tert-butoxycarbonyl)-3-(2,6-dichloro-3,5-dimethoxyphenyl)-1-methylureido)pyrimidin-4-yl)amino)-3-nitrophenyl)-2,7-diazaspiro[2.5]octane-4-carboxylate 2e (260 mg, yellow solid), yield: 88.4%.

$^1$H NMR (400 MHz, CDCl$_3$) δ 8.55 (s, 1H), 8.44 (s, 1H), 7.62 (s, 1H), 7.22-7.05 (m, 2H), 6.59 (s, 1H), 3.94 (s, 6H), 3.78 (t, J=4.4 Hz, 2H), 3.66 (s, 3H), 3.33 (t, J=4.4 Hz, 2H), 3.12 (s, 2H), 1.48 (s, 9H), 1.44-1.38 (m, 18H), 1.14-1.09 (m, 2H), 0.96-0.89 (m, 2H).

Step 5

Tert-butyl 7-(3-amino-4-((tert-butoxycarbonyl)(6-(3-(tert-butoxycarbonyl)-3-(2,6-dichloro-3,5-dimethoxyphenyl)-1-methylureido)pyrimidin-4-yl)amino)phenyl)-4,7-diazaspiro[2.5]octane-4-carboxylate Tert-butyl 7-(4-((tert-butoxycarbonyl)(6-(3-(tert-butoxycarbonyl)-3-(2,6-dichloro-3,5-dimethoxyphenyl)-1-methylureido)pyrimidin-4-yl)amino)-3-nitrophenyl)-2,7-diazaspiro[2.5]octane-4-carboxylate 2e (260 mg, 0.288 mmol) was dissolved in 9 mL of a mixed solution of tetrahydrofuran and methanol (V/V=1/2), and Raney nickel (100 mg) was added, reacted for 6 hours at room temperature under the protection of hydrogen. The reaction solution was filtered, concentrated under reduced pressure and the resulting residue was purified by silica gel column chromatography (eluent: A system) to obtain tert-butyl 7-(3-amino-4-((tert-butoxycarbonyl)(6-(3-(tert-butoxycarbonyl)-3-(2,6-dichloro-3,5-dimethoxyphenyl)-1-methylureido)pyrimidin-4-yl)amino)phenyl)-4,7-diazaspiro[2.5]octane-4-carboxylate 2f (200 mg, yellow solid), yield: 79.7%.

Step 6

Tert-butyl 7-(3-acrylamido-4-((tert-butoxycarbonyl)(6-(3-(tert-butoxycarbonyl)-3-(2,6-dichloro-3,5-dimethoxyphenyl)-1-methylureido)pyrimidin-4-yl)amino)phenyl)-4,7-diazaspiro[2.5]octane-4-carboxylate Tert-butyl 7-(3-amino-4-((tert-butoxycarbonyl)(6-(3-(tert-butoxycarbonyl)-3-(2,6-dichloro-3,5-dimethoxyphenyl)-1-methylureido)pyrimidin-4-yl)amino)phenyl)-4,7-diazaspiro[2.5]octane-4-carboxylate 2f (200 mg, 0.229 mmol) was dissolved in 10 mL of dichloromethane, the solution was added with N,N-diisopropylethylamine (89 mg, 0.687 mmol) and acryloyl chloride (23 mg, 0.252 mmol) under an ice bath, and reacted for 0.5 hour at room temperature. The reaction solution was concentrated under reduced pressure and the resulting residue was purified by silica gel column chromatography (eluent: A system) to obtain tert-butyl 7-(3-acrylamido-4-((tert-butoxycarbonyl)(6-(3-(tert-butoxycarbonyl)-3-(2,6-dichloro-3,5-dimethoxyphenyl)-1-methylureido)pyrimidin-4-yl)amino)phenyl)-4,7-diazaspiro[2.5]octane-4-carboxylate 2g (180 mg, yellow solid), yield: 84.8%.

$^1$H NMR (400 MHz, CDCl$_3$) δ 8.64 (s, 1H), 8.28 (s, 1H), 8.11-8.0 (m, 1H), 7.07-7.02 (m, 1H), 6.59 (s, 1H), 6.37 (d, J=16.8 Hz, 1H), 6.25-6.15 (m, 1H), 5.75 (d, J=10.4 Hz, 1H), 3.95 (s, 6H), 3.85-3.77 (m, 2H), 3.64 (s, 3H), 3.35-3.25 (m, 2H), 3.12 (s, 2H), 1.48 (s, 9H), 1.42 (s, 9H), 1.34 (s, 9H), 1.14-1.06 (m, 2H), 0.97-0.91 (m, 2H).

Step 7

N-(2-((6-(3-(2,6-Dichloro-3,5-dimethoxyphenyl)-1-methylureido)pyrimidin-4-yl)amino)-5-(4,7-diazaspiro[2.5]octan-7-yl)phenyl)acrylamide Tert-butyl 7-(3-acrylamido-4-((tert-butoxycarbonyl)(6-(3-(tert-butoxycarbonyl)-3-(2,6-dichloro-3,5-dimethoxyphenyl)-1-methylureido)pyrimidin-4-yl)amino)phenyl)-4,7-diazaspiro[2.5]octane-4-carboxylate 2g (170 mg, 0.183 mmol) was dissolved in 6 mL of dichloromethane, the solution was added with 3 mL of trifluoroacetic acid under an ice bath, and reacted at room temperature for 12 hours under the protection of nitrogen. The reaction solution was concentrated under reduced pressure, 20 mL of a mixed solution of dichloromethane and methanol (V/V=10/1) was added, washed with saturated sodium bicarbonate solution (10 mL), and the organic phase was concentrated under reduced pressure, and the resulting residue was purified by silica gel thin layer chromatography (eluent: B system) to obtain N-(2-((6-(3-(2,6-dichloro-3,5-dimethoxyphenyl)-1-methylureido)pyrimidin-4-yl)amino)-5-(4,7-diazaspiro[2.5]octan-7-yl)phenyl)acrylamide 2 (40 mg, pale yellow solid), yield: 34.8%. MS m/z (ESI): 626.9 [M+1]

$^1$H NMR (400 MHz, DMSO-d$_6$) δ 12.09 (s, 1H), 9.84 (s, 1H), 9.01 (s, 1H), 8.32 (s, 1H), 7.46-7.31 (m, 2H), 6.89 (s, 1H), 6.85 (d, J=8.8 Hz, 1H), 6.63-6.48 (m, 1H), 6.39-6.13 (m, 2H), 5.73 (d, J=9.6 Hz, 1H), 3.93 (s, 6H), 3.29-3.11 (m, 9H), 1.13-0.99 (m, 2H), 0.97-0.78 (m, 2H).

Example 3

N-(2-((6-(3-(2,6-Dichloro-3,5-dimethoxyphenyl)-1-methylureido)pyrimidin-4-yl)amino)-5-(2,8-diazaspiro[4.5]decan-2-yl)phenyl)acrylamide

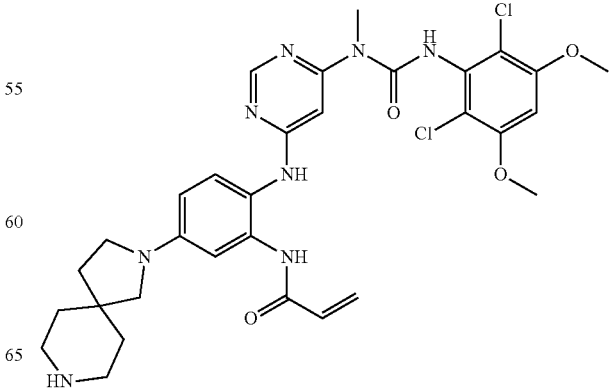

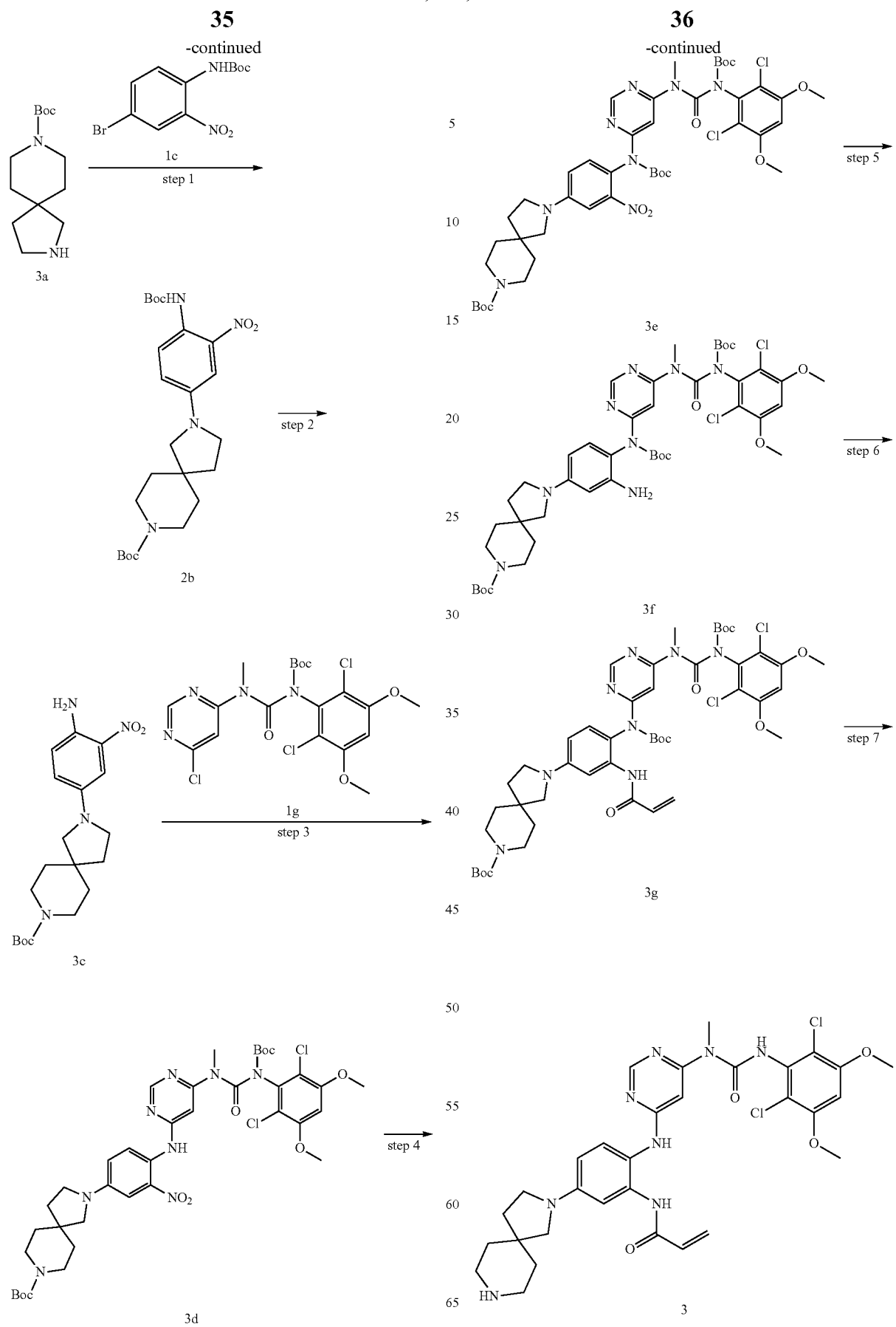

Step 1

Tert-butyl 2-(4-((tert-butoxycarbonyl)amino)-3-nitrophenyl)-2,8-diazaspiro[2.5]decane-8-carboxylate Tert-butyl 2,8-diazaspiro[4.5]decane-8-carboxylate 3a (500 mg, 2.08 mmol), tert-butyl (4-bromo-2-nitrophenyl)carbamate 1c (660 mg, 2.08 mmol), 4,5-bis(diphenylphosphino)-9,9-dimethylxanthene (230 mg, 0.42 mmol), tris(dibenzylideneacetone)dipalladium (380 mg, 0.42 mmol) and cesium carbonate (2.03 g, 6.24 mmol) were dissolved in 20 mL of toluene and reacted at 120° C. for 4 hours. The reaction solution was cooled to room temperature, filtered, and concentrated under reduced pressure, the resulting residue was purified by silica gel column chromatography (eluent: A system) to obtain tert-butyl 2-(4-((tert-butoxycarbonyl)amino)-3-nitrophenyl)-2,8-diazaspiro[2.5]decane-8-carboxylate 3b (260 mg, red solid), yield: 26.2%. MS m/z (ESI): 477.0 [M+1]

Step 2

Tert-butyl 2-(4-amino-3-nitrophenyl)-2,8-diazaspiro[4.5]decane-8-carboxylate

Tert-butyl 2-(4-((tert-butoxycarbonyl)amino)-3-nitrophenyl)-2,8-diazaspiro[2.5]decane-8-carboxylate 3b (260 mg, 0.54 mmol) and potassium hydroxide (91.83 mg, 1.64 mmol) were dissolved in 8 mL of a mixed solution of water and ethanol (V/V=1/3), heated to 90° C. and reacted for 6 hours. The reaction solution was concentrated under reduced pressure, 10 mL of ethyl acetate was added, layered, the aqueous phase was extracted with ethyl acetate (10 mL×2), the organic phases were combined and dried over anhydrous sodium sulfate, filtered, and concentrated under reduced pressure to obtain crude product of tert-butyl 2-(4-amino-3-nitrophenyl)-2,8-diazaspiro[4.5]decane-8-carboxylate 3c (160 mg, black red solid), yield: 75.5%.

MS m/z (ESI): 377.0 [M+1]

Step 3

Tert-butyl 2-(4-((6-(3-(tert-butoxycarbonyl)-3-(2,6-dichloro-3,5-dimethoxyphenyl)-1-methylureido)pyrimidin-4-yl)amino)-3-nitrophenyl)-2,8-diazaspiro[4.5]decane-8-carboxylate Tert-butyl (6-chloropyrimidin-4-yl)(methyl)carbamoyl-(2,6-dichloro-3,5-dimethoxyphenyl)carbamate 1g (216 mg, 0.44 mmol), tert-butyl 2-(4-amino-3-nitrophenyl)-2,8-diazaspiro[4.5]decane-8-carboxylate 3c (150 mg, 0.40 mmol), 4,5-bis(diphenylphosphino)-9,9-dimethylxanthene (46 mg, 0.08 mmol), tris(dibenzylideneacetone)dipalladium (146 mg, 0.04 mmol) and cesium carbonate (390 mg, 1.20 mmol) were dissolved in 10 mL of toluene and reacted at 110° C. for 4 hours. The reaction solution was cooled to room temperature, filtered, and concentrated under reduced pressure, the resulting residue was purified by silica gel column chromatography (eluent: A system) to obtain tert-butyl 2-(4-((6-(3-(tert-butoxycarbonyl)-3-(2,6-dichloro-3,5-dimethoxyphenyl)-1-methylureido)pyrimidin-4-yl)amino)-3-nitrophenyl)-2,8-diazaspiro[4.5]decane-8-carboxylate 3d (80 mg, red solid), yield: 27.1%.

Step 4

Tert-butyl 2-(4-((tert-butoxycarbonyl)(6-(3-(tert-butoxycarbonyl)-3-(2,6-dichloro-3,5-dimethoxyphenyl)-1-methylureido)pyrimidin-4-yl)amino)-3-nitrophenyl)-2,8-diazaspiro[4.5]decane-8-carboxylate Tert-butyl 2-(4-((6-(3-(tert-butoxycarbonyl)-3-(2,6-dichloro-3,5-dimethoxyphenyl)-1-methylureido)pyrimidin-4-yl)amino)-3-nitrophenyl)-2,8-diazaspiro[4.5]decane-8-carboxylate 3d (80 mg, 0.096 mmol) was dissolved in 10 mL of tetrahydrofuran, di-tert-butyl dicarbonate (32 mg, 0.144 mmol) and 4-dimethylaminopyridine (6 mg, 0.046 mmol) were added, heated to 78° C. and reacted for 1 hour. The reaction solution was concentrated under reduced pressure to obtain crude product of tert-butyl 2-(4-((tert-butoxycarbonyl)(6-(3-(tert-butoxycarbonyl)-3-(2,6-dichloro-3,5-dimethoxyphenyl)-1-methylureido)pyrimidin-4-yl)amino)-3-nitrophenyl)-2,8-diazaspiro[4.5]decane-8-carboxylate 3e (89 mg, yellow solid), yield: 100%.

Step 5

Tert-butyl 2-(3-amino-4-((tert-butoxycarbonyl)(6-(3-(tert-butoxycarbonyl)-3-(2,6-dichloro-3,5-dimethoxyphenyl)-1-methylureido)pyrimidin-4-yl)amino)phenyl)-2,8-diazaspiro[4.5]decane-8-carboxylate Tert-butyl 2-(4-((tert-butoxycarbonyl)(6-(3-(tert-butoxycarbonyl)-3-(2,6-dichloro-3,5-dimethoxyphenyl)-1-methylureido)pyrimidin-4-yl)amino)-3-nitrophenyl)-2,8-diazaspiro[4.5]decane-8-carboxylate 3e (89 mg, 0.0955 mmol) was dissolved in 6 mL of a mixed solution of tetrahydrofuran and methanol (V/V=1/2), Raney nickel (50 mg) was added and reacted for 12 hours at room temperature under the protection of hydrogen. The reaction solution was filtered, and concentrated under reduced pressure, the resulting residue was purified by silica gel column chromatography (eluent: A system) to obtain tert-butyl 2-(3-amino-4-((tert-butoxycarbonyl)(6-(3-(tert-butoxycarbonyl)-3-(2,6-dichloro-3,5-dimethoxyphenyl)-1-methylureido)pyrimidin-4-yl)amino)phenyl)-2,8-diazaspiro[4.5]decane-8-carboxylate 3f (85 mg, yellow solid), yield: 98.7%.

Step 6

Tert-butyl 2-(3-acrylamido-4-((tert-butoxycarbonyl)(6-(3-(tert-butoxycarbonyl)-3-(2,6-dichloro-3,5-dimethoxyphenyl)-1-methylureido)pyrimidin-4-yl)amino)phenyl)-2,8-diazaspiro[4.5]decane-8-carboxylate Tert-butyl 2-(3-amino-4-((tert-butoxycarbonyl)(6-(3-(tert-butoxycarbonyl)-3-(2,6-dichloro-3,5-dimethoxyphenyl)-1-methylureido)pyrimidin-4-yl)amino)phenyl)-2,8-diazaspiro[4.5]decane-8-carboxylate 3f (85 mg, 0.094 mmol) was dissolved in 10 mL of dichloromethane, the solution was added with N,N-diisopropylethylamine (36.5 mg, 0.283 mmol) and acryloyl chloride (10 mg, 0.104 mmol) and reacted at room temperature for 1 hour. The reaction solution was concentrated under reduced pressure, the resulting residue was purified by silica gel column chromatography (eluent: A system) to obtain tert-butyl 2-(3-acrylamido-4-((tert-butoxycarbonyl)(6-(3-(tert-butoxycarbonyl)-3-(2,6-dichloro-3,5-dimethoxyphenyl)-1-methylureido)pyrimidin- 4-yl)amino)phenyl)-2,8-diazaspiro[4.5]decane-8-carboxylate 3g (80 mg, yellow solid), yield: 88.8%.

Step 7

N-(2-((6-(3-(2,6-dichloro-3,5-dimethoxyphenyl)-1-methylureido)pyrimidin-4-yl)amino)-5-(2,8-diazaspiro[4.5]decan-2-yl)phenyl)acrylamide Tert-butyl 2-(3-acrylamido-4-((tert-butoxycarbonyl)(6-(3-(tert-butoxycarbonyl)-3-(2,6-dichloro-3,5-dimethoxyphenyl)-1-methylureido)pyrimidin-4-yl)amino)phenyl)-2,8-diazaspiro[4.5]decane-8-carboxylate 3g (80 mg, 0.084 mmol) was dissolved in 6 mL of dichloromethane, the solution was added with and 3 mL of trifluoroacetic acid under an ice bath, and reacted at room temperature for 12 hours under the protection of nitrogen. The reaction solution was concentrated under reduced pressure. 20 mL of mixed solution of dichloromethane and methanol (V/V=10/1) was added, washed with saturated sodium bicarbonate solution (10 mL), and the organic phase was concentrated under reduced pressure, and the resulting residue was purified by silica gel thin layer chromatography (eluent: B system) to obtain N-(2-((6-(3-(2,6-dichloro-3,5-dimethoxyphenyl)-1-methylureido)pyrimidin-4-yl)amino)-5-(2,8-diazaspiro[4.5]decan-2-yl)phenyl)acrylamide 3 (17 mg, yellow solid), yield: 31.0%. MS m/z (ESI): 656.8 [M+1]

$^1$H NMR (400 MHz, DMSO-d$_6$) δ 12.11 (s, 1H), 9.60 (s, 1H), 8.71-8.63 (m, 2H), 8.29 (s, 1H), 7.21 (d, J=8.8 Hz, 1H), 6.96 (s, 1H), 6.89 (s, 1H), 6.56-6.46 (m, 1H), 6.42 (d, J=8.0 Hz, 1H), 6.2 (d, J=15.6 Hz, 1H), 5.69 (d, J=10.0 Hz, 1H), 3.93 (s, 6H), 3.32 (t, J=6.4 Hz, 2H), 3.25-3.16 (m, 5H), 3.15-3.05 (m, 4H), 1.93 (t, J=7.2 Hz, 2H), 1.81-1.68 (m, 4H).

Example 4

N-(2-((6-(3-(2,6-Dichloro-3,5-dimethoxyphenyl)-1-methylureido)pyrimidin-4-yl)amino)-5-(7-ethyl-2,7-diazaspiro[3.5]nonan-2-yl)phenyl)acrylamide

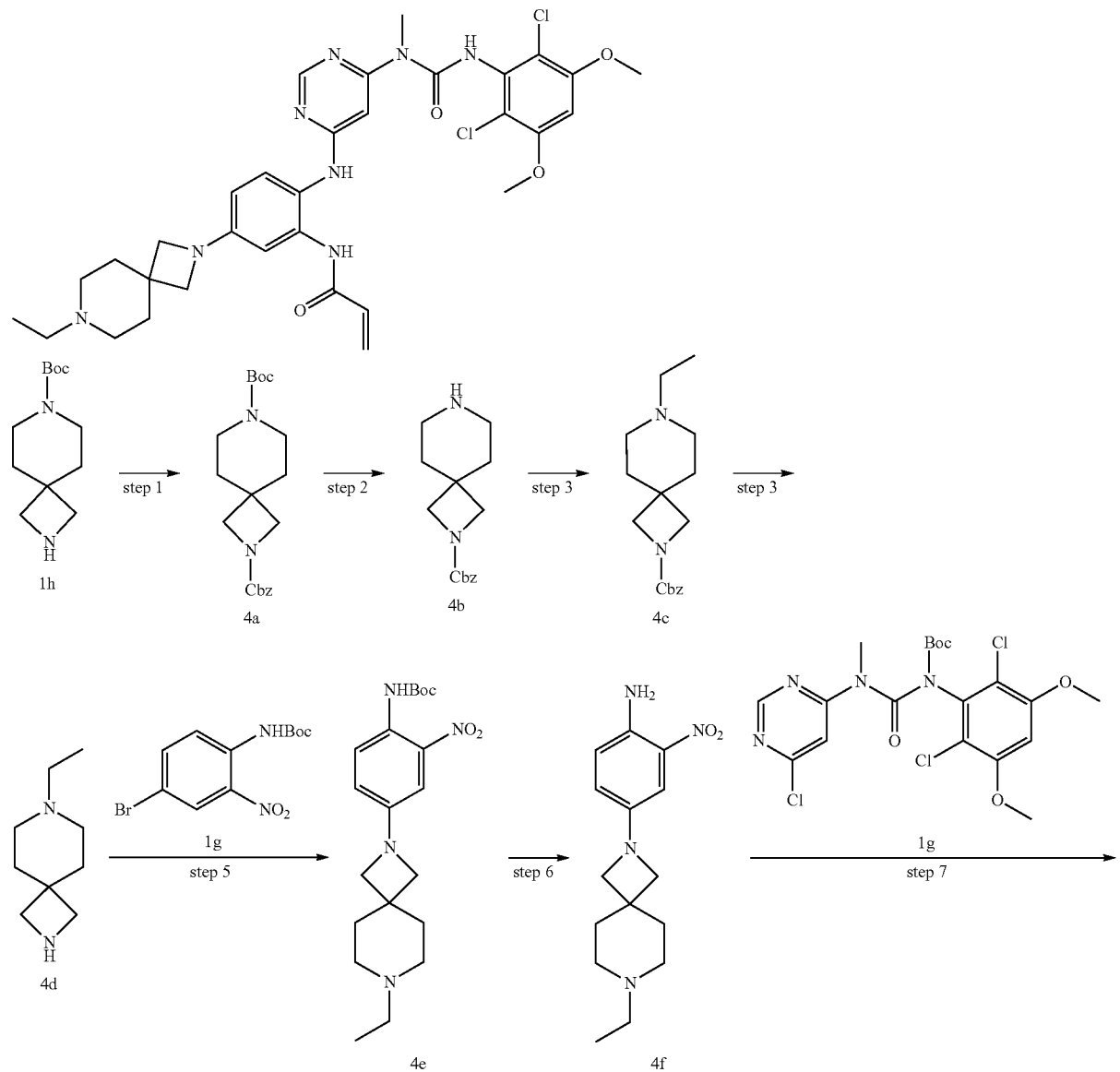

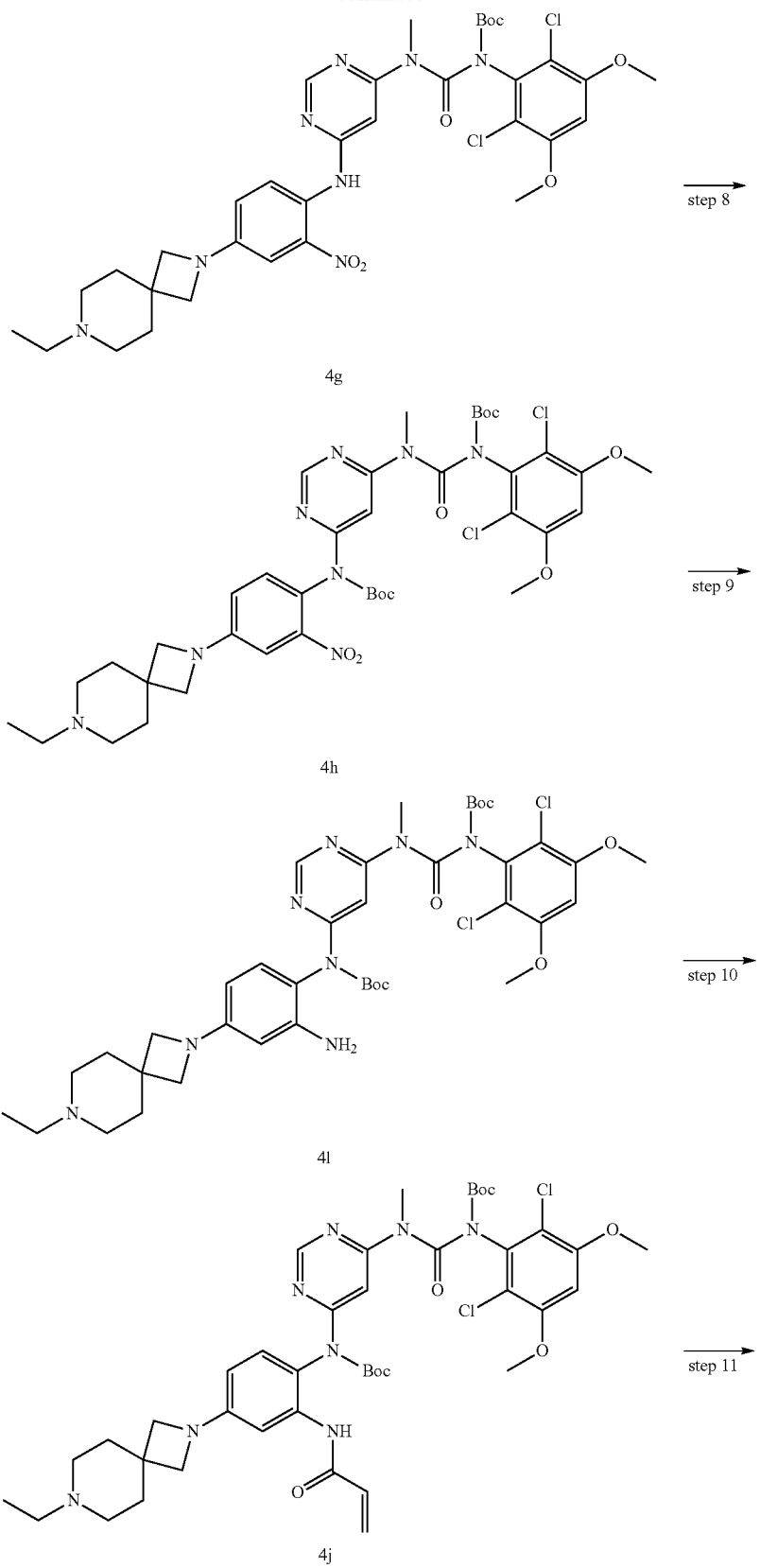

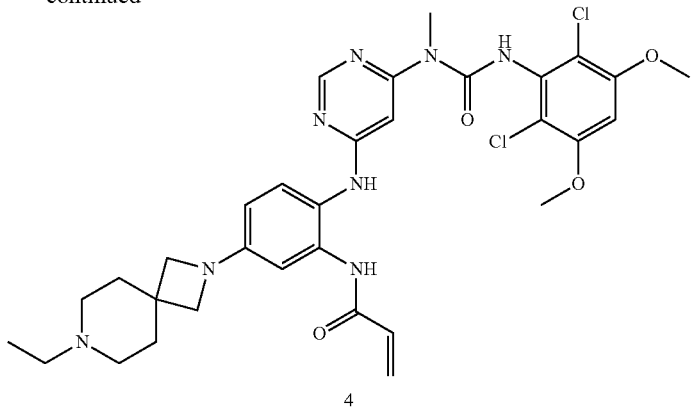

Step 1

2-Benzyl 7-(tert-butyl)-2,7-diazaspiro[3.5]nonane-2,7-dicarboxylate

Tert-butyl 2,7-diazaspiro[3.5]nonane-7-carboxylate 1l1 (2.0 g, 8.84 mmol) was dissolved in 20 mL of dichloromethane, the solution was added with benzyl chloroformate (3.06 g, 17.67 mmol) and N,N-diisopropylethylamine (4.57 g, 35.35 mmol), and reacted at room temperature for 12 hours. The reaction solution was concentrated under reduced pressure, 20 mL of ethyl acetate was added for dissolution, washed with 1M hydrochloric acid solution (10 mL) and saturated sodium chloride solution (10 mL) successively. The organic phase was concentrated under reduced pressure to obtain 2-Benzyl 7-(tert-butyl)-2,7-diazaspiro[3.5]nonane-2,7-dicarboxylate 4a (3.18 g, yellow oil), yield: 100%.

Step 2

Benzyl 2,7-diazaspiro[3.5]nonane-2-carboxylate

2-Benzyl 7-(tert-butyl)-2,7-diazaspiro[3.5]nonane-2,7-dicarboxylate 4a (3.20 g, 8.88 mmol) was dissolved in 20 mL of dichloromethane. The solution was added with 10 mL of trifluoroacetic acid and reacted at room temperature for 4 hours. The reaction solution was concentrated under reduced pressure, 30 mL of ethyl acetate was added to dissolve the same, washed with sodium bicarbonate solution (10 mL×2) and saturated sodium chloride solution (10 mL) successively, the organic phase was concentrated under reduced pressure, and the resulting residue was purified by silica gel column chromatography (eluent: A system) to obtain benzyl 2,7-diazaspiro[3.5]nonane-2-carboxylate 4b (2.30 g, colorless viscous material), yield: 99.6%.

$^{1}$H NMR (400 MHz, CDCl$_3$) δ 9.41 (s, 1H), 7.43-7.29 (m, 5H), 5.09 (s, 2H), 3.77 (s, 4H), 3.16-2.96 (m, 4H), 2.09-1.96 (m, 4H).

Step 3

Benzyl 7-ethyl-2,7-diazaspiro[3.5]nonane-2-carboxylate

Benzyl 2,7-diazaspiro[3.5]nonane-2-carboxylate 4b (2.3 g, 8.83 mmol) was dissolved in 20 mL of methanol, the solution was added with 10 mL of acetaldehyde, acetic acid (1.50 g, 26.5 mmol) and sodium cyanoborohydride (2.22 g, 35.34 mmol), reacted at room temperature for 12 hours. The reaction solution was concentrated under reduced pressure, 20 mL of ethyl acetate and 10 mL of water were added, layered, the aqueous phase was washed with saturated sodium bicarbonate solution (10 mL) and saturated sodium chloride solution (10 mL) successively, dried over anhydrous sodium sulfate, filtered, and concentrated under reduced pressure, the resulting residue was purified by silica gel column chromatography (eluent: B system) to obtain benzyl 7-ethyl-2,7-diazaspiro[3.5]nonane-2-carboxylate 4c (2.0 g, colorless viscous material), yield: 78.4%. $^{1}$H NMR (400 MHz, CDCl$_3$) δ 7.42-7.31 (m, 5H), 5.1 (s, 2H), 3.9-3.7 (m, 4H), 3.58-3.38 (m, 2H), 3.15-3.02 (m, 2H), 2.85-2.55 (m, 2H), 2.3-2.06 (m, 4H), 1.39 (t, J=12 Hz, 3H).

Step 4

7-Ethyl-2,7-diazaspiro[3.5]nonane

Benzyl 7-ethyl-2,7-diazaspiro[3.5]nonane-2-carboxylate 4c (2.00 g, 6.94 mmol) was dissolved in 20 mL of methanol, palladium on carbon (70 mg), reacted at room temperature for 12 hours under the protection of hydrogen. The reaction solution was filtered, and the filtrate was concentrated under reduced pressure to obtain 7-ethyl-2,7-diazaspiro[3.5]nonane 4d (1.0 g, oily material), yield: 93.4%.

Step 5

Tert-butyl (4-(7-ethyl-2,7-diazaspiro[3.5]nonan-2-yl)-2-nitrophenyl)carbamate 7-Ethyl-2,7-diazaspiro[3.5]nonane 4d (1.50 g, 4.73 mmol), tert-butyl (4-bromo-2-nitrophenyl)carbamate 1c (1.09 g, 7.09 mmol), 4,5-bis(diphenylphosphino)-9,9-dimethylxanthene (821 mg, 1.42 mmol), tris(dibenzylideneacetone)dipalladium (649 mg, 0.71 mmol) and cesium carbonate (4.62 g, 14.19 mmol) were dissolved in 50 mL of toluene and reacted at 110° C. for 4 hours. The reaction solution was cooled to room temperature, filtered, and concentrated under reduced pressure, and the resulting residue was purified by silica gel column chromatography (eluent: B system) to obtain tert-butyl (4-(7-ethyl-2,7-diazaspiro[3.5]nonan-2-yl)-2-nitrophenyl)carbamate 4e (1.00 g, red solid), yield: 54.1%.

MS m/z (ESI): 391.0 [M+1]

Step 6

4-(7-Ethyl-2,7-diazaspiro[3.5]nonan-2-yl)-2-nitroaniline

Tert-butyl (4-(7-ethyl-2,7-diazaspiro[3.5]nonan-2-yl)-2-nitrophenyl)carbamate 4e (1.00 g, 2.56 mmol) was dissolved in 10 mL of dichloromethane, 5 mL of trifluoroacetic acid was added and reacted at room temperature for 4 hours. The reaction solution was concentrated under reduced pressure and the resulting residue was purified by silica gel column chromatography (eluent: B system) to obtain 4-(7-ethyl-2,7-diazaspiro[3.5]nonan-2-yl)-2-nitroaniline 4f (680 mg, red solid), yield: 91.5%.

$^1$H NMR (400 MHz, CDCl$_3$) δ 7.11 (s, 1H), 6.76 (d, J=8.8 Hz, 1H), 6.73-6.67 (m, 1H), 3.65-3.58 (m, 4H), 3.19-3.03 (m, 4H), 2.72-2.56 (m, 2H), 2.45-2.35 (m, 2H), 2.17-2.08 (m, 2H), 1.41 (t, J=5.6 Hz, 3H).

Step 7

Tert-butyl N-(2,6-dichloro-3,5-dimethoxy-phenyl)-N-[[6-[4-(7-ethyl-2,7-diazaspiro)[3.5]nonan-2-yl)-2-nitroaniline]pyrimidin-4-yl]-methyl-carbamoyl]carbamate Tert-butyl (6-chloropyrimidin-4-yl)(methyl)carbamoyl-(2,6-dichloro-3,5-dimethoxyphenyl)carbamate 1g (1.00 g, 2.03 mmol), 4-(7-ethyl-2,7-diazaspiro[3.5]nonan-2-yl)-2-nitroaniline 4f (650 mg, 2.24 mmol), 4,5-bis(diphenylphosphino)-9,9-dimethylxanthene (259 mg, 0.447 mmol), tris(dibenzylideneacetone)dipalladium (205 mg, 0.224 mmol) and cesium carbonate (2.65 g, 6.13 mmol) was dissolved in 20 mL of toluene and reacted at 115° C. for 6 hours. The reaction solution was cooled to room temperature, filtered, and concentrated under reduced pressure, the resulting residue was purified by silica gel column chromatography (eluent: A system) to obtain tert-butyl N-(2,6-dichloro-3,5-dimethoxy-phenyl)-N-[[6-[4-(7-ethyl-2,7-diazaspiro)[3.5]nonan-2-yl)-2-nitroaniline]pyrimidin-4-yl]-methyl-carbamoyl]carbamate 4g (800 mg, red solid), yield: 52.9%.

$^1$H NMR (400 MHz, CDCl$_3$) δ 9.17 (s, 1H), 8.58 (s, 1H), 8.21 (d, J=9.2 Hz, 1H), 7.44 (s, 1H), 7.11 (d, J=2.4 Hz, 1H), 6.77-6.71 (m, 1H), 6.61 (s, 1H), 3.95 (s, 6H), 3.71 (s, 4H), 364 (s, 3H), 3.52-2.25 (m, 6H), 2.08-1.96 (m, 4H), 1.29-1.25 (m, 3H).

Step 8

Tert-butyl N-[6-[[tert-butoxycarbonyl (2,6-dichloro-3,5-dimethoxy-phenyl)carbamoyl]-methyl-amino]pyrimidin-4-yl-N-[4-(7-ethyl-2,7-diazaspiro[3.5]nonan-2-yl)-2-nitro-phenyl]carbamate Tert-butyl N-(2,6-dichloro-3,5-dimethoxy-phenyl)-N-[[6-[4-(7-ethyl-2,7-diazaspiro)[3.5]nonan-2-yl)-2-nitroaniline]pyrimidin-4-yl]-methyl-carbamoyl]carbamate 4g (800 mg, 1.07 mmol) was dissolved in 20 mL of tetrahydrofuran, di-tert-butyl dicarbonate (351 mg, 1.61 mmol), the solution was added with 4-dimethylaminopyridine (131 mg, 1.07 mmol), heated to 80° C. and reacted for 1 hour. The reaction solution was concentrated under reduced pressure, the resulting residue was purified by silica gel column chromatography (eluent: B system) to obtain tert-butyl N-[6-[[tert-butoxycarbonyl (2,6-dichloro-3,5-dimethoxy-phenyl)carbamoyl]-methyl-amino]pyrimidin-4-yl-N-[4-(7-ethyl-2,7-diazaspiro[3.5]nonan-2-yl)-2-nitro-phenyl]carbamate 4h (850 mg, yellow solid), yield: 93.7%.

MS m/z (ESI): 423.0 [M/2+1]

Step 9

Tert-butyl N-[6-[[tert-butoxycarbonyl (2,6-dichloro-3,5-dimethoxy-phenyl)carbamoyl]-methyl-amino]pyrimidin-4-yl-N-[4-(7-ethyl-2,7-diazaspiro[3.5]nonan-2-yl)-2-amino-phenyl]carbamate Tert-butyl N-[6-[[tert-butoxycarbonyl (2,6-dichloro-3,5-dimethoxy-phenyl)carbamoyl]-methyl-amino]pyrimidin-4-yl-N-[4-(7-ethyl-2,7-diazaspiro[3.5]nonan-2-yl)-2-nitro-phenyl]carbamate 4h (850 mg, 1.01 mmol) was dissolved in 20 mL of methanol, the solution was added with Raney nickel (500 mg), and reacted for 20 hours at room temperature under the protection of hydrogen. The reaction solution was filtered, and concentrated under reduced pressure, the resulting residue was purified by silica gel column chromatography (eluent: A system) to obtain tert-butyl N-[6-[[tert-butoxycarbonyl (2,6-dichloro-3,5-dimethoxy-phenyl)carbamoyl]-methyl-amino]pyrimidin-4-yl-N-[4-(7-ethyl-2,7-diazaspiro[3.5]nonan-2-yl)-2-amino-phenyl]carbamate 4i (210 mg, pale yellow solid), yield: 25.6%.

MS m/z (ESI): 408.0 [M/2+1]

Step 10

Tert-butyl N-[6-[[tert-butoxycarbonyl (2,6-dichloro-3,5-dimethoxy-phenyl)carbamoyl]-methyl-amino]pyrimidin-4-yl-N-[4-(7-ethyl-2,7-diazaspiro[3.5]nonan-2-yl)-2-(prop-2-enoylamino)phenyl]carbamate Tert-butyl N-[6-[[tert-butoxycarbonyl (2,6-dichloro-3,5-dimethoxy-phenyl)carbamoyl]-methyl-amino]pyrimidin-4-yl-N-[4-(7-ethyl-2,7-diazaspiro[3.5]nonan-2-yl)-2-amino-phenyl]carbamate 4i (210 mg, 0.257 mmol) was dissolved in 10 mL of dichloromethane, and N,N-diisopropylethylamine (133 mg, 1.03 mmol), the solution was added with acryloyl chloride (46.6 mg, 0.815 mmol) and reacted at room temperature for 48 hours. The reaction solution was concentrated under reduced pressure, the resulting residue was purified by silica gel column chromatography (eluent: A system) to obtain tert-butyl N-[6-[[tert-butoxycarbonyl(2,6-dichloro-3,5-dimethoxy-phenyl)carbamoyl]-methyl-amino]pyrimidin-4-yl-N-[4-(7-ethyl-2,7-diazaspiro[3.5]nonan-2-yl)-2-(prop-2-enoylamino)phenyl]carbamate 4j (120 mg, yellow solid), yield: 53.6%.

MS m/z (ESI): 435.0 [M/2+1]

Step 11

N-(2-((6-(3-(2,6-Dichloro-3,5-dimethoxyphenyl)-1-methylureido)pyrimidin-4-yl)amino)-5-(7-ethyl-2,7-diazaspiro[3.5]nonan-2-yl)phenyl)acrylamide Tert-butyl N-[6-[[tert-butoxycarbonyl (2,6-dichloro-3,5-dimethoxy-phenyl)carbamoyl]-methyl-amino]pyrimidin-4-yl-N-[4-(7-ethyl-2,7-diazaspiro[3.5]nonan-2-yl)-2-(prop-2-enoylamino)phenyl]carbamate 4j (120 mg, 0.138 mmol) was dissolved in 10 mL of dichloromethane, the solution was added with 5 mL of trifluoroacetic acid and reacted at room temperature for 14 hours. The reaction solution was concentrated under reduced pressure, 20 mL of a mixed solution of dichloromethane and methanol (V/V=10/1) was added and washed with a saturated sodium carbonate solution (10 mL) and a saturated sodium chloride solution (10 mL), the organic phase was concentrated under reduced pressure, the resulting residue was purified by silica gel column chromatography (eluent: B system) to obtain N-(2-((6-(3-(2,6-dichloro-3,5-dimethoxyphenyl)-1-methylureido)pyrimidin-4-yl)amino)-5-(7-ethyl-2,7-diazaspiro[3.5]nonan-2-yl)phenyl)acrylamide 4 (25 mg, yellow solid), yield: 27.1%.

MS m/z (ESI): 668.8 [M+1]

$^1$H NMR (400 MHz, DMSO-$d_6$) δ 12.09 (s, 1H), 10.48 (s, 1H), 9.69 (s, 1H), 8.87 (s, 1H), 8.30 (s, 1H), 7.23 (d, J=8.8 Hz, 1H), 6.94 (s, 1H), 6.89 (s, 1H), 6.63-6.45 (m, 1H), 6.32-6.15 (m, 2H), 5.71 (d, J=10.0 Hz, 1H), 3.93 (s, 6H), 3.75-3.55 (m, 4H), 3.48-3.38 (m, 2H), 3.22 (s, 3H), 3.25-2.81 (m, 4H), 2.19-1.92 (m, 4H), 1.28-1.19 (m, 3H).

Example 5

N-(2-((6-(3-(2,6-Dichloro-3,5-dimethoxyphenyl)-1-methylureido)pyrimidin-4-yl)amino)-5-(4-ethyl-4,7-diazaspiro[2.5]octan-7-yl)phenyl)acrylamide

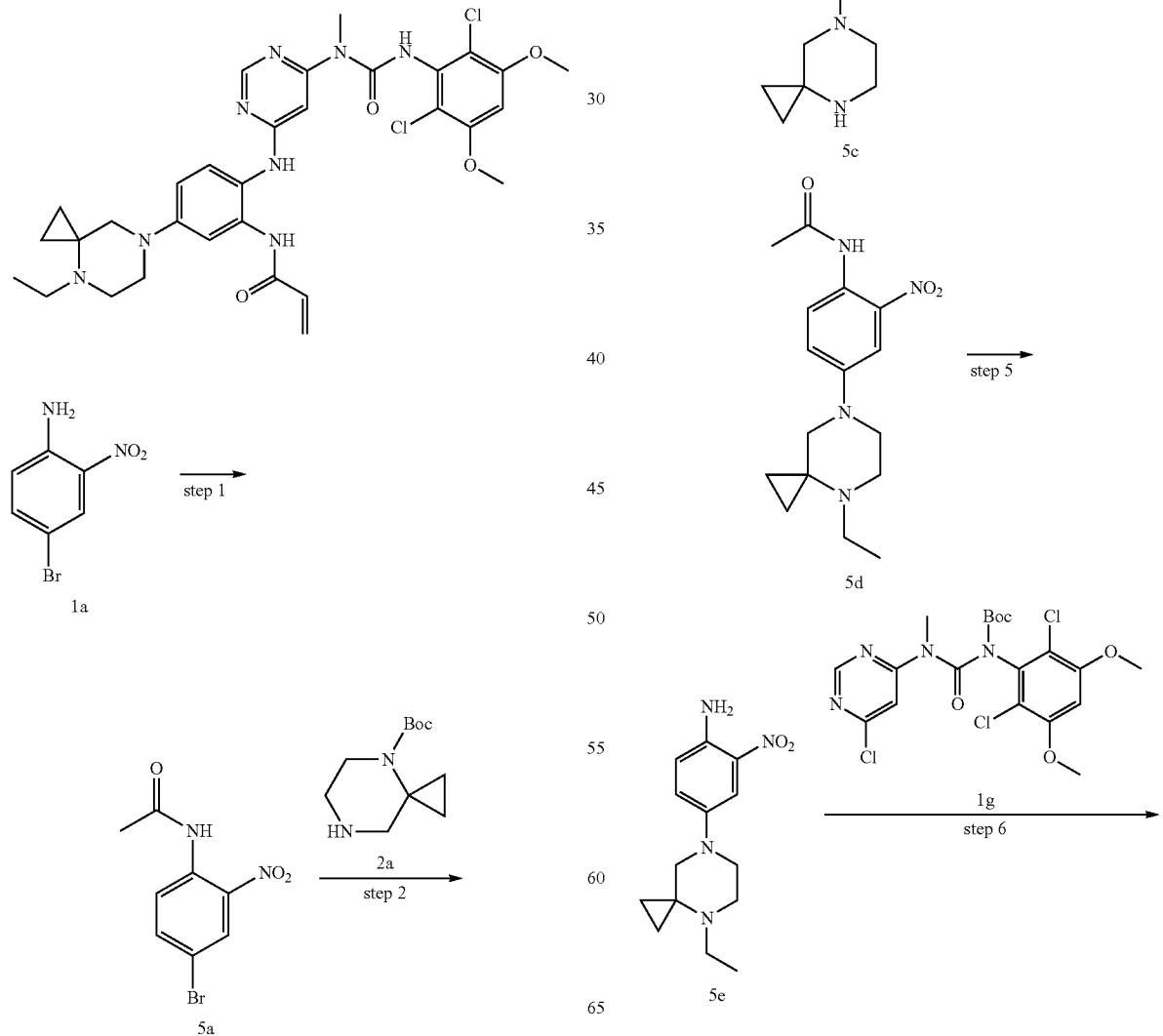

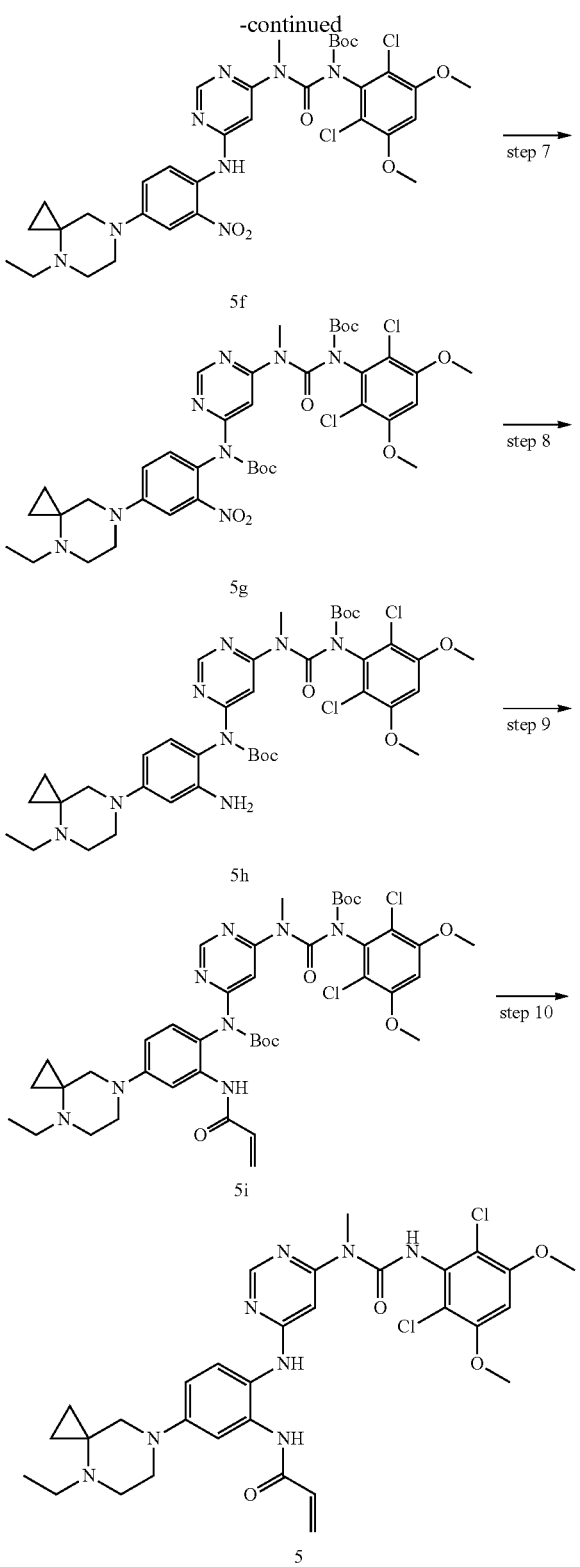

with acetic anhydride (2.85 mL, 30.41 mmol), heated to 100° C. and reacted for 5 hours. The reaction solution was added with 100 mL of water, and a solid was precipitated, filtered, and the filter cake was dissolved in 50 mL of dichloromethane, the organic phase was washed with water (20 mL×2), dried over anhydrous sodium sulfate, filtered and concentrated under reduced pressure to obtain N-(4-bromo-2-nitrophenyl)acetamide 5a (6.60 g, yellow solid), yield: 92.1%.

MS m/z (ESI): 258.8 [M+1]

Step 2

Tert-butyl 7-(4-acetamido-3-nitrophenyl)-4,7-diazaspiro[2.5]octane-4-carboxylate N-(4-Bromo-2-nitrophenyl)acetamide 5a (1.00 g, 3.86 mmol), tert-butyl 4,7-diazaspiro[2.5]octane-4-carboxylate 2a (820 mg, 3.86 mmol), 4,5-bis(diphenylphosphino)-9,9-dimethylxanthene (450 mg, 0.772 mmol), tris(dibenzylideneacetone)dipalladium (350 mg, 0.386 mmol) and cesium carbonate (3.77 g, 11.6 mmol) were dissolved in 50 mL of toluene and reacted at 115° C. for 4 hours under the protection of argon. The reaction solution was cooled to room temperature, filtered, concentrated under reduced pressure and the resulting residue was purified by silica gel column chromatography (eluent: A system) to obtain tert-butyl 7-(4-acetamido-3-nitrophenyl)-4,7-diazaspiro[2.5]octane-4-carboxylate 5b (920 mg, red solid), yield: 61.3%.

$^1$H NMR (400 MHz, CDCl$_3$) δ 10.01 (s, 1H), 8.61 (d, J=9.6 Hz, 1H), 7.68 (s, 1H), 7.32-7.27 (m, 2H), 3.85-3.65 (m, 2H), 3.31-3.15 (m, 2H), 3.02 (s, 2H), 2.27 (s, 3H), 1.49 (s, 9H), 1.14-1.08 (m, 2H), 0.98-0.88 (m, 2H).

Step 3

(N-(2-Nitro-4-(4,7-diazaspiro[2.5]octan-7-yl)phenyl) acetamide

Tert-butyl 7-(4-acetamido-3-nitrophenyl)-4,7-diazaspiro [2.5]octane-4-carboxylate 5b (720 mg, 2.36 mmol) was dissolved in 10 mL of dichloromethane, the solution was added with 5 mL of trifluoroacetic acid and reacted at room temperature for 4 hours. The reaction solution was concentrated under reduced pressure, dissolved by adding 20 mL of ethyl acetate, layered, the organic phase was washed with saturated sodium carbonate solution (10 mL) and saturated saline solution (10 mL) successively, dried over anhydrous sodium sulfate, filtered, and concentrated under reduced pressure to obtain (N-(2-nitro-4-(4,7-diazaspiro[2.5]octan-7-yl)phenyl)acetamide 5c (650 mg, red solid), yield: 95.0%.

MS m/z (ESI): 291.0 [M+1]

Step 4

N-(4-(4-Ethyl-4,7-diazaspiro[2.5]octan-7-yl)-2-nitrophenyl)acetamide (N-(2-Nitro-4-(4,7-diazaspiro[2.5]octan-7-yl)phenyl)acetamide 5c (600 mg, 2.06 mmol) was dissolved in 20 mL methanol, 2 mL of 40% acetaldehyde, acetic acid (250 mg, 4.13 mmol) and sodium cyanoborohydride (260 mg, 4.13 mmol) were added and reacted for 12 hours at room temperature. The reaction solution was concentrated under reduced pressure, 20 mL of ethyl acetate was added, the organic phase was washed with saturated sodium carbonate solution (10 mL×2) and saturated sodium chloride solution (10 mL) successively, dried over anhydrous sodium sulfate, filtered, and concentrated under reduced pressure to obtain N-(4-(4-ethyl-4,7-diazaspiro[2.5]octan-7-yl)-2-nitrophenyl) acetamide 5d (660 mg, red solid), yield: 100%.

MS m/z (ESI): 319.0 [M+1]

Step 5

4-(4-Ethyl-4,7-diazaspiro[2.5]octan-7-yl)-2-nitroaniline

N-(4-(4-Ethyl-4,7-diazaspiro[2.5]octan-7-yl)-2-nitrophenyl)acetamide 5d (700 mg, 2.20 mmol) was dissolved in 20 mL of ethanol, the solution was added with 4 mL of potassium hydroxide (493.4 mg, 8.79 mmol), heated to 90° C. and reacted for 3 hours. The reaction solution was concentrated under reduced pressure, 20 mL of ethyl acetate and 10 mL were added, layered, the organic phase was washed with saturated sodium chloride solution (10 mL), dried over anhydrous sodium sulfate, filtered, concentrated under reduced pressure and the resulting residue was purified by silica gel column chromatography (eluent: B system) to obtain 4-(4-ethyl-4,7-diazaspiro[2.5]octan-7-yl)-2-nitroaniline 5e (6.60 g, red solid), yield: 98.8%.

MS m/z (ESI): 277.0 [M+1]

Step 6

Tert-butyl N-(2,6-dichloro-3,5-dimethoxy-phenyl)-N-[[6-[4-(8-ethyl-5,8-diazaspiro)[2.5]octan-5-yl)-2-nitroaniline]pyrimidin-4-yl]-methyl-carbamoyl]carbamate Tert-butyl (6-chloropyrimidin-4-yl)(methyl)carbamoyl-(2,6-dichloro-3,5-dimethoxyphenyl)carbamate 1g (1.00 g, 2.03 mmol), 4-(4-ethyl-4,7-diazaspiro[2.5]octan-7-yl)-2-nitroaniline 5e (618 mg, 2.24 mmol), 4,5-bis(diphenylphosphino)-9,9-dimethylxanthene (235 mg, 0.407 mmol), tris(dibenzylideneacetone)dipalladium (186 mg, 0.203 mmol) and cesium carbonate (1.99 g, 6.10 mmol) were dissolved in 30 mL toluene, the mixture was reacted at 115° C. for 4 hours under the protection of argon. The reaction solution was cooled to room temperature, filtered, and concentrated under reduced pressure, the resulting residue was purified by silica gel column chromatography (eluent: B system) to obtain tert-butyl N-(2,6-dichloro-3,5-dimethoxy-phenyl)-N-[[6-[4-(8-ethyl-5,8-diazaspiro)[2.5]octan-5-yl)-2-nitroaniline]pyrimidin-4-yl]-methyl-carbamoyl]carbamate 5f (800 mg, red solid), yield: 53.7%.

MS m/z (ESI): 366.0 [M/2+1]

Step 7

Tert-butyl N-[6-[[tert-butoxycarbonyl (2,6-dichloro-3,5-dimethoxy-phenyl)carbamoyl]methyl-amino] pyrimidin-4-yl]-N-[4-(8-ethyl-5,8-diazaspiro[2.5] octan-5-yl)-2-nitro-phenyl]carbamate Tert-butyl N-(2,6-dichloro-3,5-dimethoxy-phenyl)-N-[[6-[4-(8-ethyl-5,8-diazaspiro)[2.5]octan-5-yl)-2-nitroaniline] pyrimidin-4-yl]-methyl-carbamoyl]carbamate 5f (800 mg, 1.09 mmol) was dissolved in 20 mL of tetrahydrofuran, the solution was added with di-tert-butyl dicarbonate (358 mg, 1.64 mmol) and 4-dimethylaminopyridine (134 mg, 1.09 mmol), heated to 80° C. and reacted for 1 hour. The reaction solution was concentrated under reduced pressure and the resulting residue was purified by silica gel column chromatography (eluent: A system) to obtain tert-butyl N-[6-[[tert-butoxycarbonyl (2,6-dichloro-3,5-dimethoxy-phenyl)carbamoyl]methyl-amino]pyrimidin-4-yl]-N-[4-(8-ethyl-5,8-diazaspiro[2.5]octan-5-yl)-2-nitro-phenyl]carbamate 5g (850 mg, yellow solid), yield: 93.5%.

MS m/z (ESI): 832.8 [M+1]

Step 8

Tert-butyl N-[[6-[2-amino-N-tert-butoxycarbonyl-4-(8-ethyl-5,8-diazaspiro[2.5]octan-5-yl)aniline]pyrimidin-4-yl]methyl-carbamoyl]-N-(2,6-dichloro-3,5-dimethoxy-phenyl)carbamate Tert-butyl N-[6-[[tert-butoxycarbonyl (2,6-dichloro-3,5-dimethoxy-phenyl)carbamoyl]methyl-amino]pyrimidin-4-yl]-N-[4-(8-ethyl-5,8-diazaspiro[2.5]octan-5-yl)-2-nitro-phenyl]carbamate 5g (850 mg, 1.02 mmol) was dissolved in 20 mL of methanol, the solution was added with Raney nickel (400 mg), and reacted for 6 hours at room temperature under the protection of hydrogen. The reaction solution was filtered and concentrated under reduced pressure, and the resulting residue was purified by silica gel column chromatography (eluent: A system) to obtain tert-butyl N-[[6-[2-amino-N-tert-butoxycarbonyl-4-(8-ethyl-5,8-diazaspiro[2.5]octan-5-yl)aniline]pyrimidin-4-yl]methyl-carbamoyl]-N-(2,6-dichloro-3,5-dimethoxy-phenyl)carbamate 5h (600 mg, yellow solid), yield: 73.2%.

MS m/z (ESI): 401.9 [M/2+1]

Step 9

Tert-butyl N-[6-[[tert-butoxycarbonyl(2,6-dichloro-3,5-dimethoxy-phenyl)carbamoyl]methylamino] pyrimidin-4-yl]-N-[4-(8-ethyl-5,8-diazaspiro[2.5] octan-5-yl)-2-(prop-2-enoylamino)phenyl]carbamate Tert-butyl N-[[6-[2-amino-N-tert-butoxycarbonyl-4-(8-ethyl-5,8-diazaspiro[2.5]octane-5-yl)aniline]pyrimidin-4-yl]methyl-carbamoyl]-N-(2,6-dichloro-3,5-dimethoxy-phenyl)carbamate 5h (600 mg, 0.748 mmol) was dissolved in 15 mL of dichloromethane, the solution was added with N,N-diisopropylethylamine (463 mg, 3.73 mmol) and acryloyl chloride (135 mg, 1.50 mmol), and reacted at room temperature for 4 hours. The reaction solution was concentrated under reduced pressure and the resulting residue was purified by silica gel column chromatography (eluent: A system) to obtain tert-butyl N-[6-[[tert-butoxycarbonyl(2,6-dichloro-3,5-dimethoxy-phenyl)carbamoyl]methylamino]pyrimidin-4-yl]-N-[4-(8-ethyl-5,8-diazaspiro[2.5]octane-5-yl)-2-(prop-2-enoylamino)phenyl]carbamate 5i (440 mg, red solid), yield: 68.7%.

MS m/z (ESI): 378.6 [(M-100)/2+1]

Step 10

N-(2-((6-(3-(2,6-Dichloro-3,5-dimethoxyphenyl)-1-methylureido)pyrimidin-4-yl)amino)-5-(4-ethyl-4,7-diazaspiro[2.5]octan-7-yl)phenyl)acrylamide Tert-butyl N-[6-[[tert-butoxycarbonyl (2,6-dichloro-3,5-dimethoxy-phenyl)carbamoyl]methylamino]pyrimidin-4-yl]-N-[4-(8-ethyl-5,8-diazaspiro[2.5]octane-5-yl)-2-(prop-2-enoylamino)phenyl]carbamate 5i (440 mg, 0.514 mmol) was dissolved in 15 mL of dichloromethane, the solution was added with 5 mL of trifluoroacetic acid and reacted at room temperature for 12 hours. The reaction solution was concentrated under reduced pressure, 20 mL of ethyl acetate was added, washed with saturated sodium carbonate solution (20 mL) and saturated sodium chloride solution (20 mL) successively, dried over anhydrous sodium sulfate, filtered, and concentrated under reduced pressure, the resulting residue was purified by silica gel thin layer chromatography (eluent: B system) to obtain N-(2-((6-(3-(2,6-dichloro-3,5-dimethoxyphenyl)-1-methylureido)pyrimidin-4-yl)amino)-5-(4-ethyl-4,7-diazaspiro[2.5]octane-7-yl)phenyl)acrylamide 5 (100 mg, white solid), yield: 29.7%.

MS m/z (ESI): 678.8 [M+23]

$^1$H NMR (400 MHz, CDCL$_3$) δ 12.53 (s, 1H), 8.39 (s, 1H), 7.79 (s, 1H), 6.76-6.66 (m, 1H), 6.53 (s, 1H), 6.62 (d, J=16.0 Hz, 1H), 6.26-6.17 (m, 1H), 5.9-5.84 (m, 1H), 5.79 (d, J=10.0 Hz, 1H), 3.92 (s, 6H), 3.8-2.1 (m, 11H), 1.69-1.42 (m, 3H), 1.32-1.02 (m, 2H), 0.98-0.6 (m, 2H).

Example 6

N-(2-((6-(3-(2,6-Dichloro-3,5-dimethoxyphenyl)-1-methylureido)pyrimidin-4-yl)amino)-5-(7-ethyl-2,7-diazaspiro[4.4]nonan-2-yl)phenyl)acrylamide

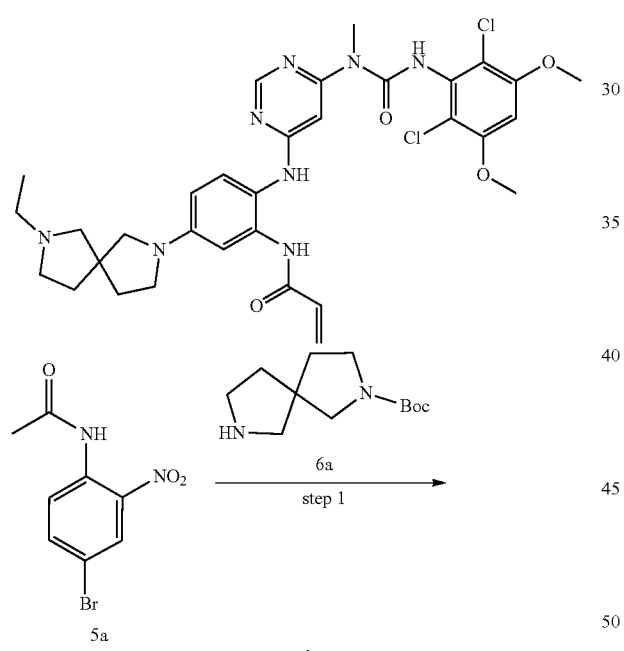

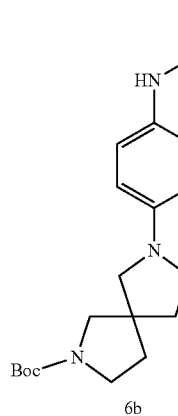

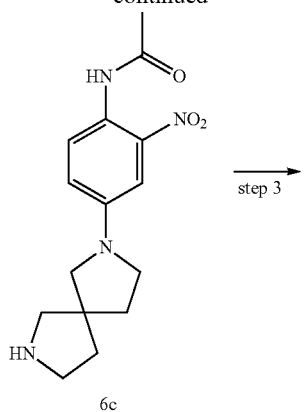

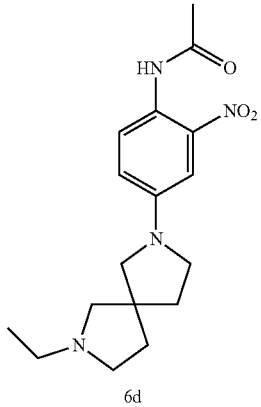

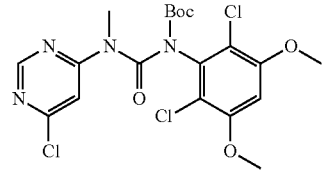

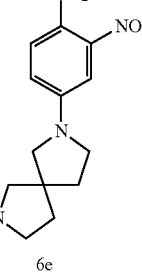

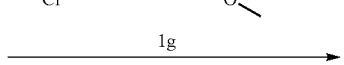

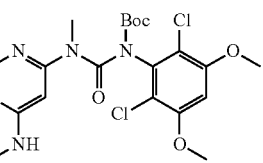

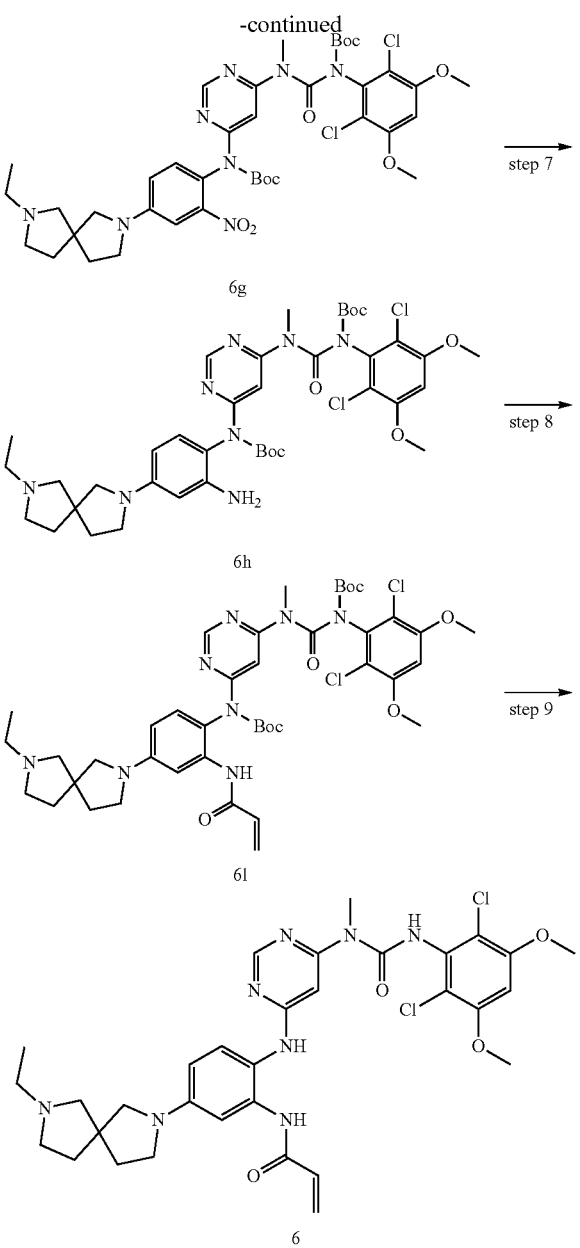

butyl 7-(4-acetylamino-3-nitrophenyl)-2,7-diazaspiro[4.4]nonane-2-carboxylate 6b (490 mg, red solid), yield: 57.1%.

MS m/z (ESI): 405.0 [M+1]

Step 2

(N-(2-Nitro-4-(2,7-diazaspiro[4.4]nonan-2-yl)phenyl)acetamide

Tert-butyl 7-(4-acetylamino-3-nitrophenyl)-2,7-diazaspiro[4.4]nonane-2-carboxylate 6b (490 mg, 1.21 mmol) was dissolved in 10 mL of dichloromethane, the solution was added with 5 mL of trifluoroacetic acid, and reacted at room temperature for 2 hours. The reaction solution was concentrated under reduced pressure, dissolved by adding 20 mL of ethyl acetate and concentrated under reduced pressure to obtain (N-(2-nitro-4-(2,7-diazaspiro[4.4]nonan-2-yl)phenyl)acetamide 6c (368 mg, red solid), yield: 100%.

MS m/z (ESI): 305.0 [M+1]

Step 3

N-(4-(7-Ethyl-2,7-diazaspiro[4.4]nonan-2-yl)-2-nitrophenyl)acetamide (N-(2-Nitro-4-(2,7-diazaspiro[4.4]nonan-2-yl)phenyl)acetamide 6c (368 mg, 1.21 mmol) was dissolved in 10 mL methanol, the solution was added with 2 mL of 40% acetaldehyde, acetic acid (145 mg, 2.42 mmol) and sodium cyanoborohydride (304 mg, 4.84 mmol), and reacted for 12 hours at room temperature. The reaction solution was concentrated under reduced pressure, 20 mL of ethyl acetate and 10 mL of water were added, layered, the organic phase was washed with saturated sodium carbonate solution (20 mL) and saturated sodium chloride solution (10 mL) successively, dried over anhydrous sodium sulfate, filtered, and concentrated under reduced pressure to obtain N-(4-(7-ethyl-2,7-diazaspiro[4.4]nonan-2-yl)-2-nitrophenyl)acetamide 6d (401 mg, red solid), yield: 100%.

MS m/z (ESI): 333.0 [M+1]

Step 4

4-(7-Ethyl-2,7-diazaspiro[4.4]nonan-2-yl)-2-nitroaniline

N-(4-(7-Ethyl-2,7-diazaspiro[4.4]nonan-2-yl)-2-nitrophenyl)acetamide 6d (401 mg, 2.20 mmol) was dissolved in 20 mL ethanol, the solution was added with 4 mL of potassium hydroxide (271 mg, 4.83 mmol), heated to 90° C. and reacted for 4 hours. The reaction solution was concentrated under reduced pressure, 20 mL of ethyl acetate and 10 mL of water were added, layered, the aqueous phase was extracted with ethyl acetate (10 mL×2), the organic phases were combined and washed with saturated sodium chloride solution (20 mL), dried over anhydrous sodium sulfate, filtered, concentrated under reduced pressure, the resulting residue was purified by silica gel column chromatography (eluent: B system) to obtain 4-(7-ethyl-2,7-diazaspiro[4.4]nonan-2-yl)-2-nitroaniline 6e (270 mg, red solid), yield: 77.1%.

MS m/z (ESI): 291.0 [M+1]

Step 5

Tert-butyl N-(2,6-dichloro-3,5-dimethoxy-phenyl)-N-[[6-[4-(3-ethyl-3,8-diazaspiro)[4.4]nonan-8-yl]-2-nitro-aniline]pyrimidin-4-yl]-methyl-carbamoyl]carbamate Tert-butyl (6-chloropyrimidin-4-yl)(methyl)carbamoyl-(2,6-dichloro-3,5-dimethoxyphenyl)carbamate 1g (400 mg, Step 1

Tert-butyl 7-(4-acetylamino-3-nitrophenyl)-2,7-diazaspiro[4.4]nonane-2-carboxylate N-(4-Bromo-2-nitrophenyl)acetamide 5a (550 mg, 2.12 mmol), tert-butyl 2,7-diazaspiro[4.4]nonane-2-carboxylate 6a (460.5 mg, 2.12 mmol), 4,5-bis(diphenylphosphino)-9,9-dimethylxanthene (246 mg, 0.425 mmol), tris(dibenzylideneacetone)dipalladium (194 mg, 0.212 mmol) and cesium carbonate (2.08 g, 6.37 mmol) were dissolved in 20 mL of toluene and reacted at 115° C. for 4 hours under the protection of hydrogen. The reaction solution was cooled to room temperature, filtered, and concentrated under reduced pressure, the resulting residue was purified by silica gel column chromatography (eluent: A system) to obtain tert- 0.813 mmol), 4-(7-ethyl-2,7-diazaspiro[4.4]nonan-2-yl)-2-nitroaniline 6e (260 mg, 0.895 mmol), 4,5-bis(diphenylphosphino)-9,9-dimethylxanthene (94 mg, 0.163 mmol), tris(dibenzylideneacetone)dipalladium (75 mg, 0.0813 mmol) and cesium carbonate (795 mg, 2.44 mmol) were dissolved in 20 mL of toluene, the mixture was reacted at 115° C. for 4 hours under the protection of argon. The reaction solution was cooled to room temperature, filtered, and concentrated under reduced pressure, the resulting residue was purified by silica gel column chromatography (eluent: B system) to obtain tert-butyl N-(2,6-dichloro-3,5-dimethoxy-phenyl)-N-[[6-[4-(3-ethyl-3,8-diazaspiro)[4.4]nonan-8-yl)-2-nitroaniline]pyrimidin-4-yl]-methyl-carbamoyl]carbamate 6f (400 mg, red solid), yield: 66.0%.

MS m/z (ESI): 323.0 [M/2+1]

Step 6

Tert-butyl N-[6-[[tert-butoxycarbonyl(2,6-dichloro-3,5-dimethoxy-phenyl)carbamoyl]methyl-amino]pyrimidin-4-yl]-N-[4-(3-ethyl-3,8-diazaspiro[4.4]nonan-8-yl)-2-nitro-phenyl]carbamate Tert-butyl N-(2,6-dichloro-3,5-dimethoxy-phenyl)-N-[[6-[4-(3-ethyl-3,8-diazaspiro)[4.4]nonan-8-yl)-2-nitroaniline]pyrimidin-4-yl]-methyl-carbamoyl]carbamate 6f (400 mg, 0.536 mmol) was dissolved in 15 mL of tetrahydrofuran, the solution was added with di-tert-butyl dicarbonate (175 mg, 0.805 mmol) and 4-dimethylaminopyridine (66 mg, 0.576 mmol), heated to 80° C. and reacted for 1 hour. The reaction solution was concentrated under reduced pressure, the resulting residue was purified by silica gel column chromatography (eluent: A system) to obtain tert-butyl N-[6-[[tert-butoxycarbonyl(2,6-dichloro-3,5-dimethoxy-phenyl)carbamoyl]methyl-amino]pyrimidin-4-yl]-N-[4-(3-ethyl-3,8-diazaspiro[4.4]nonan-8-yl)-2-nitro-phenyl]carbamate 6g (410 mg, yellow solid), yield: 90.5%.

Step 7

Tert-butyl N-[[6-[2-amino-N-tert-butoxycarbonyl-4-(3-ethyl-3,8-diazaspiro[4.4]nonan-8-yl)aniline]pyrimidin-4-yl]-methyl-carbamoyl]-N-(2,6-dichloro-3,5-dimethoxy-phenyl)carbamate Tert-butyl N-[6-[[tert-butoxycarbonyl (2,6-dichloro-3,5-dimethoxy-phenyl)carbamoyl]methyl-amino]pyrimidin-4-yl]-N-[4-(3-ethyl-3,8-diazaspiro[4.4]nonan-8-yl)-2-nitro-phenyl]carbamate 6g (450 mg, 0.532 mmol) was dissolved in 15 mL of methanol, the solution was added with Raney nickel (200 mg), and reacted for 6 hours at room temperature under the protection of hydrogen. The reaction solution was filtered, concentrated under reduced pressure, the resulting residue was purified by silica gel column chromatography (eluent: A system) to obtain tert-butyl N-[[6-[2-amino-N-tert-butoxycarbonyl-4-(3-ethyl-3,8-diazaspiro[4.4]nonan-8-yl)aniline]pyrimidin-4-yl]-methyl-carbamoyl]-N-(2,6-dichloro-3,5-dimethoxy-phenyl)carbamate 6h (310 mg, red solid), yield: 71.4%.

MS m/z (ESI): 408.7 [M/2+1]

Step 8

Tert-butyl N-[6-[[tert-butoxycarbonyl(2,6-dichloro-3,5-dimethoxy-phenyl)carbamoyl]methylamino]pyrimidin-4-yl]-N-[4-(3-ethyl-3,8-diazaspiro[4.4]nonan-8-yl)-2-(prop-2-enoylamino)phenyl]carbamate Tert-butyl N-[[6-[2-amino-N-tert-butoxycarbonyl-4-(3-ethyl-3,8-diazaspiro[4.4]nonan-8-yl)aniline]pyrimidin-4-yl]-methyl-carbamoyl]-N-(2,6-dichloro-3,5-dimethoxy-phenyl)carbamate 6h (310 mg, 0.380 mmol) was dissolved in 10 mL of dichloromethane, the solution was added with N,N-diisopropylethylamine (246 mg, 1.90 mmol) and acryloyl chloride (69 mg, 0.760 mmol) and reacted at room temperature for 4 hours. The reaction solution was concentrated under reduced pressure, the resulting residue was purified by silica gel column chromatography (eluent: A system) to obtain tert-butyl N-[6-[[tert-butoxycarbonyl(2,6-dichloro-3,5-dimethoxy phenyl)carbamoyl]methylamino]pyrimidin-4-yl]-N-[4-(3-ethyl-3,8-diazaspiro[4.4]nonan-8-yl)-2-(prop-2-enoylamino)phenyl]carbamate 6i (150 mg, red solid), yield: 45.5%.

MS m/z (ESI): 385.9 [M+1/2]

Step 9

N-(2-((6-(3-(2,6-dichloro-3,5-dimethoxyphenyl)-1-methylureido)pyrimidin-4-yl)amino)-5-(7-ethyl-2,7-diazaspiro[4.4]nonan-2-yl)phenyl)acrylamide Tert-butyl N-[6-[[tert-butoxycarbonyl (2,6-dichloro-3,5-dimethoxy-phenyl)carbamoyl]methyl amino]pyrimidin-4-yl]-N-[4-(3-ethyl-3,8-diazaspiro[4.4]nonan-8-yl)-2-(prop-2-enoylamino)phenyl]carbamate 6i (150 mg, 0.172 mmol) was dissolved in 10 mL of dichloromethane, the solution was added with 5 mL of trifluoroacetic acid and reacted at room temperature for 12 hours. The reaction solution was concentrated under reduced pressure, 20 mL of ethyl acetate was added, washed with saturated sodium carbonate solution (10 mL×2) and saturated sodium chloride solution (10 mL) successively, dried over anhydrous sodium sulfate, filtered, and concentrated under reduced pressure, the resulting residue was purified by silica gel thin layer chromatography (eluent: B system) to obtain N-(2-((6-(3-(2,6-dichloro-3,5-dimethoxyphenyl)-1-methylureido)pyrimidin-4-yl)amino)-5-(7-ethyl-2,7-diazaspiro[4.4]nonan-2-yl)phenyl)acrylamide 6 (20 mg, white solid), yield: 17.3%.

MS m/z (ESI): 335.8 [M/2+1]

$^1$H NMR (400 MHz, DMSO-$d_6$) δ 12.11 (s, 1H), 10.43-10.19 (m, 1H), 9.55 (s, 1H), 8.69 (s, 1H), 8.1 (s, 1H), 7.21 (d, J=8.8 Hz, 1H), 7.09-6.94 (m, 1H), 6.89 (s, 1H), 6.58-6.44 (m, 1H), 6.42-6.34 (m, 1H), 6.28-6.18 (m, 1H), 5.74-5.66 (m, 1H), 3.93 (s, 6H), 3.8-3.46 (m, 2H), 3.38-3.28 (m, 4H), 3.24-3.92 (m, 7H), 2.22-1.78 (m, 4H), 1.32-1.12 (m, 3H).

Example 7
N-(2-((6-(3-(2,6-Dichloro-3,5-dimethoxyphenyl)-1-methylureido)pyrimidin-4-yl)amino)-5-(4-(dimethylamino)piperidin-1-yl)phenyl)acrylamide
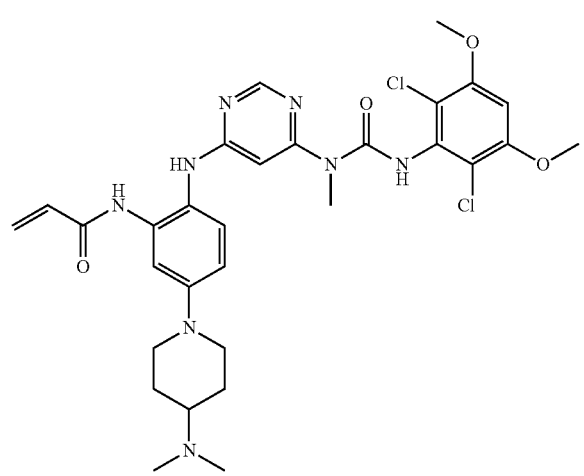
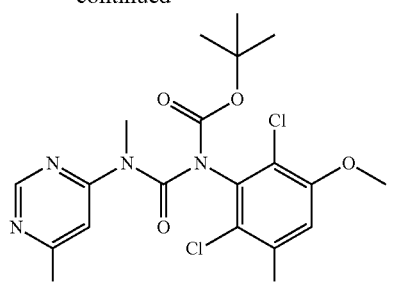
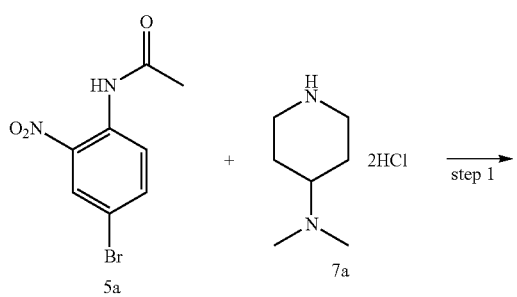
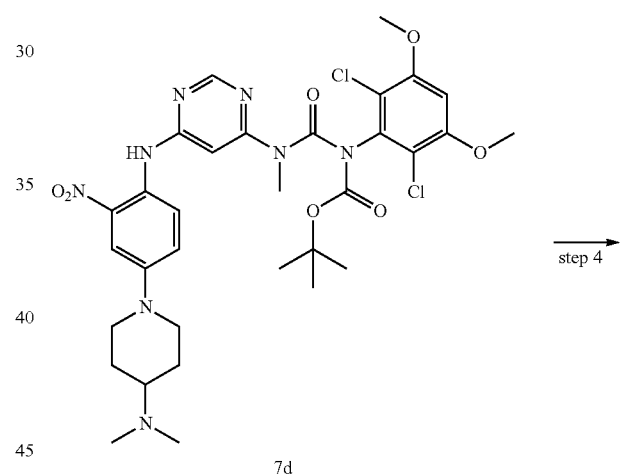
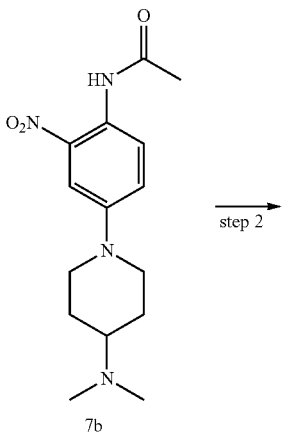
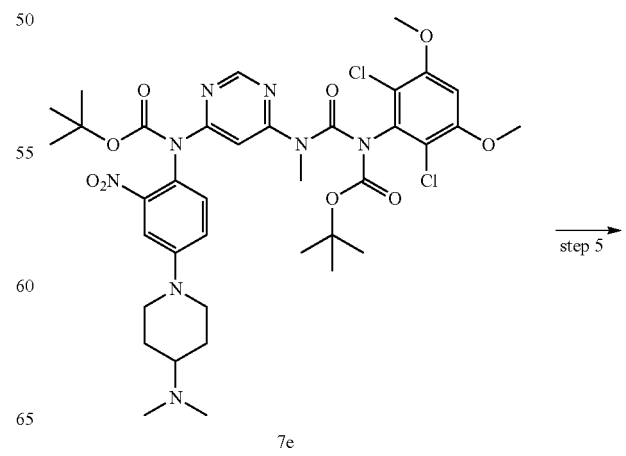

-continued

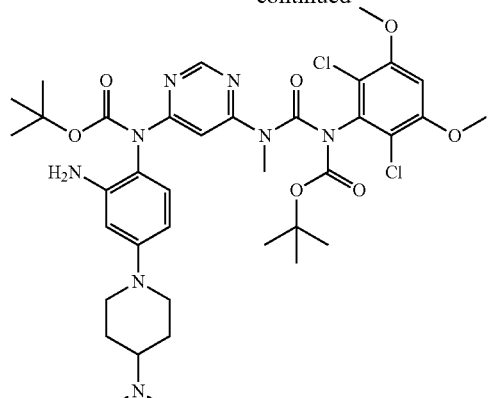

7f

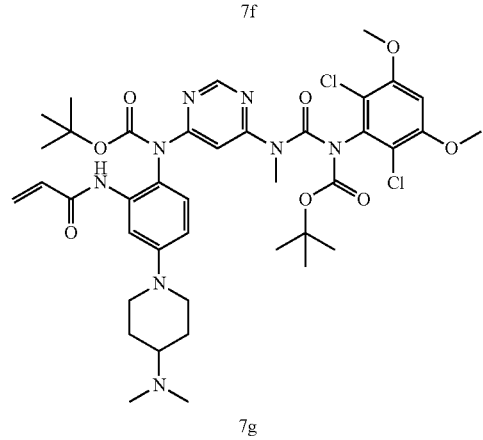

7g

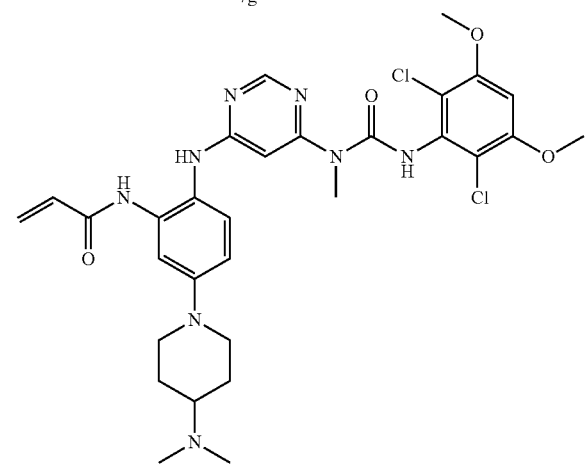

7

Step 1

N-(4-(4-(Dimethylamino)piperidin-1-yl)-2-nitrophenyl)acetamide

N-(4-Bromo-2-nitrophenyl)acetamide 5a (14.17 g, 49.72 mmol), N,N-dimethylpiperidin-4-amine dihydrochloride 7a (10.00) g, 54.69 mmol), 4,5-bis(diphenylphosphino)-9,9-dimethylxanthene (11.5 g, 19.88 mmol), tris(dibenzylideneacetone)dipalladium (9.1 g, 9.94 mmol) and cesium carbonate (48.40 g, 148.6 mmol) were dissolved in 150 mL of toluene under the protection of nitrogen, and heated to reflux for 4 hours. The reaction solution was cooled to room temperature, filtered, and concentrated under reduced pressure, the resulting residue was purified by silica gel column chromatography (eluent: B system) to obtain N-(4-(4-(dimethylamino)piperidin-1-yl)-2-nitrophenyl)acetamide 7b (6.40 g, brownish black solid), yield: 42%.

MS m/z (ESI): 307.0 [M+1]

Step 2

1-(4-Amino-3-nitrophenyl)-N,N-dimethylpiperidin-4-amine

N-(4-(4-(Dimethylamino)piperidin-1-yl)-2-nitrophenyl)acetamide 7b (6.40 g, 20.89 mmol) and potassium hydroxide (5.86 g, 104.4 mmol) were dissolved in 80 mL of a mixed solvent of methanol and water (V/V=1/1), and heated to reflux for 2 hours. The reaction solution was concentrated under reduced pressure, 100 mL of water were added, extracted with ethyl acetate (50 mL×3), the organic phases were combined and washed with water (50 mL×3) and saturated saline solution (50 mL) successively, dried over anhydrous sodium sulfate, filtered, and concentrated under reduced pressure, the resulting residue was purified by silica gel column chromatography (eluent: B system) to obtain 1-(4-amino-3-nitrophenyl)-N,N-dimethylpiperidin-4-amine 7c (5.4 g, brownish black solid), yield: 97.8%.

MS m/z (ESI): 265.0 [M+1]

Step 3

Tert-butyl N-(2,6-dichloro-3,5-dimethoxy-phenyl)-N-[[6-[4-[4-(dim ethyl amino)-1-piperidinyl]-2-nitro-anilino]-methyl-carbamoyl]carbamate Tert-butyl (6-chloropyrimidin-4-yl)(methyl)carbamoyl-(2,6-dichloro-3,5-dimethoxyphenyl)carbamate 1g (500 mg, 1.02 mmol), 1-(4-amino-3-nitrophenyl)-N,N-dimethylpiperidin-4-amine 7c (285.07 mg, 1.02 mmol), 4,5-bis(diphenylphosphino)-9,9-dimethylxanthene (117.66 mg, 0.203 mmol), tris(dibenzylideneacetone)dipalladium (93.11 mg, 0.101 mmol) and cesium carbonate (662.57 mg, 2.03 mmol) were dissolved in 15 mL of toluene under the protection of argon, heated to 120° C. and reacted for 4 hours. The reaction solution was concentrated under reduced pressure and the resulting residue was purified by silica gel column chromatography (eluent: B system) to obtain tert-butyl N-(2, 6-dichloro-3,5-dimethoxy-phenyl)-N-[[6-[4-[4-(dimethyl amino)-1-piperidinyl]-2-nitro-anilino]-methyl-carbamoyl] carbamate 7d (420 Mg, brownish red solid), yield: 57.4%.

MS m/z (ESI): 718.8 [M+1]

Step 4

Tert-butyl N-[6-[[tert-butoxycarbonyl-2,6-dichloro-3,5-dimethoxy-phenyl)carbamoyl]-methyl-amino] pyrimidin-4-yl]-N-[4-[4-(dimethyl amino)-1-piperidinyl]-2-nitro-phenyl]carbamate Tert-butyl N-(2,6-dichloro-3,5-dimethoxy-phenyl)-N-[[6-[4-[4-(dim ethyl amino)-1-piperidinyl]-2-nitro-anilino]-methyl-carbamoyl]carbamate 7d (400 mg, 0.536 mmol) was dissolved in 20 mL of tetrahydrofuran, the solution was added with di-tert-butyl dicarbonate (242.63 mg, 1.11 mmol) and 4-dimethylaminopyridine (20.37 mg, 0.167 mmol), and heated to 75° C. and reacted for 2 hours. The reaction solution was concentrated under reduced pressure and the resulting residue was purified by silica gel column chromatography (eluent: B system) to obtain tert-butyl N-[6-[[tert-butoxycarbonyl-2,6-dichloro-3,5-dimethoxy-phenyl)carbamoyl]-methyl-amino]pyrimidin-4-yl]-N-[4-[4-(dimethylamino)-1-piperidinyl]-2-nitro-phenyl]carbamate 7e (323 mg, orange-yellow solid), yield: 70.9%.

MS m/z (ESI): 818.8 [M+1]

Step 5

Tert-butyl N-[[6-[2-amino-N-tert-butoxycarbonyl-4-[4-(dimethylamino)-1-piperidinyl]anilino]pyrimidin-4-yl]methylcarbamoyl]-N-2,6-dichloro-3,5-dimethoxy-phenyl)carbamate Tert-butyl N-[6-[[tert-butoxycarbonyl-2,6-dichloro-3,5-dimethoxy-phenyl)carbamoyl]-methyl-amino]pyrimidin-4-yl]-N-[4-[4-(dimethylamino)-1-piperidinyl]-2-nitro-phenyl]carbamate 7e (322 mg, 0.393 mmol) was dissolved in 10 mL methanol, the solution was added with Raney nickel (300 mg) and reacted for 3 hours at room temperature under the protection of hydrogen. The reaction solution was filtered, and concentrated under reduced pressure, the resulting residue was purified by silica gel column chromatography (eluent: B system) to obtain tert-butyl N-[[6-[2-amino-N-tert-butoxycarbonyl-4-[4-(dimethylamino)-1-piperidinyl]anilino]pyrimidin-4-yl]methylcarbamoyl]-N-2,6-dichloro-3,5-dimethoxy-phenyl)carbamate 7f (202 mg, yellow solid), yield: 65.1%.

MS m/z (ESI): 788.8 [M+1]

Step 6

Tert-butyl N-[[6-[2-acrylamido-N-tert-butoxycarbonyl-4-[4-(dimethylamino)-1-piperidinyl]anilino]pyrimidin-4-yl]methylcarbamoyl]-N-2,6-dichloro-3,5-dimethoxy-phenyl)carbamate Tert-butyl N-[[6-[2-amino-N-tert-butoxycarbonyl-4-[4-(dimethylamino)-1-piperidinyl]anilino]pyrimidin-4-yl]methylcarbamoyl]-N-2,6-dichloro-3,5-dimethoxy-phenyl)carbamate 7f (188 mg, 0.238 mmol) was dissolved in 10 mL dichloromethane, the solution was added with N,N-diisopropylethylamine (131.42 mg, 0.952 mmol) and acryloyl chloride (43.09 mg, 0.476 mmol), and reacted at room temperature for 2 hours. The reaction solution was concentrated under reduced pressure, the resulting residue was purified by silica gel column chromatography (eluent: B system) to obtain tert-butyl N-[[6-[2-acrylamido-N-tert-butoxycarbonyl-4-[4-(dimethylamino)-1-piperidinyl]anilino]pyrimidin-4-yl]methylcarbamoyl]-N-2,6-dichloro-3,5-dimethoxy-phenyl)carbamate 7g (162 mg, pale yellow solid), yield: 80.6%. MS m/z (ESI): 842.8 [M+1]

Step 7

N-(2-((6-(3-(2,6-Dichloro-3,5-dimethoxyphenyl)-1-methylureido)pyrimidin-4-yl)amino)-5-(4-(dimethylamino)piperidin-1-yl)phenyl)acrylamide Tert-butyl N-[[6-[2-acrylamido-N-tert-butoxycarbonyl-4-[4-(dimethylamino)-1-piperidinyl]anilino]pyrimidin-4-yl]methylcarbamoyl]-N-2,6-dichloro-3,5-dimethoxy-phenyl)carbamate 7g (162 mg, 0.192 mmol) was dissolved in 5 mL of dichloromethane, the solution was added with 5 mL of trifluoroacetic acid, and reacted at room temperature for 1 hour. The reaction solution was concentrated under reduced pressure, 10 mL of dichloromethane was added, washed with saturated sodium carbonate solution (10 mL×2), concentrated under reduced pressure, the resulting residue was purified by silica gel column chromatography (eluent: B system) to obtain N-(2-((6-(3-(2,6-dichloro-3,5-dimethoxyphenyl)-1-methylureido)pyrimidin-4-yl)amino)-5-(4-(dimethylamino)piperidin-1-yl)phenyl)acrylamide 7 (66 mg, pale yellow solid), yield: 53.4%.

MS m/z (ESI): 642.8 [M+1]

$^1$H NMR (400 MHz, CDCl$_3$) δ 12.56 (s, 1H), 8.37 (s, 1H), 8.10 (s, 1H), 7.64 (s, 1H), 7.23 (d, J=8.9 Hz, 2H), 6.77 (s, 1H), 6.51 (s, 1H), 6.41 (d, J=16.5 Hz, 1H), 6.24 (d, J=10.2 Hz, 1H), 5.93 (s, 1H), 5.76 (d, J=9.8 Hz, 1H), 3.91 (s, 6H), 3.80 (d, J=12.1 Hz, 2H), 3.28 (s, 3H), 2.76 (s, 3H), 2.56 (s, 6H), 2.01 (s, 2H), 1.74 (s, 2H).

Example 8

N-(5-(4-Cyclopropylpiperazin-1-yl)-2-((6-(3-(2,6-dichloro-3,5-dimethoxyphenyl)-1-methylureido)pyrimidin-4-yl)amino)phenyl)acrylamide

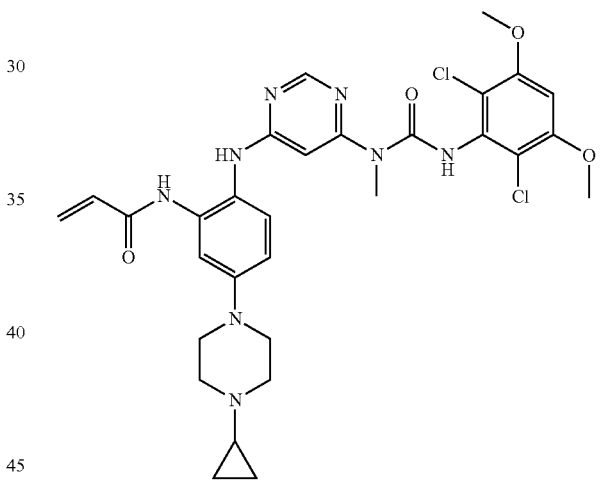

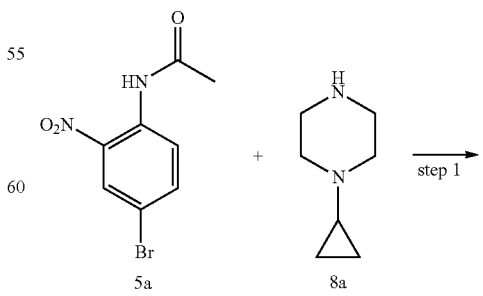

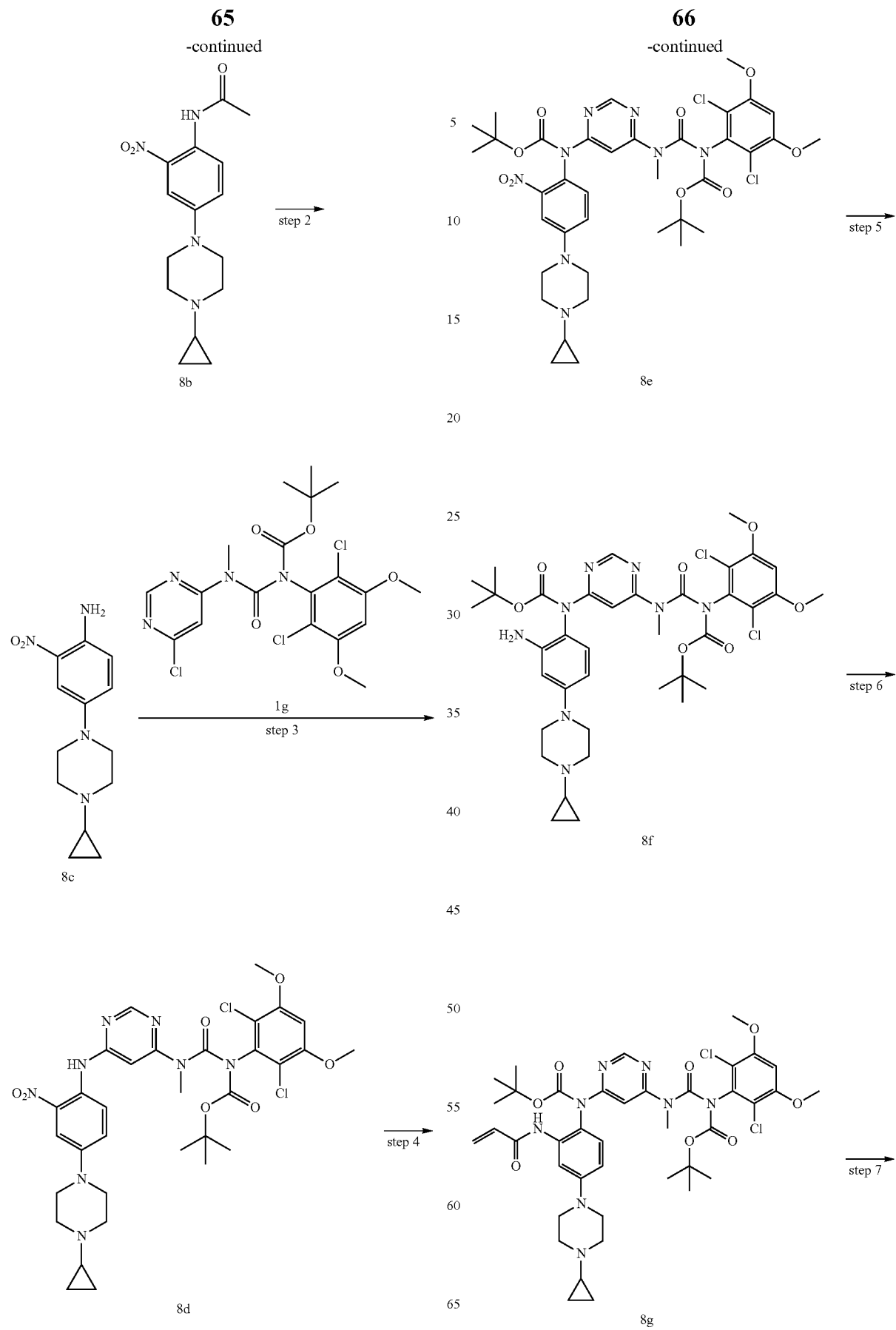

-continued

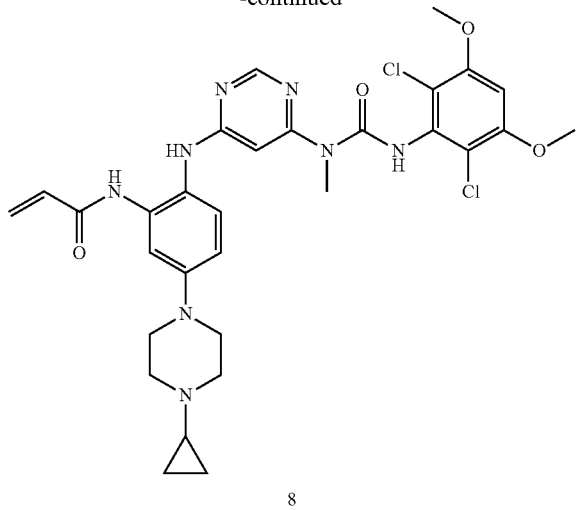

8

Step 1

N-(4-(4-Cyclopropylpiperazin-1-yl)-2-nitrophenyl) acetamide

N-(4-Bromo-2-nitrophenyl)acetamide 5a (1.00 g, 3.86 mmol), 1-cyclopropylpiperazine 8a (483.26 mg, 3.86 mmol), 4,5-bis(diphenylphosphino)-9,9-dimethylxanthene (446.71 mg, 0.772 mmol), tris(dibenzylideneacetone)dipalladium (353.48 mg, 0.386 mmol) and cesium carbonate (2.52 g, 7.72 mmol) were dissolved in 10 mL of toluene under the protection of argon, the solution was heated to 120° C. and reacted for 4 hours. The reaction solution was cooled to room temperature, concentrated under reduced pressure, and the resulting residue was purified by silica gel column chromatography (eluent: B system) to obtain N-(4-(4-cyclopropylpiperazin-1-yl)-2-nitrophenyl) acetamide 8b (500 mg, red solid), yield: 42.7%.

MS m/z (ESI): 304.9 [M+1]

Step 2

4-(4-Cyclopropylpiperazin-1-yl)-2-nitroaniline

N-(4-(4-Cyclopropylpiperazin-1-yl)-2-nitrophenyl)acetamide 8b (424 mg, 1.39 mmol) was dissolved in 50 mL of a mixed solvent of ethanol and water (V/V=3/2), heated to 95° C. and reacted for 4 hours. The reaction solution was concentrated under reduced pressure, extracted with dichloromethane (20 mL×3), the organic phases were combined, concentrated under reduced pressure, the resulting residue was purified by silica gel column chromatography (eluent: B system) to obtain 4-(4-cyclopropylpiperazin-1-yl)-2-nitroaniline 8c (311 mg, reddish brown solid), yield: 85.2%.

MS m/z (ESI): 263.0 [M+1]

Step 3

Tert-butyl N-[[6-[4-(4-cyclopropylpiperazin-1-yl)-2-nitro-anilino]pyrimidin-4-yl]methylcarbamoyl]-N-(2,6-dichloro-3,5-dimethoxy-phenyl)carbamate Tert-butyl (6-chloropyrimidin-4-yl)(methyl)carbamoyl-(2,6-dichloro-3,5-dimethoxyphenyl)carbamate 1g (500 mg, 1.02 mmol), 4-(4-cyclopropylpiperazin-1-yl)-2-nitroaniline 8c (266.71 mg, 1.02 mmol), 4,5-bis(diphenylphosphino)-9, 9-dimethylxanthene (117.66 mg, 0.203 mmol), tris(dibenzylideneacetone)dipalladium (93.11 mg, 0.102 mmol) and cesium carbonate (662.57 mg, 2.03 mmol) were dissolved in 20 mL of toluene under the protection of argon, the mixture was heated to 120° C. and reacted for 4 hours. The reaction solution was cooled to room temperature, and concentrated under reduced pressure, the resulting residue was purified by silica gel column chromatography (eluent: B system) to obtain tert-butyl N-[[6-[4-(4-cyclopropylpiperazin-1-yl)-2-nitroanilino]pyrimidin-4-yl]methylcarbamoyl]-N-(2,6-dichloro-3,5-dimethoxy-phenyl)carbamate 8d (612 mg, reddish brown solid), yield: 83.9%.

MS m/z (ESI): 716.8 [M+1]

Step 4

Tert-butyl N-[[6-[N-tert-butoxycarbonyl-4-(4-cyclopropylpiperazin-1-yl)-2-nitro-anilino]pyrimidin-4-yl]-methylcarbamoyl]-N-2,6-dichloro-3,5-dimethoxy-phenyl)carbamate Tert-butyl N-[[6-[4-(4-cyclopropylpiperazin-1-yl)-2-nitroanilino]pyrimidin-4-yl]methylcarbamoyl]-N-(2,6-dichloro-3,5-dimethoxy-phenyl)carbamate 8d (612 mg, 0.853 mmol) was dissolved in 20 mL of tetrahydrofuran, di-tert-butyl dicarbonate (372.26 mg, 1.71 mmol) and 4-dimethylaminopyridine (52.09 mg, 0.426 mmol) were added, the reaction solution was heated to 75° C. and reacted for 2 hours. The reaction solution was concentrated under reduced pressure, the resulting residue was purified by silica gel column chromatography (eluent: B system) to obtain tert-butyl N-[[6-[N-tert-butoxycarbonyl-4-(4-cyclopropylpiperazin-1-yl)-2-nitro-anilino]pyrimidin-4-yl]-methylcarbamoyl]-N-2,6-dichloro-3,5-dimethoxy-phenyl)carbamate 8e (655 mg, orange-yellow solid), yield: 93.9%.

MS m/z (ESI): 816.8 [M+1]

Step 5

Tert-butyl N-[[6-[2-amino-N-tert-butoxycarbonyl-4-(4-cyclopropylpiperazin-1-yl)anilino]pyrimidin-4-yl]-methyl-carbamoyl]-N-2,6-dichloro-3,5-dimethoxy-phenyl)carbamate Tert-butyl N-[[6-[N-tert-butoxycarbonyl-4-(4-cyclopropylpiperazin-1-yl)-2-nitro-anilino]pyrimidin-4-yl]-methyl-carbamoyl]-N-2,6-dichloro-3,5-dimethoxy-phenyl)carbamate 8e (650 mg, 0.795 mmol) was dissolved in 20 mL of methanol, the solution was added with Raney nickel (1.00 g), reacted at room temperature for 2 hours under a hydrogen atmosphere. The reaction solution was filtered and concentrated under reduced pressure to obtain a crude product of tert-butyl N-[[6-[2-amino-N-tert-butoxycarbonyl-4-(4-cyclopropylpiperazin-1-yl)anilino]pyrimidin-4-yl]-methyl-carbamoyl]-N-2,6-dichloro-3,5-dimethoxy-phenyl)carbamate 8f (596 mg, orange-yellow solid), yield: 95.2%.

Step 6

Tert-butyl N-[[6-[2-acrylamido-N-tert-butoxycarbonyl-4-(4-cyclopropylpiperazin-1-yl)anilino]pyrimidin-4-yl]-methyl-carbamoyl]-N-2,6-dichloro-3,5-dimethoxy-phenyl)carbamate Tert-butyl N-[[6-[2-amino-N-tert-butoxycarbonyl-4-(4-cyclopropylpiperazin-1-yl)anilino]pyrimidin-4-yl]-methyl-carbamoyl]-N-2,6-dichloro-3,5-dimethoxy-phenyl)carbamate 8f (565 mg, 0.717 mmol) was dissolved in 10 mL of dichloromethane, the solution was added with N,N-diisopropylethylamine (411.04 mg, 2.87 mmol) and acryloyl chloride (129.83 mg, 1.43 mmol) and reacted at room temperature for 10 minutes. 10 mL of a saturated sodium hydrogencarbonate solution was added to the reaction solution, extracted with dichloromethane (20 mL×3), and the organic phase was combined and concentrated under reduced pressure to obtain crude product of tert-butyl N-[[6-[2-acrylamido-N-tert-butoxycarbonyl-4-(4-cyclopropylpiperazin-1-yl)anilino]pyrimidin-4-yl]-methyl-carbamoyl]-N-2,6-dichloro-3,5-dimethoxy-phenyl)carbamate 8g (600 mg, yellow solid), yield: 99.5%.

MS m/z (ESI): 842.8 [M+1]

Step 7

N-(5-(4-Cyclopropylpiperazin-1-yl)-2-((6-(3-(2,6-dichloro-3,5-dimethoxyphenyl)-1-methylureido) pyrimidin-4-yl)amino)phenyl)acryl amide Tert-butyl N-[[6-[2-acrylamido-N-tert-butoxycarbonyl-4-(4-cyclopropylpiperazin-1-yl)anilino]pyrimidin-4-yl]-methyl-carbamoyl]-N-2,6-dichloro-3,5-dimethoxy-phenyl)carbamate 8g (600 mg, 0.713 mmol) was dissolved in 5 mL of dichloromethane, the solution was added with 5 mL of trifluoroacetic acid was added, and reacted at room temperature for 4 hours. The reaction solution was concentrated under reduced pressure, 10 mL of saturated sodium bicarbonate solution and 10 mL of dichloromethane were added, layered, the aqueous phase was extracted with dichloromethane (10 mL×2), the organic phases were combined and concentrated under reduced pressure, the resulting residue was purified by silica gel thin layer chromatography (eluent: B system) to obtain N-(5-(4-cyclopropylpiperazin-1-yl)-2-((6-(3-(2,6-di chloro-3,5-dimethoxyphenyl)-1-methylureido)pyrimidin-4-yl)amino)phenyl)acrylamide 8 (200 mg, pale yellow solid), yield: 43.9%.

MS m/z (ESI): 640.8 [M+1]

$^1$H NMR (400 MHz, CDCl$_3$) δ 12.55 (s, 1H), 8.38 (s, 1H), 7.71 (s, 2H), 7.21 (d, J=8.8 Hz, 1H), 6.76 (d, J=8.8 Hz, 2H), 6.52 (s, 1H), 6.42 (d, J=17.0 Hz, 1H), 6.21 (dd, J=16.8, 10.0 Hz, 1H), 5.86 (s, 1H), 5.77 (d, J=10.3 Hz, 1H), 3.92 (s, 6H), 3.27 (s, 7H), 2.80 (s, 4H), 1.62 (s, 1H), 0.51 (s, 4H).

Example 9

N-(5-(4-(Cyclopropyl(methyl)amino)piperidin-1-yl)-2-((6-(3-(2,6-dichloro-3,5-dimethoxyphenyl)-1-methylureido)-4-yl)amino)phenyl)acrylamide

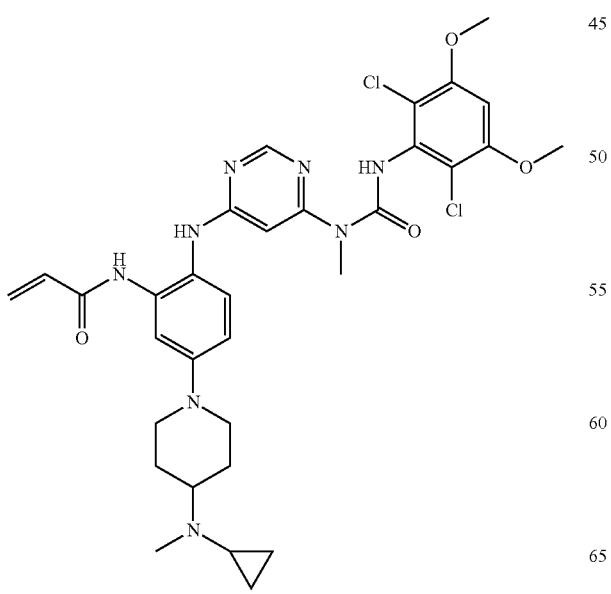

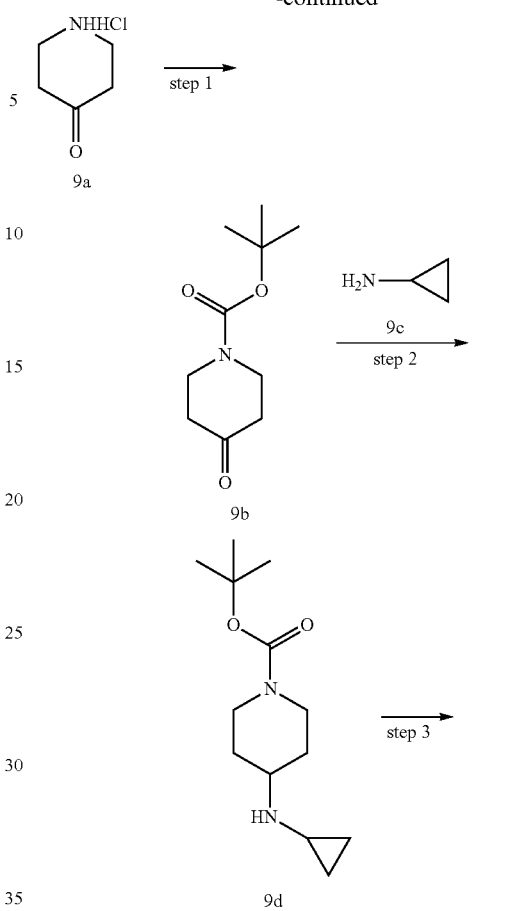

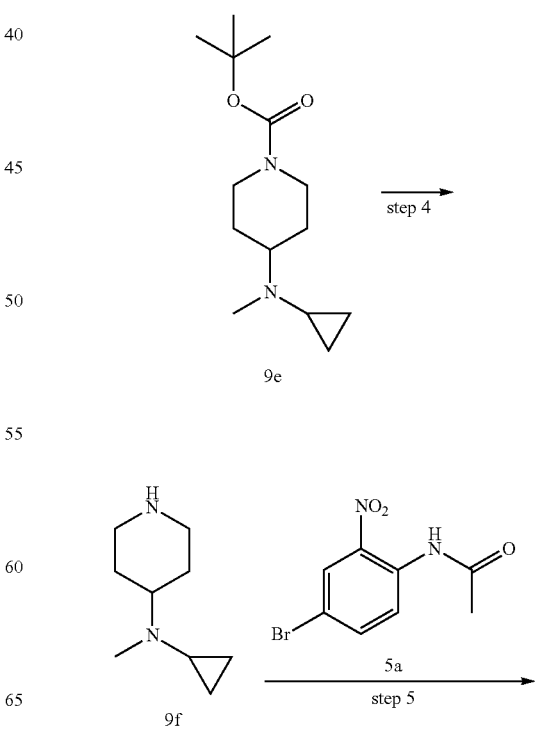

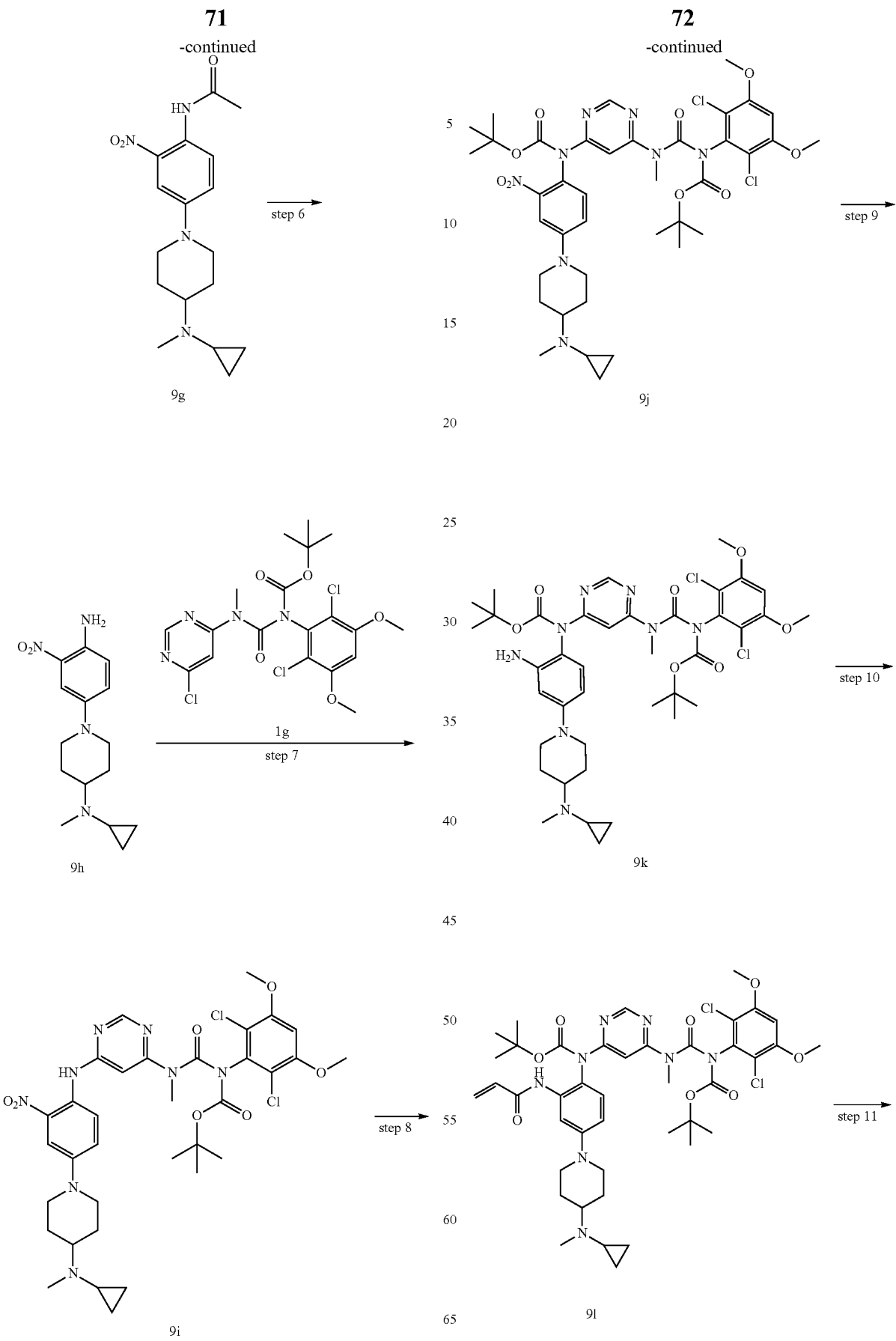

-continued

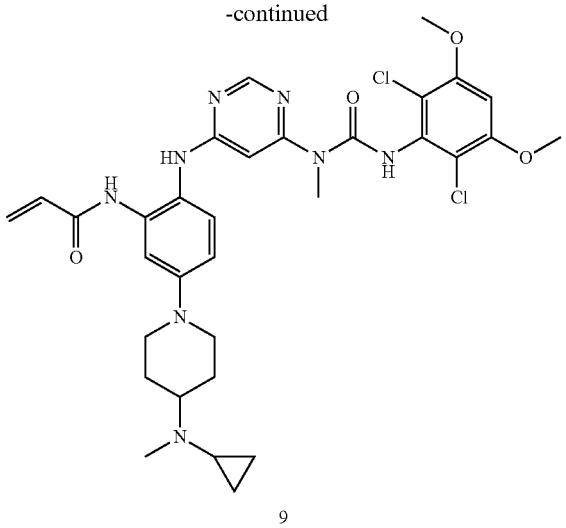

9

Step 1

Tert-butyl 4-oxopiperidine-1-carboxylate

Piperidin-4-one hydrochloride 9a (5.0 g, 36.8 mmol) was dissolved in 100 mL of tetrahydrofuran, triethylamine (7.7 mL, 55.2 mmol) was added, stirred for 5 min, and di-tert-butyl dicarbonate (9.6 g, 44.2 mmol) and 4-dimethylaminopyridine (225 mg, 1.84 mmol) were added, reacted at room temperature for 12 hours. The reaction solution was concentrated under reduced pressure, 100 mL of dichloromethane was added, washed with 1M hydrochloric acid solution (50 mL×2), saturated sodium carbonate solution (50 mL) and saturated sodium chloride solution (50 mL) successively, dried over anhydrous sodium sulfate, filtered, and concentrated under reduced pressure to obtain tert-butyl 4-oxopiperidine-1-carboxylate 9b (6.7 g, colorless solid), yield: 91.8%.

$^1$H NMR (400 MHz, CDCl$_3$) δ 3.71-3.74 (m, 4H), 2.43-2.46 (m, 4H), 1.50 (s, 9H)

Step 2

Tert-butyl 4-(cyclopropylamino)piperidine-1-carboxylate

Tert-butyl 4-oxopiperidine-1-carboxylate 9b (12.0 g, 60.2 mmol) was dissolved in 40 mL of ethanol, 40 mL of glacial acetic acid and cyclopropylamine 9c (4.2 mL, 60.2 mmol) were added and stirred for 0.5 hour, sodium cyanoborohydride (7.56 g, 120.4 mmol) was added and reacted at room temperature for 2 hours. The reaction solution was concentrated under reduced pressure, 500 mL of saturated ammonium chloride solution was added, extracted with ethyl acetate (500 mL), washed with saturated sodium carbonate solution (400 mL) and saturated sodium chloride solution (500 mL), dried over anhydrous sodium sulfate, filtered, and concentrated under reduced pressure to obtain tert-butyl 4-(cyclopropylamino)piperidine-1-carboxylate 9d (11.1 g, colorless liquid), yield: 77.1%.

$^1$H NMR (400 MHz, CDCl$_3$) δ 4.01-4.06 (m, 2H), 2.75-2.83 (m, 3H), 2.14-2.17 (m, 1H), 1.90-1.94 (m, 2H), 1.45 (s, 9H), 1.26-1.30 (m, 2H), 0.46-0.50 (m, 2H), 0.38-0.40 (m, 2H)

Step 3

Tert-butyl 4-(cyclopropyl(methyl)amino)piperidine-1-carboxylate

Tert-butyl 4-(cyclopropylamino)piperidine-1-carboxylate 9d (11.1 g, 46.2 mmol) was dissolved in 300 mL of acetonitrile, and potassium carbonate (19.15 g, 138.6 mmol) and methyl iodide (3.45 mL, 55.44 mmol), reacted at room temperature for 2 hours. The reaction solution was filtered, concentrated under reduced pressure, the resulting residue was purified by silica gel column chromatography (eluent: A system) to obtain tert-butyl 4-(cyclopropyl(methyl)amino)piperidine-1-carboxylate 9e (8.0 g, colorless liquid), yield: 68%.

$^1$H NMR (400 MHz, CDCl$_3$) δ 4.13-4.19 (m, 2H), 2.63-2.69 (m, 3H), 2.39 (s, 3H), 1.82-1.99 (m, 3H), 1.47-1.54 (m, 2H), 1.49 (s, 9H), 0.54-0.56 (m, 4H)

Step 4

N-Cyclopropyl-N-methylpiperidin-4-amine

Tert-butyl 4-(cyclopropyl(methyl)amino)piperidine-1-carboxylate 9e (8.0 g, 31.4 mmol) was dissolved in 30 mL of dichloromethane, 5 mL of trifluoroacetic acid was added, and reacted at room temperature for 2 hours. The reaction solution was concentrated under reduced pressure, the resulting residue was added to 20 mL of dichloromethane and continued to concentrate under reduced pressure, and 50 mL of dichloromethane was added again to dissolve it, and then potassium carbonate powder was added until no bubbles were produced, filtered, concentrated under reduced pressure to obtain N-cyclopropyl-N-methylpiperidin-4-amine 9f (3.8 g, brown liquid), yield: 78.3%.

$^1$H NMR (400 MHz, CDCl$_3$) δ 3.12-3.15 (m, 2H), 2.60-2.63 (m, 2H), 2.52-2.56 (m, 1H), 2.34 (s, 3H), 1.85-1.95 (m, 2H), 1.75-1.78 (m, 1H), 1.46-1.50 (m, 2H), 0.46-0.50 (m, 2H), 0.40-0.42 (m, 2H)

Step 5

N-(4-(4-(Cyclopropyl(methyl)amino)piperidin-1-yl)-2-nitrophenyl)acetamide

N-(4-Bromo-2-nitrophenyl)acetamide 5a (6.18 g, 23.8 mmol), N-cyclopropyl-N-methylpiperidin-4-amine 9f (3.35 g, 21.7 mmol), 4,5-bis(diphenylphosphino)-9,9-dimethylxanthene (2.51 g, 4.34 mmol), tris(dibenzylideneacetone)dipalladium (3.97 g, 4.34 mmol) and cesium carbonate (21.2 g, 65.1 mmol) were dissolved in 100 mL of toluene under the protection of argon, heated to 110° C. and reacted for 4 hours. The reaction solution was cooled to room temperature, extracted with 500 mL of ethyl acetate, washed with water (300 mL×2) and saturated sodium chloride solution (300 mL) successively, dried over anhydrous sodium sulfate, filtered, the filtrate was concentrated under reduced pressure, the resulting residue was purified by silica gel column chromatography (eluent: A system) to obtain N-(4-(4-(cyclopropyl(methyl)amino)piperidin-1-yl)-2-nitrophenyl)acetamide 9g (5.0 g, brown solid), yield: 69.4%.

MS m/z (ESI): 333.0 [M+1]

Step 6

1-(4-Amino-3-nitrophenyl)-N-cyclopropyl-N-methylpiperidin-4-amine

N-(4-(4-(Cyclopropyl(methyl)amino)piperidin-1-yl)-2-nitrophenyl)acetamide 9g (5.0 g, 15.0 mmol) and potassium hydroxide (8.4 g, 150.0 mmol) was dissolved in a mixed solution of 320 mL of water and ethanol (V/V=1/15), heated to 90° C. and reacted for 2 hours. The reaction solution was concentrated under reduced pressure, 500 mL of ethyl acetate was added, layered, the organic phase was washed with water (400 mL), saturated sodium chloride solution (400 mL) and saturated sodium carbonate solution (400 mL), and concentrated under reduced pressure, the resulting residue was purified by silica gel column chromatography (eluent: B system) to obtain 1-(4-amino-3-nitrophenyl)-N-cyclopropyl-N-methylpiperidin-4-amine 9h (2.60 g, brown oil), yield: 57.5%. MS m/z (ESI): 291.0 [M+1]

Step 7

Tert-butyl N-[[6-[4-[4-[cyclopropyl(methyl)amino)-1-piperidyl]-2-nitro-anilino]pyrimidin-4-yl]methyl-carbamoyl]-N-(2,6-dichloro-3,5-dimethoxy-phenyl)carbamate Tert-butyl (6-chloropyrimidin-4-yl)(methyl)carbamoyl-(2,6-dichloro-3,5-dimethoxyphenyl)carbamate 1g (491.8 mg, 1.00 mmol), 1-(4-amino-3-nitrophenyl)-N-cyclopropyl-N-methylpiperidin-4-amine 9h (290.4 mg, 1.00 mmol), 4,5-bis(diphenylphosphino)-9,9-dimethylxanthene (115.7 mg, 0.20 mmol), tris(dibenzylideneacetone)dipalladium (183.0 mg, 0.20 mmol) and cesium carbonate (977 mg, 3.00) were dissolved in 10 mL of toluene under the protection of argon and reacted at 110° C. for 5 hours. The reaction solution was cooled to room temperature, filtered, concentrated under reduced pressure, and the resulting residue was purified by silica gel column chromatography (eluent: B system) to obtain tert-butyl N-[[6-[4-[4-[cyclopropyl(methyl)amino)-1-piperidyl]-2-nitroanilino]pyrimidin-4-yl]methylcarbamoyl]-N-(2,6-dichloro-3,5-dimethoxy-phenyl)carbamate 9i (310 mg, brown solid), yield: 41.6%.

MS m/z (ESI): 744.8 [M+1]

Step 8

Tert-butyl N-[[6-[N-tert-butoxycarbonyl-4-[4-[cyclopropyl(methyl)amino]-1-piperidyl]-2-nitroanilino]pyrimidin-4-yl]methylcarbamoyl]-N-(2,6-dichloro-3,5-dimethoxy-phenyl)carbamate Tert-butyl N-[[6-[4-[4-[cyclopropyl(methyl)amino)-1-piperidyl]-2-nitroanilino]pyrimidin-4-yl]methylcarbamoyl]-N-(2,6-dichloro-3,5-dimethoxy-phenyl)carbamate 9i (300 mg, 0.40 mmol) was dissolved in 10 mL of tetrahydrofuran, di-tert-butyl dicarbonate (176 mg, 0.80 mmol) and 4-dimethylaminopyridine (48.8 mg, 0.40 mmol) were added, the reaction solution was heated to 80° C. and reacted for 4 hours. The reaction solution was concentrated under reduced pressure, and the resulting residue was purified by silica gel column chromatography (eluent: B system) to obtain tert-butyl N-[[6-[N-tert-butoxycarbonyl-4-[4-[cyclopropyl(methyl)amino]-1-piperidyl]-2-nitroanilino]pyrimidin-4-yl]methylcarbamoyl]-N-(2,6-dichloro-3,5-dimethoxy-phenyl)carbamate 9j (200 mg, brown solid), yield: 58.1%.

MS m/z (ESI): 846.8 [M+1]

Step 9

Tert-butyl N-[[6-[2-amino-N-tert-butoxycarbonyl-4-[4-[cyclopropyl(methyl)amino]-1-piperidyl]anilino]pyrimidin-4-yl]-methyl-carbamoyl]-N-(2,6-dichloro-3,5-dimethoxy-phenyl)carbamate Tert-butyl N-[[6-[N-tert-butoxycarbonyl-4-[4-[cyclopropyl(methyl)amino]-1-piperidyl]-2-nitroanilino]pyrimidin-4-yl]methylcarbamoyl]-N-(2,6-dichloro-3,5-dimethoxy-phenyl)carbamate 9j (200 mg, 0.23 mmol) was dissolved in 10 mL of a mixed solvent of methanol and tetrahydrofuran (V/V=1/1), the solution was added with Raney nickel (200 mg), and reacted at room temperature for 3 hours under a hydrogen atmosphere. The reaction solution was filtered, concentrated under reduced pressure, and the resulting residue was purified by silica gel column chromatography (eluent: B system) to obtain tert-butyl N-[[6-[2-amino-N-tert-butoxycarbonyl-4-[4-[cyclopropyl(methyl)amino]-1-piperidyl]anilino]pyrimidin-4-yl]-methyl-carbamoyl]-N-(2,6-dichloro-3,5-dimethoxy-phenyl)carbamate 9k (90 mg, white solid), yield: 46.6%.

MS m/z (ESI): 817.8 [M+1]

Step 10

Tert-butyl N-[[6-[2-acrylamido-N-tert-butoxycarbonyl-4-[4-[cyclopropyl(methyl)amino]-1-piperidinyl]anilino]pyrimidin-4-yl]-methyl-carbamoyl]-N-(2,6-dichloro-3,5-dimethoxy-phenyl)carbamate Tert-butyl N-[[6-[2-amino-N-tert-butoxycarbonyl-4-[4-[cyclopropyl(methyl)amino]-1-piperidinyl]anilino]pyrimidin-4-yl]-methyl-carbamoyl]-N-(2,6-dichloro-3,5-dimethoxy-phenyl)carbamate 9k (90 mg, 0.11 mmol) was dissolved in 5 mL of dichloromethane, N,N-diisopropylethylamine (0.1 mL, 0.55 mmol) and acryloyl chloride (20 mg, 0.22 mmol) were added under an ice bath, reacted for 1 hour at room temperature. 50 mL of dichloromethane was added, layered, the organic phase was washed with saturated sodium carbonate solution (500 mL) and saturated sodium chloride (50 mL), concentrated under reduced pressure, and the resulting residue was purified by silica gel column chromatography (eluent: B system) to obtain tert-butyl N-[[6-[2-acrylamido-N-tert-butoxycarbonyl-4-[4-[cyclopropyl(methyl)amino]-1-piperidinyl]anilino]pyrimidin-4-yl]-methyl-carbamoyl]-N-(2,6-dichloro-3,5-dimethoxy-phenyl)carbamate 9l (70 mg, light yellow solid), yield: 72.9%.

MS m/z (ESI): 869.8 [M+1]

Step 11

N-(5-(4-(Cyclopropyl(methyl)amino)piperidin-1-yl)-2-((6-(3-(2,6-dichloro-3,5-dimethoxyphenyl)-1-methylureido)-4-yl)amino)phenyl)acrylamide Tert-butyl N-[[6-[2-acrylamido-N-tert-butoxycarbonyl-4-[4-[cyclopropyl(methyl)amino]-1-piperidinyl]anilino]pyrimidin-4-yl]-methyl-carbamoyl]-N-(2,6-dichloro-3,5-dimethoxy-phenyl)carbamate 9l (68 mg, 0.078 mmol) was dissolved in 2 mL of dichloromethane, the solution was added with 1 mL of trifluoroacetic acid under an ice bath, and reacted at room temperature for 2 hours. 50 ml of dichloromethane was added to the reaction solution, and washed with saturated sodium carbonate solution (50 mL×2), the organic phase was concentrated under reduced pressure, the resulting residue was purified by silica gel thin layer chromatography (eluent: B system) to obtain N-(5-(4-(cyclopropyl(methyl)amino)piperidin-1-yl)-2-((6-(3-(2,6-dichloro-3,5-dimethoxyphenyl)-1-methylureido)-4-yl)amino)phenyl)acrylamide 9 (30 mg, pale yellow solid), yield: 57.6%.

MS m/z (ESI): 669.9 [M+1]

$^1$H NMR (400 MHz, CDCl$_3$) δ 12.56 (s, 1H), 8.36 (s, 1H), 8.10 (s, 1H), 7.67 (s, 1H), 7.24 (m, 1H), 6.76 (d, J=9.0 Hz,

1H), 6.51-6.53 (m, 1H), 6.41 (d, J=7.5 Hz, 1H), 6.21-6.27 (m, 1H), 5.95 (s, 1H), 5.76 (d, J=10.4 Hz, 1H), 3.91 (s, 6H), 3.74-3.81 (m, 2H), 3.35 (s, 3H), 2.83-2.86 (m, 1H), 2.71-2.77 (m, 2H), 2.55 (s, 3H), 2.02-2.10 (m, 3H), 1.80-1.82 (m, 2H), 0.85-0.87 (m, 2H), 0.68-0.84 (m, 2H)

Biological Evaluation

Test Example 1. Determination of the Effect of the Compounds of the Present Invention Against FGFR Kinase Activity The following method was used to determine the inhibition degree of the kinase activity of recombinant human FGFR protein by the compounds of the present invention under in vitro conditions. Cisbio Company's HTRF® KinEASE-TK tyrosine kinase kit (Cat. No: 62TK0PEB) was used in the present method, the kit was used to reflect the inhibitory effect of the compounds on FGFR kinase activity by determination of the phosphorylation degree of FGFR protein-mediated biotinylated polypeptide substrates based on the principle of time-resolved fluorescence energy resonance transfer (TF-FRET). For detailed experimental procedures, refer to the kit instructions. Recombinant human FGFR protein was purchased from Carna bioscience (Japan, Cat. No: FGFR1 #08-133, FGFR2 #08-134, FGFR3 #08-135, and FGFR4 #08-136).

The experimental procedure is briefly described as follows: the test compound was first dissolved in DMSO to prepare a stock solution, and then gradiently diluted with the buffer provided in the kit, and the final concentration of the test compound in the reaction system ranges from 10 µM to 0.1 nM. The concentration of ATP solution (Sangon Biotech (Shanghai) Co., Ltd., A600311) used in the test is the ATP Km concentration corresponding to each FGFR subtype measured in advance, and the ATP Km concentration corresponding to FGFR1-4 is 100 µM, 40 µM, 40 µM and 120 µM respectively. The reaction was carried out in a 384-well microplate, the compound and a certain amount of FGFR protein was firstly added to the well, and incubated at room temperature for 5-30 minutes, then the ATP solution and the biotinylated polypeptide substrate solution were added to the reaction solution, and incubated for 50 minutes with shaking at room temperature. Subsequently, an anti-phosphotyrosine antibody coupled with a europium compound and streptavidin coupled with the modified allophycocyanin XL665 were added to the reaction, and incubation was continued for 1 hour at room temperature with shaking. After the incubation ended, the fluorescence intensity values of the respective wells at an excitation wavelength of 304 nm and emission wavelengths of 620 nM and 665 nM were measured in a TF-FRET mode on a microplate reader. The percentage inhibition of the compound at each concentration was calculated by comparison with the fluorescence intensity ratio of the control group (0.1% DMSO), and the nonlinear regression analysis was performed on the logarithm values of the concentrations of the compounds—inhibition rate by GraphPad Prism 5 software to obtain the $IC_{50}$ value of compounds, see Table 1.

TABLE 1

IC$_{50}$ data for inhibition of FGFR enzyme activity by the compounds of the present invention

| Example No. | IC$_{50}$ (nM) | | | |
|---|---|---|---|---|
| | FGFR1 | FGFR2 | FGFR3 | FGFR4 |
| The compound of Example 108 of WO2015057938 | 210 | 579 | 575 | 14 |
| 1 | 160 | 777 | 557 | 5 |
| 2 | 87 | 189 | 179 | 4.6 |
| 3 | 465 | 2428 | 715 | 2 |
| 4 | 382 | 165 | 439 | 1.3 |
| 5 | 624 | 533 | 989 | 2.4 |
| 6 | 544 | 368 | 731 | 2.2 |
| 7 | 176 | 405 | 729 | 1.1 |
| 8 | 618 | 644 | 880 | 2.5 |
| 9 | 244 | 228 | 311 | 3.8 |

As can be seen from Table 1, the compounds of the present invention have a better inhibitory effect on FGFR4, and the selectivity is superior to FGFR1, FGFR2 and FGFR3, and the inhibitory activity of the compounds of the present invention against FGFR4 is superior to that of the compound of Example 108 of WO2015057938 (which is prepared and identified according to Example 108 of WO2015057938).

Test Example 2: Determination of Effect of the Compounds of the Present Invention Against Hepatocellular Carcinoma Tumor Cell Huh7 Activity The following method was used to determine the effect of the compounds of the present invention against tumor cell proliferation. For the FGFR4 subtype, hepatocellular carcinoma tumor cells Huh7 (purchased from the Cell Resource Center of Shanghai Institutes for Biological Sciences, Chinese Academy of Sciences) were used to determine the inhibition against the activity of hepatocellular carcinoma tumor cells. Huh7 cells were cultured in a DMEM medium containing 10% of fetal bovine serum, 100 U of penicillin and 100 µg/mL of streptomycin. Cultured in an incubator of 37° C., 5% CO$_2$. Hepatocellular carcinoma tumor cell activity was measured by using a kit of Cell Counting Kit-8 (Dojindo, Dojindo Molecular Technologies, Inc).

The experimental method was carried out according to the steps of the kit instructions, and is briefly described as follows: the test compound was first dissolved in DMSO to prepare a stock solution, and then gradiently diluted with the corresponding medium of the cells to prepare a test sample, and the final concentration of the compound was in the range of 30 µM to 0.01 nM. Tumor cells in the logarithmic phase were seeded into 96-well cell culture plates at a suitable density, cultured in an incubator of 37° C., 5% CO$_2$ overnight, then test compound samples were added and continued to culture the cells for 72 hours. After completion of the culture, a suitable volume of CCK-8 test solution was added to each well, and incubated at 37° C. for 1 to 4 hours, and then the absorbance values of the respective wells at 450 nM were read on a microplate reader. The percentage inhibition of the compounds at each concentration was calculated by comparison with the absorbance value of the control group (0.3% DMSO), and the nonlinear regression analysis was performed on the logarithm value of concentrations of the compounds—inhibition rate by GraphPad Prism 5 software to obtain the $IC_{50}$ value of compounds, see Table 2.

TABLE 2

IC$_{50}$ data for inhibition of hepatocellular carcinoma tumor cells Huh7 activity by the compounds of the present invention

| Example No. | IC$_{50}$(nM)/Huh7 |
|---|---|
| The compound of Example 108 of WO2015057938 | 18 |
| 5 | 12 |
| 6 | 10 |
| 7 | 4.8 |

As can be seen from Table 2, the compounds of the present invention have a remarkable proliferation inhibitory effect against FGFR4 abnormal hepatocellular carcinoma tumor cells, and are superior to the compound of Example 108 of WO2015057938.

Test Example 3: Test of the Growth Inhibitory Effect of the Compounds of the Present Invention Against Human Hepatocellular Carcinoma Tumor Cell Huh7 Tumor-Bearing BALB/c Nude Mice Xenografts 1. Experiment Objectives This test was used to evaluate the growth inhibitory effect of the compound of Example 5 and the compound of Example 108 of WO2015057938 on the Huh7 tumor-bearing BALB/c nude mice xenografts, administered twice daily for 22 days, orally or intraperitoneally.

2. Preparation of Test Substances 2.1 Preparation of Dosing Formulation of Vehicle:

A suitable volume of a formulation containing 5% of DMSO, 10% of PEG 300, 8% of Tween 80, and 77% of physiological saline (v/v) was prepared as a blank group administration test solution.

2.2 Preparation of Dosing Formulation the Compound of Example 108 of WO2015057938

An appropriate amount of the compound of Example 108 of WO2015057938 was weighed and placed in a glass vial; an appropriate volume of DMSO was added, followed by vortex and sonication until the drug was completely dissolved, and then an appropriate amount of solvent TPS (Tween80:PEG300:normal saline=8%:10%:77% (v/v/v) solution) was added, followed by vortex and sonication evenly, so that the ratio of DMSO:PEG300:Tween-80:normal saline was 5:10:8:77 (v/v/v/v), and prepared dosing formulation with a concentration of 2.5 mg/mL.

2.3 Preparation of Intraperitoneal Injection Formulation of the Compound of Example 5

An appropriate amount of the compound of Example 5 was weighed and placed in a glass bottle; an appropriate volume of DMSO was added, followed by vortex and sonication until the drug was completely dissolved, and then an appropriate amount of solvent TPS (Tween80:PEG300:normal saline=8%: 10%: 77% (v/v/v) solution) was added, followed by vortex and sonication evenly, so that the ratio of DMSO:PEG300:Tween-80:normal saline was 5:10:8:77 (v/v/v/v), and prepared dosing formulation with concentrations of 2.5 mg/mL and 5 mg/mL.

2.4 Preparation of Oral Formulation of the Compound of Example 5

600 mg of the compound of Example 5 was weighed and placed in a glass bottle; an appropriate volume of 3.92 mL of EtOH was added, 9.8 mL of PEG400 was added, and then 5.88 mL of 1 M HCl was added, followed by vortex and sonication evenly so that the ratio of EtOH:PEG400:water was 20:50:30 (v/v/v), and prepared dosing formulation with a concentration of 30 mg/mL.

3. Experimental Animals

Species and strains: 45 of BALB/c nude mice, SPF, female, 7 to 9 weeks old (16 to 22 grams), healthy, adapted to environmental for 5 to 7 days. Certification No.: 1140070017310, purchased from Beijing Vital River Laboratory Animal Technology Co., Ltd.

4. Hepatocellular Carcinoma Tumor Cell Huh7 Culture

On day 0, Huh7 cells were cultured in DMEM medium containing 10% of fetal bovine serum, 100 U of penicillin, and 100 µg/mL of streptomycin. And cultured in an incubator of 37° C., 5% CO$_2$. Before inoculation, logarithmic phase cells were taken, digested with 0.25% of trypsin, then washed with PBS (Phosphate Buffered Saline, phosphate buffer), the cells were resuspended in serum-free medium for counting, and the cell concentration was adjusted to $3.3\times10^7$ cells/mL (1:1 Matrigel, PBS).

5. Animal Inoculation and Grouping

Each mouse was inoculated subcutaneously in the right axilla with 150 µL of cell suspension ($5.0\times10^6$ cells/mouse) under sterile conditions. On day 12 after inoculation, when the tumor grew to a volume of 200-300 mm$^3$, mice with similar tumor volume and good shape were selected (the shape was as single spherical as possible, no irregular shape or multiple tumors gathered together) and divided into 5 groups, each group had 9 mice.

6. Animal Administration and Observation

Each group of animals was administrated (intraperitoneal injection (ip) or oral administration (po)) a test substance twice a day (bid) at a fix time per day according to the body weight of the animals. The first dose was administered on the day of grouping (day 13 after inoculation), and continued for 22 days, the body weight of the animals was recorded daily.

Group 1, solvent control group, intraperitoneal injection of formulation of vehicle, bid, administration volume of 10 mL/kg; Group 2, intraperitoneal administration of the compound of Example 108 of WO2015057938, administered at a dose of 25 mg/kg, twice a day (bid); Groups 3 and 4, intraperitoneal injection of the compound of Example 5 at doses of 25 mg/kg and 50 mg/kg respectively, bid; Group 5, intragastric injection of the compound of Example 5 at a dose of 300 mg/kg, bid.

The formation of tumor in the inoculated part of each group of animals was observed. The long diameter (Y) and short diameter (X) of the tumor nodules were measured twice a week using vernier calipers and calculated according to the following formula:

$$\text{Volume of tumor nodules } (V): V=(X^2Y)/2.$$

Evaluation index of antitumor activity: tumor growth inhibition rate TGI (%), relative tumor proliferation rate T/C (%).

The relative tumor volume (RTV) is calculated as:

$$RTV=100\times TV_t/TV_{initial}$$

wherein, $TV_{initial}$ is the tumor volume measured at the time of grouping administration; $TV_t$ is the tumor volume at each measurement during administration.

The calculation formula for the relative tumor proliferation rate (% T/C) is:

$$\% \ T/C=100\%\times(RTV_T/RTV_C)$$

wherein, $RTV_T$ represents RTV of the treatment group; $RTV_C$ represents RTV of the solvent control group.

The calculation formula for the tumor growth inhibition rate TGI (%) is:

$$TGI=100\% \times [1-(TV_{t(T)}-TV_{initial(T)})/(TV_{t(C)}-TV_{initial(C)})]$$

wherein, $TV_{t(T)}$ represents the tumor volume at each measurement in the treatment group; $TV_{initial(T)}$ represents the tumor volume of the treatment group at the time of grouping administration; $TV_{t(C)}$ represents the tumor volume at each measurement in the solvent control group; $TV_{initial(C)}$ represents the tumor volume of the solvent control group at the time of grouping administration.

The calculation formula for the tumor weight inhibition rate IR (%) is:

$$IR=100\% \times (W_C-W_T)/W_C$$

wherein, $W_C$ represents the tumor weight of the control group; $W_T$ represents the tumor weight of the treatment group.

The calculation formula for the weight loss rate of animals is (see FIG. 3 for the results):

$$\text{Weight loss rate of animals}=100\% \times (BW_{initial}-BW_t)/BW_{initial}$$

wherein, $BW_t$ represents the body weight of the animal at each measurement during administration; $BW_{initial}$ represents the body weight of the animal at the time of grouping administration.

7. Results

A graph showing changes in mean tumor volume of xenografts of hepatocellular carcinoma tumor cell Huh7 tumor-bearing BALB/c nude mice by the compound of Example 108 of WO2015057938 and the compound of Example 5 of the present invention is shown in FIG. 1.

Figure 2:
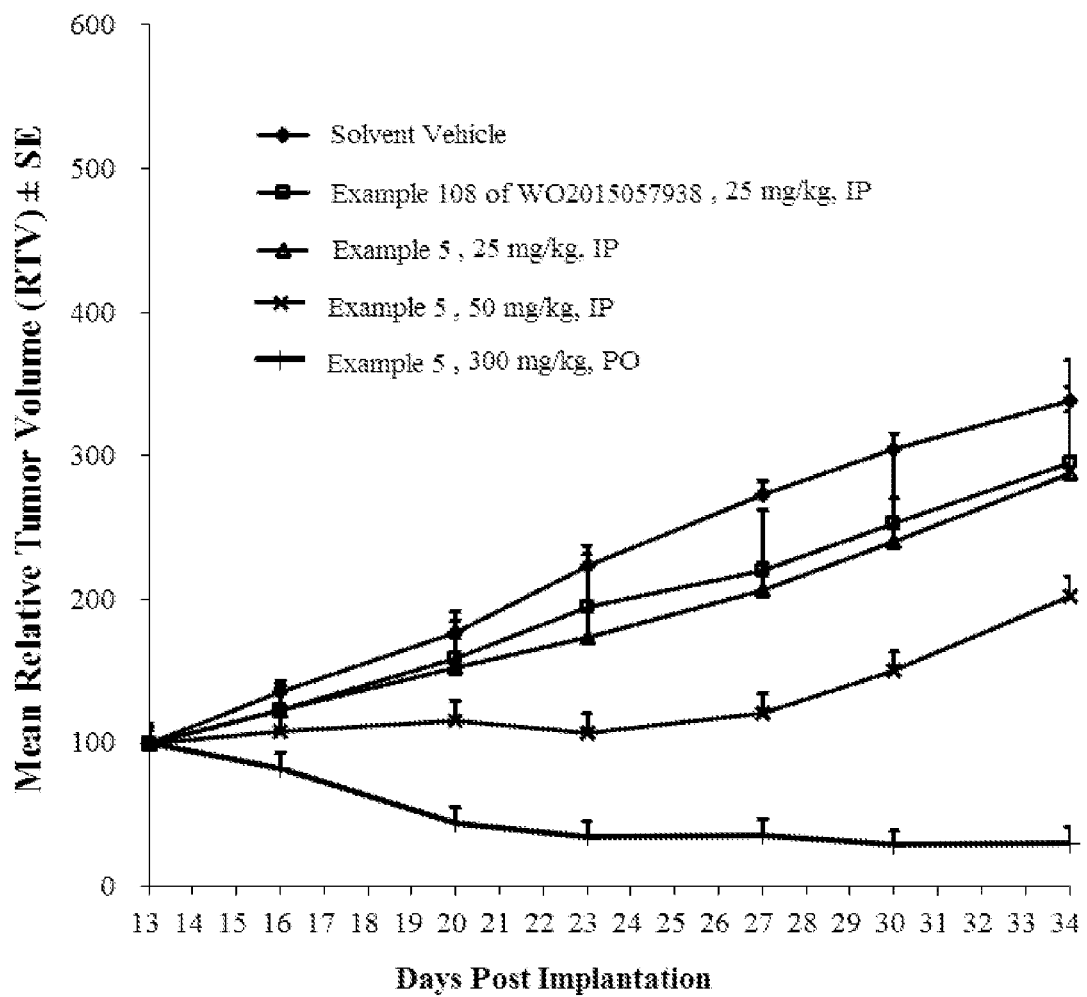
FIG. 2 is a graph showing changes in mean relative tumor volume of xenografts of hepatocellular carcinoma tumor cell Huh7 tumor-bearing BALB/c nude mice by the compound of Example 108 of WO2015057938 and the compound of Example 5 of the present invention in Test Example 3.

A graph showing changes in mean relative tumor volume of xenografts of hepatocellular carcinoma tumor cell Huh7 tumor-bearing BALB/c nude mice by the compound of Example 108 of WO2015057938 and the compound of Example 5 of the present invention is shown in FIG. 2.

Figure 3:
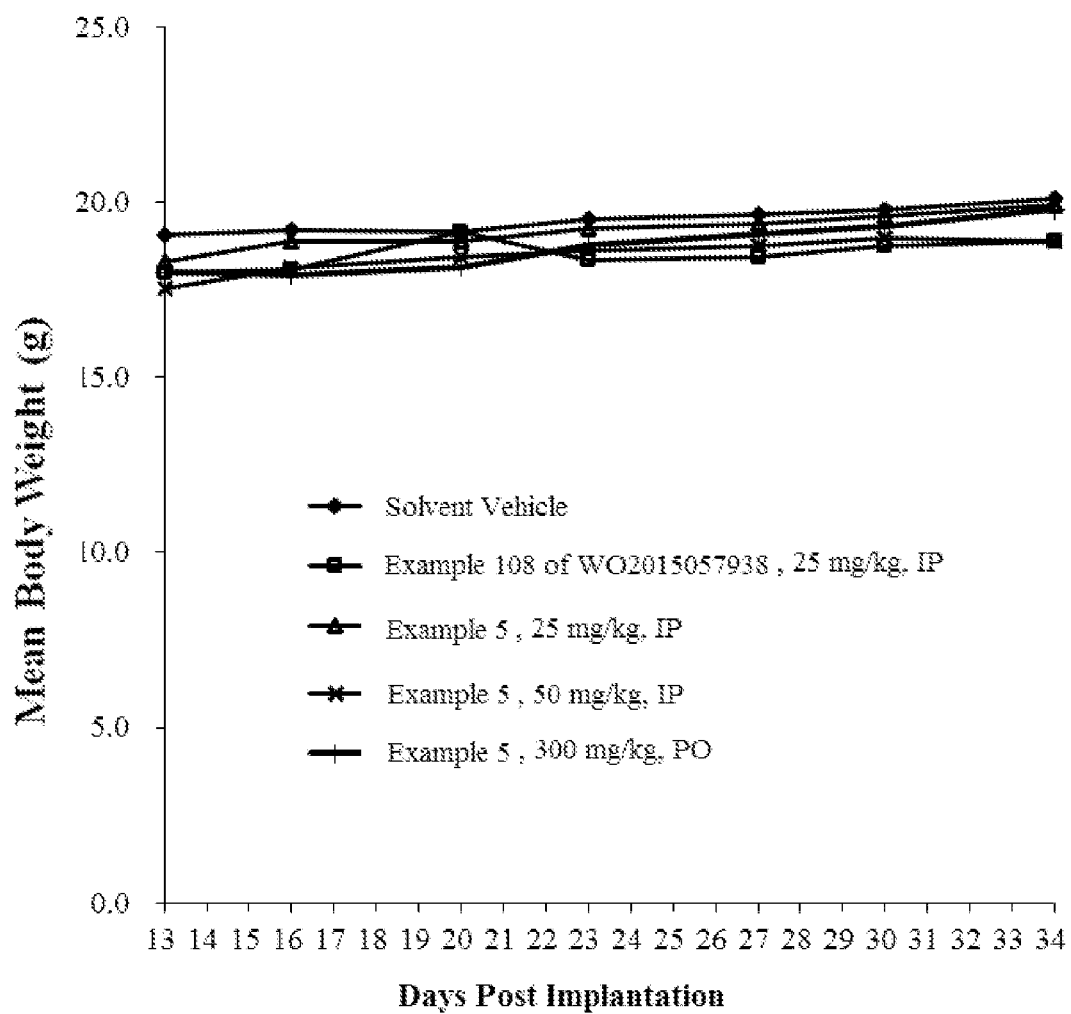
FIG. 3 is a graph showing changes in body weight of hepatocellular carcinoma tumor cell Huh7 tumor-bearing BALB/c nude mice by the compound of Example 108 of WO2015057938 and the compound of Example 5 of the present invention in Test Example 3.

A graph showing changes in body weight of hepatocellular carcinoma tumor cell Huh7 tumor-bearing BALB/c nude mice by the compound of Example 108 of WO2015057938 and the compound of Example 5 of the present invention is shown in FIG. 3.

TABLE 3

Growth inhibition rate (TGI %) of the compound of the present invention against hepatocellular carcinoma tumor cell Huh7 tumor-bearing BALB/c nude mice xenografts

| Group | Days after inoculation Tumor growth inhibition rate (TGI %) | | | | | |
|---|---|---|---|---|---|---|
| | Day 16 | Day 20 | Day 23 | Day 27 | Day 30 | Day 34 |
| The compound of Example 108 of WO2015057938 25 mg/kg (IP, bid) | 34% | 21% | 21% | 29% | 24% | 16% |
| The compound of Example 5 25 mg/kg (IP, bid) | 33% | 31% | 40% | 40% | 32% | 20% |
| The compound of Example 5 50 mg/kg (IP, bid) | 78% | 81% | 95% | 89% | 76% | 57% |
| The compound of Example 5 300 mg/kg (PO, bid) | 147% | 172% | 153% | 137% | 135% | 129% |

TABLE 4

Relative tumor growth rate T/C (%) of the compound of the present invention on hepatocellular carcinoma tumor cell Huh7 tumor-bearing BALB/c nude mice xenografts

| Group | Days after inoculation Relative tumor growth rate T/C (%) | | | | | | |
|---|---|---|---|---|---|---|---|
| | Day 13 | Day 16 | Day 20 | Day 23 | Day 27 | Day 30 | Day 34 |
| The compound of Example 108 of WO2015057938 25 mg/kg (IP, bid) | 100% | 91% | 90% | 87% | 81% | 83% | 87% |
| The compound of Example 5 25 mg/kg (IP, bid) | 100% | 91% | 86% | 78% | 76% | 79% | 85% |
| The compound of Example 5 50 mg/kg(IP, bid) | 100% | 80% | 65% | 48% | 44% | 49% | 60% |
| The compound of Example 5 300 mg/kg (PO, bid) | 100% | 61% | 25% | 16% | 13% | 9.4% | 9.0% |

TABLE 5

Tumor weight and tumor weight inhibition rate of each group of animals at the end of the experiment

| Group | Dosage of administration (mg/kg) | Administration method | Tumor weight (g) Mean ± standard error | Tumor weight inhibition rate (%) |
|---|---|---|---|---|
| Solvent control | — | IP, BID | 0.9306 ± 0.0924 | / |
| The compound of Example 108 of WO2015057938 | 25 | IP, bid | 0.9106 ± 0.0583 | 2.2% |
| The compound of Example 5 | 25 | IP, bid | 0.8393 ± 0.0602 | 10% |
| The compound of Example 5 | 50 | IP, bid | 0.6473 ± 0.0597 | 30% |
| The compound of Example 5 | 300 | PO, bid | 0.0562 ± 0.0069 | 94% |

TABLE 6

Body weight and weight loss rate of each group of animals during drug administration

| Group | | Days after inoculation Animal body weight ± standard error (g) or weight loss rate (%) | | | | | | |
|---|---|---|---|---|---|---|---|---|
| | | Day 13 | Day 16 | Day 20 | Day 23 | Day 27 | Day 30 | Day 34 |
| Solvent control | g | 19.1 ± 0.3 | 19.2 ± 0.3 | 19.2 ± 0.4 | 19.5 ± 0.4 | 19.6 ± 0.4 | 19.8 ± 0.4 | 20.1 ± 0.4 |
| | % | 0% | −0.64% | −0.52% | −2.3% | −2.9% | −3.7% | −5.4% |
| The compound of Example 108 of WO2015057938 25 mg/kg (IP, bid) | g | 18.0 ± 0.3 | 18.1 ± 0.3 | 19.2 ± 0.4 | 18.3 ± 0.2 | 18.4 ± 0.3 | 18.7 ± 0.2 | 18.9 ± 0.3 |
| | % | 0% | −0.62% | −6.7% | −2.0% | −2.7% | −4.2% | −5.0% |
| The compound of Example 5 25 mg/kg(IP, bid) | g | 18.3 ± 0.3 | 18.9 ± 0.3 | 18.9 ± 0.3 | 19.2 ± 0.3 | 19.4 ± 0.3 | 19.6 ± 0.3 | 19.9 ± 0.3 |
| | % | 0% | −3.1% | −3.0% | −5.0% | −5.8% | −7.0% | −8.6% |
| The compound of Example 5 50 mg/kg (IP, bid) | g | 17.5 ± 0.3 | 18.1 ± 0.3 | 18.4 ± 0.3 | 18.6 ± 0.3 | 18.7 ± 0.3 | 19.0 ± 0.4 | 18.9 ± 0.4 |
| | % | 0% | −3.2% | −5.0% | −6.1% | −6.8% | −8.0% | −7.5% |
| The compound of Example 5 300 mg/kg(PO, bid | g | 18.0 ± 0.3 | 17.9 ± 0.3 | 18.2 ± 0.3 | 18.8 ± 0.2 | 19.1 ± 0.3 | 19.3 ± 0.3 | 19.8 ± 0.3 |
| | % | 0% | 0.43% | −0.93% | −4.4% | −6.0% | −7.4% | −9.9% |

It can be seen from Tables 3 to 6 and FIGS. 1 to 3 that at the doses of 25 mg/kg (IP, bid), 50 mg/kg (IP, bid) and 300 mg/kg (PO, bid), the compound of Example 5 of the present invention had a significant growth inhibitory effect against the in vivo tumor model in mice established based on Huh-7 cells within 22 days, and had no significant body weight change. As can be seen from Tables 3-6, FIGS. 1 and 2, the activity of the compound of Example 5 was superior to that of the compound of Example 108 of WO2015057938 at a dose of 25 mg, IP.

All documents mentioned in the present application are hereby incorporated by reference in their entireties as each document is cited separately as a reference. It is to be understood that various modifications and changes may be made by those skilled in the art after reading the above teachings of the present invention, these equivalent forms also fall within the scope defined by the claims appended hereto.

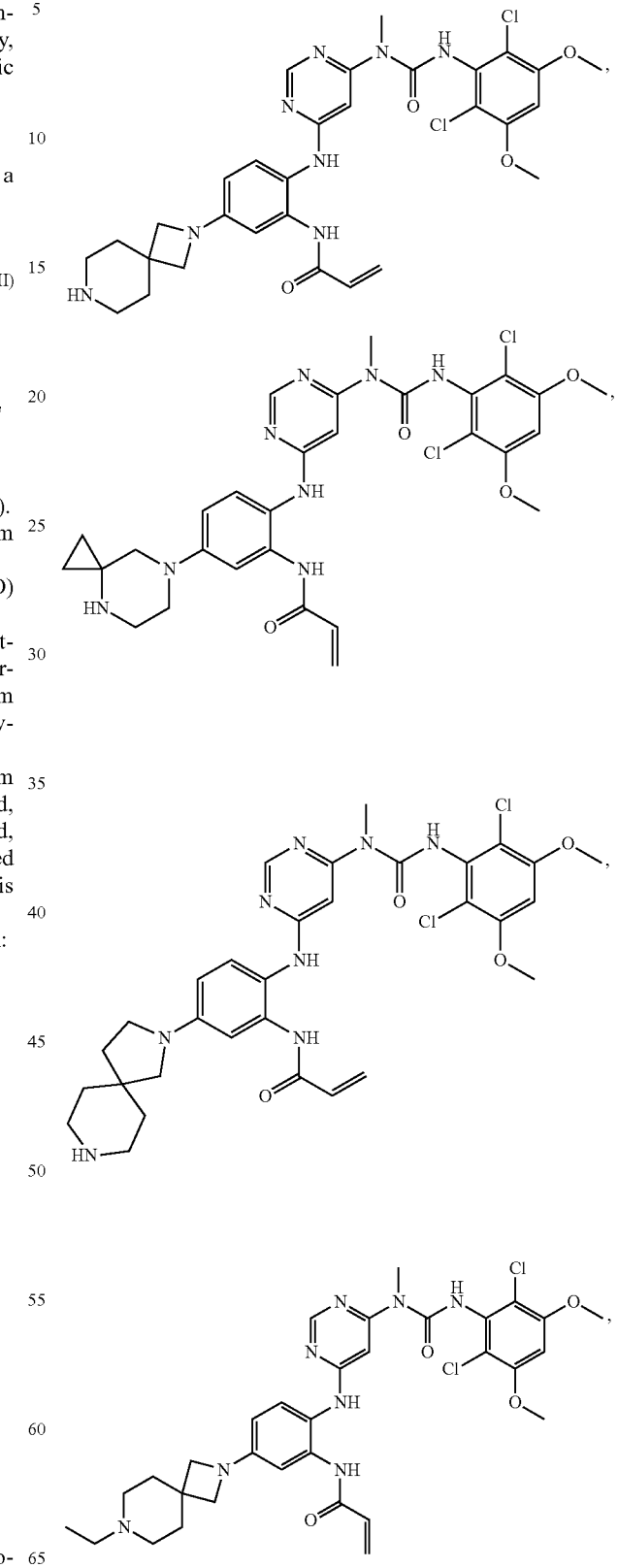

-continued
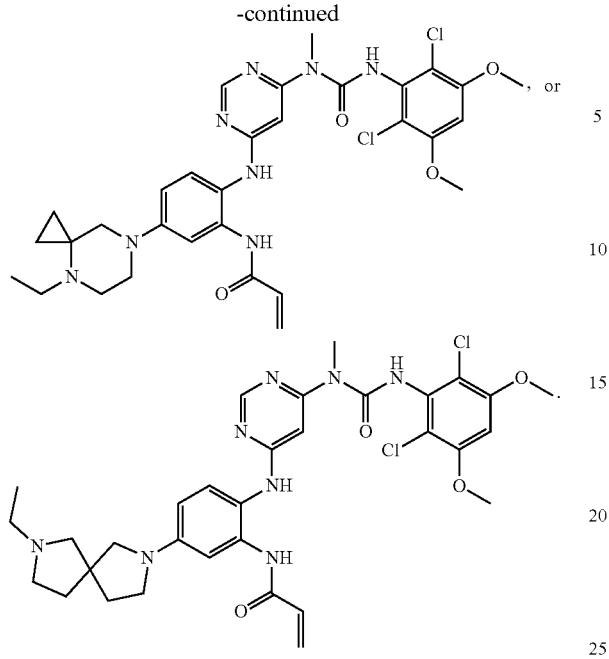

The invention claimed is:

1. A method for treating diseases of FGFR4 over-expression, comprising administering to a patient in need of treatment an effective amount of a compound represented by formula (I) or a stereoisomer, tautomer thereof or a pharmaceutically acceptable salt thereof:

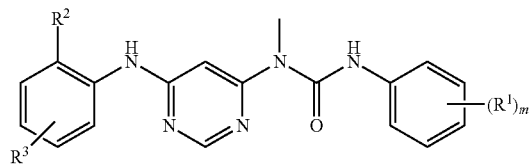

(I)

wherein:
each of $R^1$ is independently selected from alkyl, halogen, alkoxy, cycloalkyl, heterocyclyl, aryl, heteroaryl, $-NR^7R^8$, $-C(O)NR^7R^8$, $-C(O)R^9$, $-C(O)OR^9$ or $-NR^7C(O)R^8$, wherein the alkyl, alkoxy, cycloalkyl, heterocyclyl, aryl or heteroaryl is optionally further substituted by one or more substituents selected from the group consisting of hydroxyl, halogen, nitro, cyano, alkyl, alkoxy, cycloalkyl, heterocyclyl, aryl, heteroaryl, $-NR^7R^8$, $-C(O)NR^7R^8$, $-C(O)R^9$, $-C(O)OR^9$ and $-NR^7C(O)R^8$;

$R^2$ is selected from $-NR^4C(O)CR^5=CHR^6$ or $-NR^4C(O)C\equiv CR^5$;

$R^3$ is a spiroheterocyclyl, wherein the spiroheterocyclyl is optionally further substituted by one or more substituents selected from the group consisting of hydroxyl, halogen, nitro, cyano, alkyl, alkoxy, cycloalkyl, heterocyclyl, aryl, heteroaryl, haloalkoxy, $-NR^7R^8$, $-C(O)NR^7R^8$, $-C(O)R^9$, $-C(O)OR^9$ and $-NR^7C(O)R^8$;

each of $R^4$ is independently selected from hydrogen or alkyl, wherein the alkyl is optionally further substituted by one or more substituents selected from the group consisting of hydroxy, halogen, nitro, cyano, alkyl, alkoxy, cycloalkyl, heterocyclyl, aryl, heteroaryl, haloalkoxy, $-NR^7R^8$, $-C(O)NR^7R^8$, $-C(O)R^9$, $-C(O)OR^9$ and $-NR^7C(O)R^8$;

$R^5$ and $R^6$ are each independently selected from hydrogen, alkyl or halogen, wherein the alkyl is optionally further substituted by one or more substituents selected from the group consisting of hydroxy, halogen, nitro, cyano, alkyl, alkoxy, cycloalkyl, heterocyclyl, aryl, heteroaryl, haloalkoxy, $-NR^7R^8$, $-C(O)NR^7R^8$, $-C(O)R^9$, $-C(O)OR^9$ and $-NR^7C(O)R^8$;

$R^7$, $R^8$ and $R^9$ are each independently selected from hydrogen, alkyl, cycloalkyl, heterocyclyl, aryl or heteroaryl, wherein the alkyl, cycloalkyl, heterocyclyl, aryl or heteroaryl is optionally further substituted by one or more substituents selected from the group consisting of hydroxy, halogen, nitro, cyano, alkyl, alkoxy, cycloalkyl, heterocyclyl, aryl, heteroaryl, $-NR^{10}R^{11}$, $-C(O)NR^{10}R^{11}$, $-C(O)R^{12}$, $-C(O)OR^{12}$ and $-NR^{10}C(O)R^{11}$;

alternatively, $R^7$ and $R^8$ together with the N atom to which they are attached form a 4 to 8 membered heterocyclyl, wherein the 4 to 8 membered heterocyclic ring contains one or more N, O, $S(O)_n$ atoms, and the 4 to 8 membered heterocyclic ring is further substituted by one or more substituents selected from the group consisting of hydroxy, halogen, nitro, cyano, alkyl, alkoxy, cycloalkyl, heterocyclyl, aryl, heteroaryl, $=O$, $-NR^{10}R^{11}$, $-C(O)NR^{10}R^{11}$, $-C(O)R^{12}$, $-C(O)OR^{12}$ and $-NR^{10}C(O)R^{11}$;

R[10], R[11] and R[12] are each independently selected from hydrogen, alkyl, cycloalkyl, heterocyclyl, aryl or heteroaryl, wherein the alkyl, cycloalkyl, heterocyclyl, aryl or heteroaryl are optionally further substituted by one or more substituents selected from the group consisting of hydroxy, halogen, nitro, cyano, alkyl, alkoxy, cycloalkyl, heterocyclyl, aryl, heteroaryl, carboxylic acid or carboxylate;

m is 1, 2, 3 or 4; and n is 0, 1, or 2.

2. The method of claim 1, wherein the compound is a compound of formula (II):

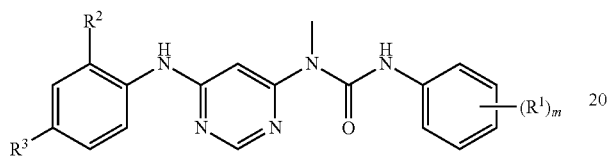

(II)

wherein R[1], R[2], R[3] and m are defined as in formula (I).

3. The method of claim 1, wherein R[1] is selected from halogen or alkoxy.

4. The method of claim 1, wherein R[2] is —NHC(O)CH=CH$_2$.

5. The method of claim 1, wherein R[3] is a monospiroheterocyclyl, and the monospiroheterocyclyl is optionally further substituted by one or more substituents selected from the group consisting of alkyl, alkoxy, cycloalkyl, heterocyclyl, aryl and heteroaryl.

6. The method of claim 1, wherein R[3] is selected from 3-membered/6-membered, 4-membered/4-membered, 4-membered/5-membered, 4-membered/6-membered, 5-membered-/5-membered or 5-membered/6-membered monospiroheterocyclyl, and the monospiroheterocyclyl is optionally further substituted by alkyl.

7. The method of claim 1, wherein R[3] is selected from:

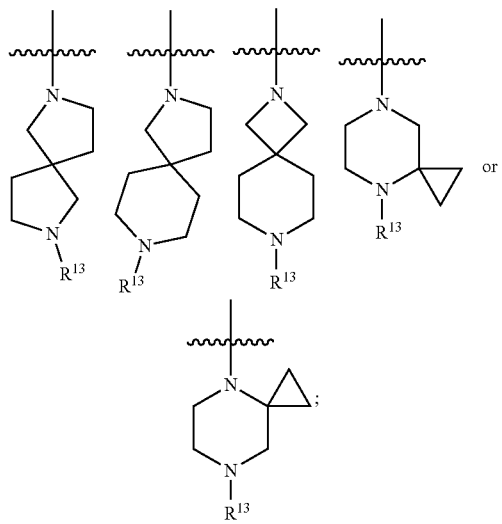

wherein each R[13] is independently selected from hydrogen, alkyl, alkoxy, cycloalkyl, heterocyclyl, aryl or heteroaryl.

8. The method of claim 1, wherein the compound is selected from: